US012233223B2

(12) United States Patent
Katz et al.

(10) Patent No.: US 12,233,223 B2
(45) Date of Patent: Feb. 25, 2025

(54) MEDICAL TUBE SECUREMENT DEVICE AND RELATED PRODUCTS AND METHODS

(71) Applicant: KMD Surgical Solutions, Inc., Winston-Salem, NC (US)

(72) Inventors: Adam J. Katz, Winston-Salem, NC (US); Thomas M. Johannsen, Centennial, CO (US)

(73) Assignee: KMD Surgical Solutions, Inc., Winston-Salem, NC (US)

(*) Notice: Subject to any disclaimer, the term of this patent is extended or adjusted under 35 U.S.C. 154(b) by 0 days.

(21) Appl. No.: 18/223,630

(22) Filed: Jul. 19, 2023

(65) Prior Publication Data

US 2023/0355931 A1    Nov. 9, 2023

Related U.S. Application Data

(63) Continuation of application No. PCT/US2023/010835, filed on Jan. 13, 2023.

(60) Provisional application No. 63/299,713, filed on Jan. 14, 2022.

(51) Int. Cl.
A61M 25/02    (2006.01)

(52) U.S. Cl.
CPC ..... A61M 25/02 (2013.01); *A61M 2025/0266* (2013.01); *A61M 2025/028* (2013.01)

(58) Field of Classification Search
CPC .......... A61M 25/02; A61M 2025/0266; A61M 2025/028; A61M 39/10; A61M 2039/1066; A61M 5/1418; A61M 1/912; A61M 16/0497; A61M 2025/0098; A61M 2039/0282; A61M 39/1055; A61M 2025/0253; A61M 2025/024; A61M 2025/026; A61M 39/0247
See application file for complete search history.

(56) References Cited

U.S. PATENT DOCUMENTS

| | | |
|---|---|---|
| 5,451,212 A | 9/1995 | Andersen |
| 8,361,034 B2 | 1/2013 | Spinoza |
| 8,435,216 B2 | 5/2013 | Spinoza |
| 8,652,107 B1 | 2/2014 | Elist et al. |
| 9,072,871 B2 | 7/2015 | Spinoza |
| 9,375,346 B1 * | 6/2016 | Sundheimer .......... A61F 13/622 |

(Continued)

FOREIGN PATENT DOCUMENTS

| | | |
|---|---|---|
| CN | 206081286 U | 4/2017 |
| WO | 9910250 A1 | 3/1999 |
| WO | 02066108 A1 | 8/2002 |

OTHER PUBLICATIONS

James J. Elist, et al. (2016) The Elist Drain Retainer: A New Adherent Drain Retainer with Antibacterial Properties. Open Journal of Urology, 6, 165-172. http://dx.doi.org/10.4236/oju.2016.611027, Nov. 17, 2016, 8.

*Primary Examiner* — Nathan R Price
(74) *Attorney, Agent, or Firm* — Holzer Patel Drennan

(57) ABSTRACT

A medical tube securement device to secure a medical tube includes a variable-length securement sleeve having a securement portion, the internal cross-sectional area of which varies as the length of the securement sleeve is varied to permit receipt of a medical tube when the area is larger and to grip and retain the medical tube when the area is smaller. A bent sleeve retainer is selectively engageable to retain the securement sleeve, and a secured medical tube, in a bent configuration.

70 Claims, 46 Drawing Sheets

(56) References Cited

U.S. PATENT DOCUMENTS

| | | |
|---|---|---|
| 10,561,824 B2 | 2/2020 | Spinoza |
| 10,632,288 B2 | 4/2020 | Spinoza |
| 2008/0082081 A1* | 4/2008 | Melsheimer ........ A61J 15/0061 |
| | | 604/270 |
| 2009/0221970 A1 | 9/2009 | Spinoza |
| 2010/0305510 A1* | 12/2010 | Spinoza ............ A61M 16/0488 |
| | | 604/524 |
| 2011/0282309 A1* | 11/2011 | Adie ................... A61F 13/0209 |
| | | 604/319 |
| 2012/0022455 A1* | 1/2012 | Spinoza ................ A61M 39/10 |
| | | 604/533 |
| 2015/0141927 A1 | 5/2015 | Spinoza |
| 2015/0273185 A1 | 10/2015 | Spinoza |
| 2016/0206856 A1 | 7/2016 | Watson et al. |
| 2017/0105877 A1* | 4/2017 | Buteux ............... A61F 13/0206 |
| 2017/0224433 A1* | 8/2017 | Döring .................... A61M 1/34 |
| 2017/0326338 A1 | 11/2017 | Watson |
| 2020/0164134 A1* | 5/2020 | Glauber ................ A61M 25/04 |

* cited by examiner

MEDICAL TUBE SECUREMENT DEVICE AND RELATED PRODUCTS AND METHODS

REFERENCE TO RELATED APPLICATIONS

This application is a continuation of international patent application no. PCT/US2023/010835 entitled "Medical Tube Securement Device and Related Products And Methods" filed Jan. 13, 2023, which claims benefit of U.S. provisional patent application No. 63/299,713 entitled "Medical Tube Securement Device And Related Products And Methods" filed Jan. 14, 2022, the contents of each and both of which are incorporated herein by reference for all purposes.

FIELD

The invention relates to securement of medical tubes, such as medical drainage tubes, to a patient.

BACKGROUND

Medical tubes are tubes that are inserted into the body of a patient, often through a surgically-formed opening, and retained in place for a period of time to provide temporary access to an anatomical area of the patient during a medical procedure. A variety of medical tubes and insertion procedures are used to access various anatomical areas and for a variety of purposes. Some medical tubes are inserted to permit fluids or medical devices to be introduced into the patient. Examples of these include intravenous feeding tubes and catheter tubes. Other medical tubes are inserted to permit withdrawal of fluids from the patient. Examples of these include medical drainage tubes, such as those used to drain fluids such as exudate, from the vicinity of a wound, often from a surgical wound. Still other medical tubes are inserted for other purposes, such as a tracheal tube inserted into the trachea during a tracheotomy to provide an artificial air passageway.

After insertion of the medical tube into the patient, the medical tube must then be secured to the patient and retained in place for the medical procedure. A variety of tube securement techniques have been used for various medical procedures. A challenge for effective tube securement is to provide for retainment of the medical tube in a desired location and orientation for a desired time period without the tube migrating or being inadvertently moved, pushed into the patient or pulled out by the patient or a medical practitioner. Another challenge is securement of the medical tube in a manner so that the tube does not detrimentally obstruct or interfere with access to areas of the patient around the tube as may be desired or needed at various times for a medical procedure.

For some medical procedures, the medical tube is often inserted at a relatively small acute angle relative to the patient's skin at the location of insertion. This is common for vascular access tubes, such as for intravenous feeding tubes and venous catheter tubes.

For some other medical procedures, the medical tube is inserted at a larger angle relative to the skin, often approaching or being approximately perpendicular to the patient's skin at the location of insertion. This is often the case, for example, for medical drainage tubes and tracheal tubes.

For many situations, the location and positioning of the medical tube is a relative constant between procedures, and securement techniques have tended to develop around the constancy of the application. For example, a common securement technique for vascular access procedures is to tape the tube to the patient's skin adjacent to where the tube exists the patient, such that the secured tube extends approximately parallel to the patient's skin away from the tube insertion location. As another example, the positioning of tracheal tubes is relatively constant and specialized securement techniques have been developed accordingly.

Medical drainage tubes in particular present a unique challenge for effective securement because the location and positioning of the medical tube on the patient varies depending on the type of wound and where the wound is located that is to be drained. An additional complicating factor is that such medical drainage tubes may be present for an extended time, for example several weeks, and may include significant time when the patient is convalescing at home and is only occasionally present at a medical facility where medical practitioners can readily attend to problems that might develop with the drainage tube. A very common technique for securing medical drainage tubes has been suture fixation of the tube. Another technique has been to tape the tube to the patient's skin adjacent to the tube insertion location. However, to improve securement and to more firmly hold the drainage tube in position, a variety of medical drainage tube securement devices have been designed, many of which attach to the patient's skin adjacent to the drainage tube insertion location and have a retaining mechanism to engage and hold the tube in a desired position in the vicinity of where the drainage tube exits the patient. Although such drainage tube securement devices provide enhanced securement of the drainage tube and protection of the area around the drainage tube relative to simply taping the drainage tube to the patient's skin, there is a need for securement devices having increased versatility for enhanced performance across a variety of medical tube applications, including across different drainage tube applications.

SUMMARY

A first aspect of this disclosure is directed to medical tube securement devices to secure medical tubes inserted into patients, and which securement devices are versatile for use across a variety of medical tube securement applications, and especially across a wide variety of medical drainage tube applications. The securement devices are particularly well suited for medical tube securement applications in which the medical tube exits the patient at a relatively large angle, for example at angles approaching or approximately perpendicular to the adjacent skin surface of the patient, which as noted is often the case for drainage tube applications. In one conceptualization, such a medical tube securement device comprises a versatile combination of design features adaptable for beneficial use across such a wide variety of medical tube securement applications, and especially for securement of medical drainage tubes, wherein the securement device comprises:

an attachment pad configured to interface with skin of a patient for attachment of the securement device to the skin, and preferably the attachment pad has an adhesive surface to adhere the attachment pad to a surface of the skin;

a variable-length securement sleeve having a proximal end and a distal end at a longitudinal end opposite the proximal end, the securement sleeve being coupled to the attachment pad through a coupling structure adjacent the proximal end of the securement sleeve;

a tube passage configured to receive therethrough a medical tube for securement to a patient, the tube passage extending longitudinally through the securement sleeve; and the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and the length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device.

With the securement devices of the first aspect, the securement portion of the securement sleeve can be made of any appropriate material or materials of construction and construction design to provide for a desired variability in the cross-sectional area in the tube passage of the securement portion with changes in the length of the securement sleeve. In preferred implementations of the securement sleeve, the securement portion is made of a textile. Materials of construction for interlacing fibers of such a textile can include for example polymeric materials and/or metallic materials, with polymeric materials being preferred. Examples of textile structures that can be used in the securement portion include braided, woven, knotted, crocheted, tatted, felted or bonded (e.g., nonwoven) structures, with braided and woven structures being generally more preferred. Any of said materials for construction of the securement sleeve may be modified to contain and/or release adhesive substances, nano-barbs, nano-particles, or other modifications that facilitate (augment) the attachment of the securement sleeve to a medical tube. The materials may also be modified to contain and/or release antimicrobial agents (for example those described elsewhere herein in relation to an absorbent pad or attachment adhesive) or bioactive substances such as antibiotics or antiseptics.

As will be appreciated, a medical tube may have a uniform design along the entire length of the medical tube or may have different designs along different longitudinal portions of the medical tube. The medical tube may be comprised of a single-piece structure, or may be comprised of multiple longitudinally-connected pieces. Medical tubes with a single-piece structure may be comprised of one or more longitudinal segments that have differing shapes, sizes, functions, and/or material. The medical tube may include or be fluidly connected to a medical apparatus disposed inside of a patient (e.g., at a proximal end of the medical tube) and/or attached to a medical apparatus disposed outside of the patient (e.g., at a distal end of the medical tube). In the case of drainage tubes, for example, the medical drainage tube may include or be fluidly connected to a proximally-located drain structure disposed inside of the patient and configured to receive fluid from the patient to be drained away through the medical drainage tube. Some types of medical drain apparatuses may include a hub (i.e. an area where there is a transition in size, diameter, and/or shape between longitudinal segments of the same tube) adjacent a proximal end of a drainage tube that connects to a proximally-located drain structure disposed in the patient's body during use. It is also possible that the drainage tube and the drain structure comprise separate pieces that are connected through a hub. Other types of medical drain apparatuses do not include such a hub, and are sometimes referred to as "hubless" drains. Such hubless drain apparatuses may for example be constructed of a single piece including both a proximally-located drain structure and drain tube portion to transmit collected fluid away from the proximally-located drain structure. As will be appreciated, when reference is made to features of a medical tube to be disposed through or received in the securement sleeve, or more particularly the securement portion of the securement sleeve (for example to be gripped by the securement portion), the reference is only to the features of the portion of a medical tube to be disposed through the securement sleeve, or securement portion as the case may be. Other portions of the medical tube, disposed proximal or distal of the securement sleeve, or securement portion as the case may be, may have different features, including a different cross-sectional profile.

In preferred implementations of this first aspect, any particular securement device can be designed to secure a medical tube having a particular outer cross-sectional size (e.g., outer diameter of circular tubes) or narrow range of outer cross-sectional sizes, and a broad range of medical tube sizes and configurations can be covered by providing different securement devices each designed to receive and retain a different size of medical tube. For example, different securement device designs can be provided with the securement sleeves of the different securement device designs being configured to receive and secure different ones of a range of medical tube diameters. In this way the securement device can advantageously be provided for use to secure a broad range of different sizes of medical tubes. Also, although the description herein is provided primarily to securing medical tubes with a circular outer cross-section, as will be appreciated the securement portion of the securement sleeve can be configured to secure tubes having other outer cross-section configurations, for example elliptical or other oblong outer cross-sectional shapes.

A number of enhancement features can be used individually or in any combination in the securement device of this aspect.

In one enhancement, the securement device can include a bent sleeve holder that can be selectively engaged, or not engaged, with the securement sleeve to selectively retain, or not retain, the securement sleeve in a bent configuration, and preferably when the securement sleeve is retained in the bent configuration a retained bend in the securement sleeve includes at least a longitudinal portion of the securement portion of the securement sleeve. The capability to retain, or not, the securement sleeve in the bent configuration provides a significant advantage of permitting a medical tube to be conveniently manipulated for positioning and securement to the securement device when the securement sleeve is not in the bent configuration, and after securement the securement sleeve can be reconfigured into and retained in the bent configuration, in which bent configuration the securement sleeve and the medical tube can be more advantageously positioned to be out of the way and less susceptible to inadvertent bumps or other unintended interactions with the patient or medical professionals and in which securement of the medical tube to the securement device is advantageously enhanced as a consequence of the bend. In the latter regard, when the securement sleeve with a secured medical tube is in the bent configuration, the bend provides significant added resistance to possible slippage of the medical tube in the securement sleeve as a consequence of inadvertent pushing of the medical tube toward or pulling the medical tube away from a distal end of the securement sleeve, inhibiting movement of the medical tube in a distal or proximal direction relative to the securement device. Moreover, bending the medical tube inside of the securement sleeve provides an advantage of better control over the bend in the tube, advantageously reducing potential for the medical tube to crimp and obstruct fluid flow when bent. Such slippage could detrimentally result in the drainage tube being pushed deeper into the patient than desired. In preferred implementations of this enhancement, the bent tube holder is rotationally mounted and rotatable to different radial positions relative to the attachment pad, permitting repositioning of a direction that a secured medical tube extends away from the securement sleeve and advantageously permitting such directional repositioning of the medical tube even after the securement device has been attached to the patient. With such a preferred implementation, the direction to which the medical tube extends may advantageously be repositioned based on patient experience and/or as convenient for different needs during different stages of a medical procedure.

In another enhancement, the securement device can include a compression retainer, which can be disposed to retain the securement sleeve in a compressed configuration with the securement sleeve under longitudinally-applied compression with the cross-sectional area of the tube passage in the securement portion in an expended configuration convenient for receipt and translation through the tube passage a medical tube. The compression retainer can be manipulated, preferably by complete disengagement from other portions of the securement device, to release the securement portion from the longitudinally-applied compression and consequently permit lengthening of the securement sleeve to contract the cross-sectional area of the tube passage in the securement portion to grip a medical tube and secure the medical tube to the securement device. In preferred implementations with this enhancement when the securement sleeve also includes the preferred implementation of the bent tube holder being rotatably mounted, and in an enhancement of a rotatably mounted bent tube holder, the bent tube holder is preferably rotatable about an extension member extending through a rotating member on which the bent tube holder is mounted, and the extension member is advantageously configured to be engaged with the compression retainer when the compression retainer is disposed to retain the securement sleeve in the compressed configuration.

In another enhancement, the securement device can include a proximal sleeve coupling structure, through which the securement sleeve is coupled to the attachment pad, in which flared proximal end material of the securement sleeve is sandwiched between first and second securement members, and preferably retained in the sandwiched configuration with adhesive between the first and second securement members. This enhancement advantageously provides a simple structure to couple the securement sleeve with the attachment pad and permits efficient manufacturing with few component parts to assemble.

In another enhancement, the securement device can include a distal collar assembly retaining a distal end portion of the securement sleeve. The distal collar assembly provides a convenient feature for use to manipulate the securement sleeve to apply or not apply compression to the securement sleeve to shorten or lengthen the securement sleeve and to correspondingly enlarge of contract the cross-sectional area in the tube passage in the securement portion of the securement sleeve. In preferred implementations of this enhancement when the securement device also includes the enhancement of the compression retainer, the distal collar can advantageously be configured to be engaged with the compression retainer when the compression retainer is disposed to retain the securement sleeve in the compressed configuration.

In another enhancement, the attachment pad includes an absorbent portion configured to absorb exudate during use of the securement device, for example to absorb blood, serous fluid, or other fluid types that may exude from a wound in the vicinity of the insertion location of the medical tube. The absorbent portion advantageously helps to keep the wound area around the inserted medical tube clean and helps prevent such exudate from degrading integrity of the attachment, for example through degradation of adhesive, of the attachment pad to the skin of the patient. In preferred implementations of this enhancement, the absorbent portion has an aperture through which the tube passage extends, advantageously providing that the absorbent portion will extend completely around the periphery of the medical tube, contributing to effective absorption of exudate that may seep from a wound around the periphery of the inserted medical tube.

A second aspect of this disclosure is directed to various medical drain securement products including a securement device of the first aspect. In some preferred implementations, a product includes a peelable backing adhered to an adhesive surface of the attachment pad, and which peelable backing is configured to be peeled from the adhesive surface to expose the adhesive surface for adherence of the attachment pad to the skin of a patient during use of the securement device. When the securement device includes an absorbent portion, the peelable backing preferably covers a proximal face of the absorbent portion, which proximal face is disposed toward the patient when the attachment pad is attached to a patient. The peelable backing can advantageously cover and protect fluid communication surfaces of the proximal face, and which fluid communication surfaces can be exposed when the peelable backing is removed. Such a peelable backing can for example be provided in a single backing piece or in multiple backing pieces.

A third aspect of this disclosure is directed to kits including a securement device of the first aspect and at least one additional component useful in connection with a medical tube securement procedure. The securement device can be provided for example in a product of the second aspect or not in such a product. In some preferred implementations of the third aspect, the kit includes a medical tube, which may be a drainage tube or other medical tube, configured to be used with the securement device, for example with an outer cross-section size and profile for which the securement device is designed to receive and secure. This advantageously reduces a possibility that a medical practitioner might attempt to secure a medical tube outside of the design parameters for which the securement device is designed to be used.

A fourth aspect of this disclosure is directed to methods of securing a medical tube to a patient with a securement device having a variable-length securement sleeve and a tube passage through the securement sleeve to receive a medical tube for securement, wherein the securement sleeve includes a securement portion and in the securement portion a cross-sectional area of the tube passage transverse to a longitudinal path of the tube passage expands as the securement sleeve is shortened and contracts as the securement sleeve is lengthened and the length of the securement sleeve is adjustable to expand the cross-sectional area to receive the medical tube for translation through the tube passage and to contract the cross-sectional area to grip the medical tube in the tube passage in the securement portion to secure the medical tube to the securement device, and wherein the method comprises:

with a medical tube extending through the tube passage and into the body of a patient, gripping the medical tube in the tube passage with the securement portion of the securement sleeve. In some preferred implementations, the securement device is according to the first aspect, and optionally is provided in a securement product of the second aspect and or in a kit of the third aspect. The securement device of the first aspect can advantageously provide significant flexibility for performance of various operations during a medical procedure.

A fifth aspect of this disclosure is directed to methods of making a securement device of the first aspect. Applicable design combinations of the securement device can provide significant operational capabilities for use of the securement device with relatively few assembled component parts, advantageously permitting relatively simple manufacturing operations to make securement devices of the first aspect. The method can also include preparation of a securement product of the second aspect with application of a peelable backing to the securement device.

A number of feature refinements and additional features may be used individually or in any combination within the subject matters of the aspects of this disclosure. As such, each of the features described in the description below, including in the numbered example implementation combinations and the appended claims, and/or illustrated in the drawings, may be but are not required to be, used with any other feature or combination of features of any of the aspects of this disclosure.

DETAILED DESCRIPTION

Figure 1:
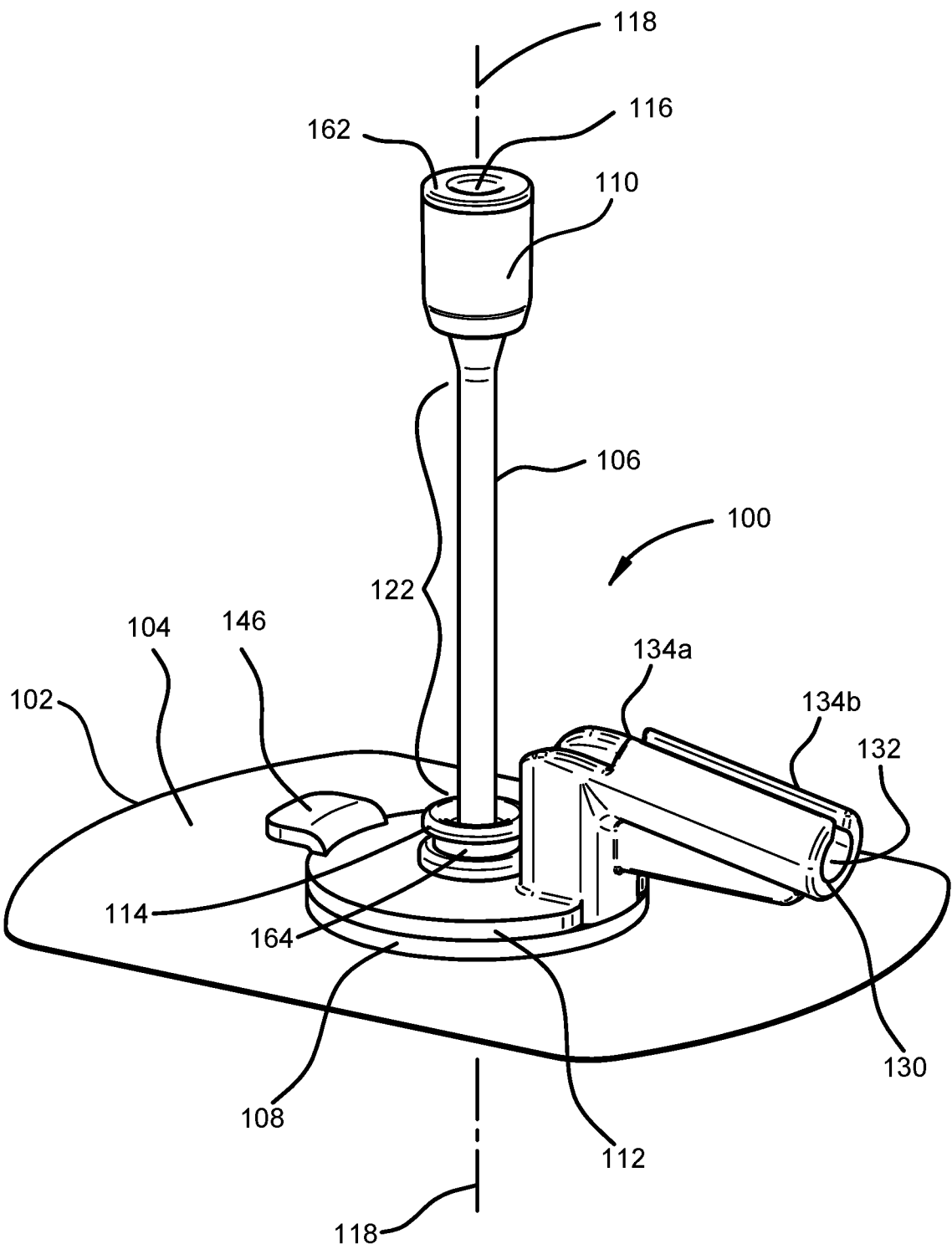
FIG. 1 is a perspective view of an example embodiment of a medical tube securement device.

FIG. 1 shows an example embodiment of a securement device 100 to secure a medical tube inserted into a patient. As illustrated in FIG. 1, the securement device 100 includes an attachment pad 102 configured to interface with the surface of the skin of a patient for attachment of the securement device to the skin. The attachment pad 102 is preferably made of materials sufficiently flexible to conform to the topography of a patient's skin. The attachment pad 102 includes a distal side 104 that faces away from the patient's skin during use and a proximal side (not shown) opposite the distal side 104. The proximal side of the attachment pad 102 faces and is configured to contact the skin for attachment to a patient. As used herein, "proximal" refers to relative positioning toward the skin of a patient during use of the securement device 100 and "distal" refers to positioning away from the skin of the patient during use of the securement pad 100. In preferred implementations, the attachment pad 102 includes an adhesive layer with an adhesive surface exposed on the proximal side of the attachment pad through which the attachment pad 102 may be adhered to the skin of the patient during use. Although not preferred, the attachment pad 102 could be attached to the skin of a patient, or attachment to the skin could be aided by other securement means, for example by taping the attachment pad to skin with tape extending across the distal side 104 of the attachment pad 102 and with the tape adhered to the skin beyond the periphery of the attachment pad 102, or through the use of sutures.

The securement device 100 includes a securement sleeve 106 that is coupled to the attachment pad 104 adjacent a proximal end of the securement sleeve 106. In the example embodiment of the securement device 100 illustrated in FIG. 1, a coupling structure through which the securement sleeve 106 is coupled to the attachment pad 102 includes a flared proximal end portion of the securement sleeve disposed between and adhered to a first surface on the distal side 104 of the attachment pad 102 and an opposing second surface on a proximal side of a base member 108. In this example, the coupling structure includes adhesive disposed between the opposing surfaces of the attachment pad 102 and base member 108 adhering together the opposing surfaces and the intermediate flared proximal end portion of the securement sleeve 106 sandwiched between the opposing surfaces of the attachment pad 102 and the base member 108. The distal end of the securement sleeve 106 is coupled to and retained by a distal collar 110.

The securement device 100 also includes a rotating member 112 that is engaged with an extension portion 114 of the base member 108 that projects through an aperture in the rotatable member 112 and is rotatably retained in a circular groove track extending around the perimeter of the extension portion 114 of the base member 108.

The securement device 100 includes a tube passage 116 extending in a longitudinal direction through the distal collar 110, the securement sleeve 106, the base member 108, and the attachment pad 102. The tube passage 116 has a proximal end open on the proximal side of the attachment pad 102 and a distal end open on a distal end of the distal collar 110. As illustrated in FIG. 1, the tube passage 116 has a longitudinal axis 118 extending in the longitudinal direction of the tube passage between the proximal end of the tube passage 116 and the distal end of the tube passage 116.

The securement sleeve 106 includes a securement portion 122 in which a medical tube extending through the tube passage 116 can be gripped by the securement sleeve 106 to secure the medical tube to the securement device 100 during use. During use, the securement device 100 can be attached to the skin of a patient and the medical tube can be disposed through the tube passage 116 and into the body of the patient, and the medical tube with the desired positioning in the patient can be secured to the securement device 100 by the securement portion 122 of the securement sleeve 106 to retain the medical tube in a fixed position relative to securement device 100 and relative to the patient to which the securement device 100 is attached.

Figure 2:
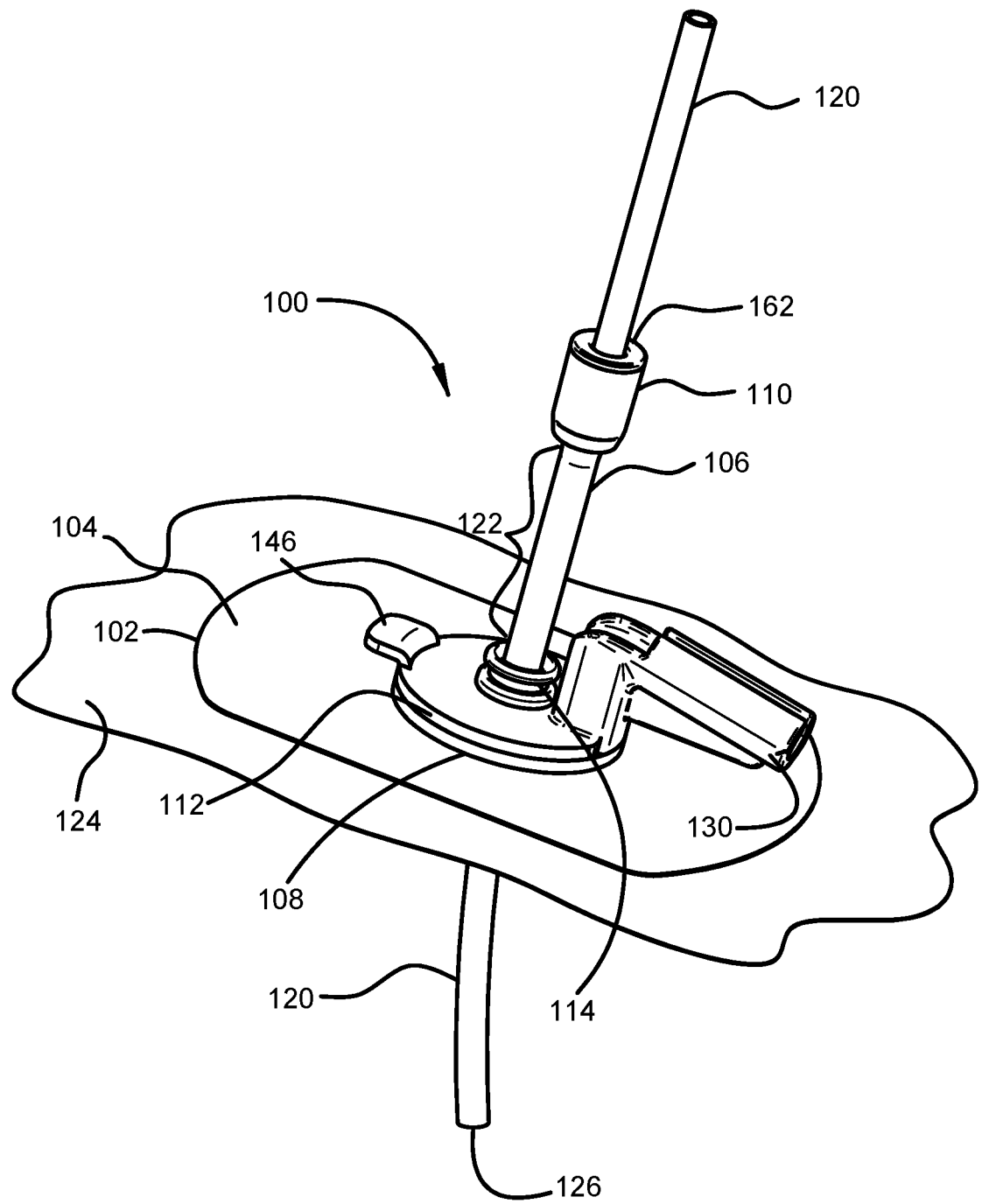
FIG. 2 is a perspective view of the medical tube securement device of FIG. 1 shown attached to skin of a patient and with a medical tube secured to the medical tube securement device.

FIG. 2 illustrates an example of the securement device 100 in use attached to skin 124 of a patient with a medical tube 120 extending through the tube passage 116 and with a proximal end 126 of the medical tube 120 disposed at a desired location in the body of the patient. The medical tube 120 held in place by securement to the securement device 100 by the securement sleeve 106 gripping the medical tube 120 in the tube passage 116 in the securement portion 122.

With continued reference to FIGS. 1 and 2, unlike the proximal end of the securement sleeve 106 which is in a fixed position relative to the base member 108 and the attachment pad 102, the distal end of the securement sleeve 106 is not in a fixed position relative to the base member 108 and the attachment pad 102. The securement sleeve 106 will be of a flexible construction, and the position of the distal end of the securement sleeve 106 relative to the base member 108 and the attachment pad 102 may be varied, for example by bending the securement sleeve 106 intermediately between the base member 108 and the distal collar 110. As will be appreciated, when the securement sleeve 106 is bent, the tube passage 116 and the longitudinal axis 118 of the tube passage 116 through the securement sleeve 106 will also be bent within the bent portion of the securement sleeve 106. As will also be appreciated, when the securement sleeve 106 is bent the medical tube 120 will be bent within the bent portion of the securement sleeve 106 when the medical tube 120 is disposed through the tube passage 116 as illustrated in FIG. 2.

The securement sleeve 106 of the securement device 100 illustrated in FIGS. 1 and 2 has a variable-length property, wherein the longitudinal length of the securement sleeve 106 between the proximal and distal ends of the securement sleeve 106 varies depending upon whether and to what extent the securement sleeve is subjected to longitudinally-applied force. For example, the securement sleeve 106 may be subjected to a longitudinally-applied compressive force by pushing the distal collar 110 toward the base member 108 and the attachment pad 102 to reduce the length of the securement sleeve 106, and the securement sleeve 106 may be subjected to a longitudinally-applied tensile force by pulling the distal collar 110 away from the base member 108 and the attachment pad 102 to increase the length of the securement sleeve 106. The magnitude of such a longitudinally-applied force will affect the magnitude by which the length of the securement sleeve 106 is decreased, in the case of longitudinally-applied compressive force, or increased, in the case of longitudinally-applied tensile force.

The securement portion 122 is a longitudinal portion of the securement sleeve 106 that lengthens and shortens with changes in longitudinally-applied force to which the securement sleeve 106, and correspondingly to which the securement portion 122, is subjected. The cross-sectional area of the tube passage 116, transverse to the longitudinal path of the tube passage along the longitudinal axis 118, expands as the securement sleeve 106 is shortened and contracts as the securement sleeve 106 is lengthened. As will be appreciated, when the securement sleeve 106 is shortened by longitudinally-applied compression, the length of the securement portion 122 is correspondingly shortened and the cross-sectional area of the tube passage expands, and a medical tube having an outside cross-section small enough to fit through the expanded cross-sectional area of the tube passage 116 may be inserted through the tube passage 116 in the securement portion 122. If the outside cross-section of the medical tube has a maximum cross-dimension (e.g., outer diameter of a circular tube cross-section) that is larger than a corresponding maximum cross-dimension of the tube passage 116 when the securement sleeve 106 is in a relaxed state (under no longitudinally-applied compression or tension) then when the longitudinally-applied compression is released with a medical tube disposed through the tube passage the inside wall surfaces of the securement portion 122 will grip the medical tube within the tube passage to secure the medical tube to the securement sleeve 106.

The securement portion 122 of the securement sleeve 106 represents a longitudinal portion of the securement sleeve 106 in which the cross-sectional area of the tube passage 116 in the securement sleeve may be varied by reducing the length of the securement sleeve 106 to permit insertion of a medical tube through an enlarged cross-sectional area of the tube passage 116 and then increasing the length of the securement sleeve 106 to reduce the cross-sectional area of the tube passage to grip and hold the medical tube. As will be appreciated, the securement portion 122 may make up varying longitudinal portions of the securement sleeve 106 depending upon the particular configuration of the securement sleeve 106, including materials of construction, construction geometry and the coupling structures with which the proximal end and the distal end of the securement sleeve 106 are engaged. For example, portions of the securement sleeve 106 in close proximity to coupling structures may be prevented by engagement with those coupling structures from sufficiently contracting in cross-section to grip a medical tube disposed through the tube passage 116. Likewise, the longitudinal length of such end portions unavailable to grip a medical tube may depend upon the particular size (e.g., outside diameter) of the medical tube to be gripped within the securement sleeve 106. As will also be appreciated, the securement portion 122 may not necessarily have a uniformly-sized cross-sectional area of the tube passage 116 at all longitudinal points within the securement portion 122. For example, when the securement sleeve 106 is in a state of longitudinally-applied compression, the cross-sectional area of the tube passage 116 may be somewhat larger, or bulged, near a longitudinal midpoint of the securement portion 122 relative to the tube passage 116 closer to the proximal and distal ends of the securement portion 122 where the cross-sectional area of the tube passage 116 may be more affected by coupling structures with which the securement sleeve 106 is engaged. Similarly, when the securement sleeve 106 is in a state of longitudinally-applied tension, the cross-sectional area of the tube passage 116 may be somewhat smaller near a longitudinal midpoint of the securement portion 122 than closer to the proximal and distal ends of the securement portion 122 where the cross-sectional area of the tube passage 116 may be more affected by coupling structures with which the securement sleeve 106 is engaged. As a consequence of possible variations in the cross-sectional area of the tube passage 116 through the securement portion 122, when in a compressed state with an enlarged cross-section, the tube passage may have a minimum cross-sectional area at one or more longitudinal points in the securement portion 122 that define a minimum insertion cross-section for receipt of a medical tube inserted through the securement portion 122. In some implementations, with the securement portion 122 in a compressed state to receive insertion of a medical tube, the minimum insertion cross-section may be defined by the cross-sectional area of the tube passage 116 adjacent proximal and/or distal coupling structures.

Figure 3:
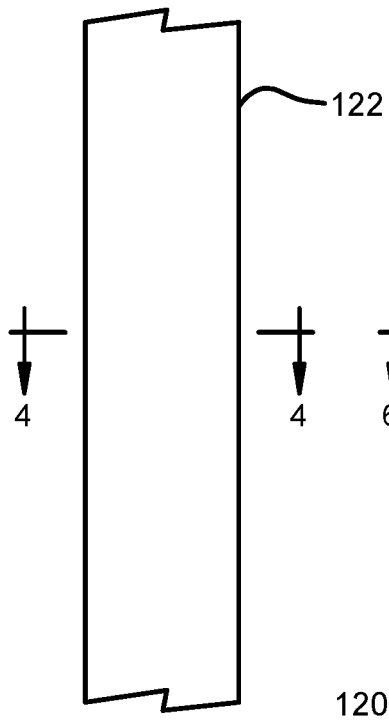
FIG. 3 is a partial side view of part of a securement portion of the securement sleeve of the medical tube securement device of FIG. 1, with the securement portion in a relaxed state.
Figure 5:
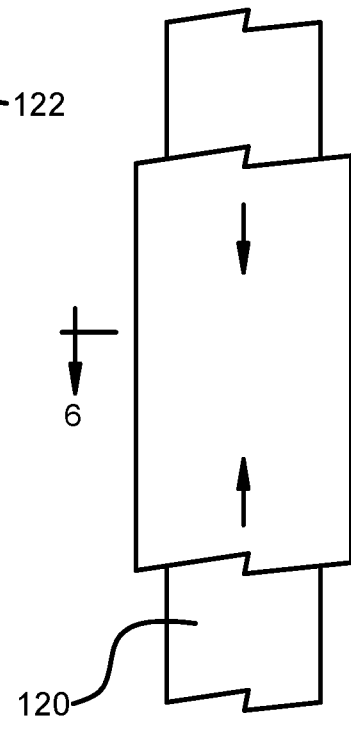
FIG. 5 is a partial side view of the part of the securement portion shown in FIG. 3, but with the securement portion in a compressed state and with a medical tube received through the securement portion and prior to securement to the medical tube securement device of FIG. 1.
Figure 7:
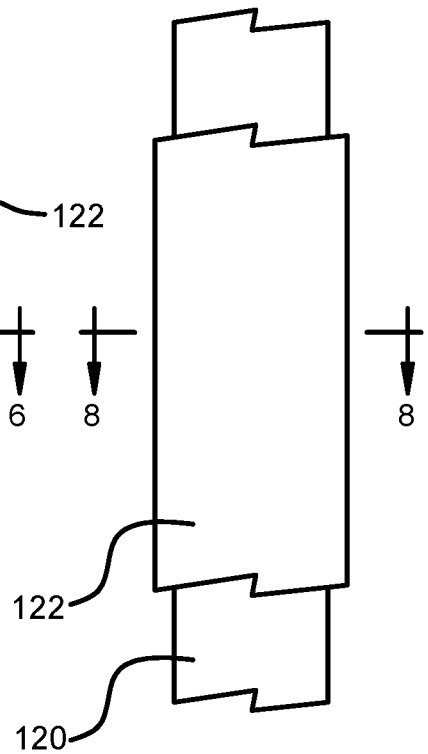
FIG. 7 is a partial side view of part of the part of the securement portion shown in FIG. 3, but with the securement portion relaxed from the compressed state of FIG. 5 to grip a medical tube received through the securement portion.
Figure 4:
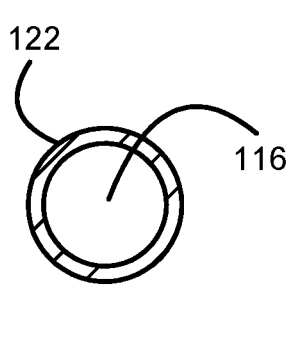
FIG. 4 is a sectional view of the part of the securement portion shown in FIG. 3.
Figure 6:
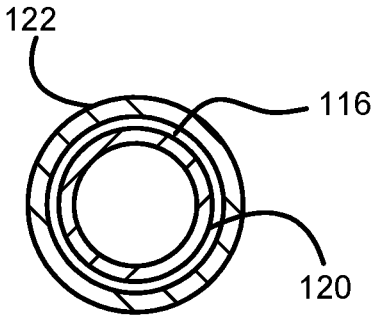
FIG. 6 is a sectional view of the part of the securement portion FIG. 5 with a received medical tube.
Figure 8:
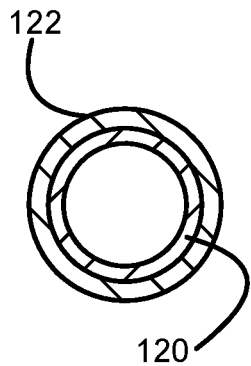
FIG. 8 is a sectional view of the part of the securement portion shown in FIG. 7 gripping a medical tube.

Reference is now made to FIGS. 3-8, together with FIGS. 1-2, to further discuss features of the securement portion 122 of the securement sleeve 106 of the securement device 100 illustrated in FIGS. 1 and 2. FIGS. 3, 5 and 7 each shows a longitudinal part of the securement portion 122, but illustrated in different states having different sizes for the cross-sectional area of the tube passage 116 through the securement portion 122. FIGS. 4, 6 and 8 are corresponding sectional views of the securement portion 122 illustrated in FIGS. 3, 5 and 7, respectively, taken transverse to the longitudinal direction of the tube passage 116. FIGS. 3, 5 and 7 show differences in the cross-sectional area of the tube passage 116 in the different illustrated states. FIGS. 3 and 4 illustrate the securement portion 122 alone, with the securement portion 122 in a relaxed state with no longitudinally-applied force, and in the relaxed state the cross-sectional area of the tube passage 116 is too small to receive for securement a medical tube of a size for which the securement portion 122 is designed to secure to the securement device 100. FIGS. 5 and 6 illustrate the securement portion 122 in a compressed state with the securement portion 122 subjected to longitudinally-applied compressive force, illustrated by the arrows shown in FIG. 5. In the compressed state of FIGS. 5 and 6, the cross-sectional area of the tube passage 116 is expanded relative to the relaxed state illustrated in FIGS. 3 and 4. FIGS. 5 and 6 show the medical tube 120 received through the tube passage 116 in the securement portion 122, and illustrate that in this compressed state the outer cross-section of the medical tube 120 is smaller than the cross-sectional area of the tube passage 116. FIGS. 7 and 8 then illustrate the securement portion 122 with the medical tube 120 disposed through the tube passage 116 after the longitudinally-applied compression of FIGS. 5 and 6 has been released, permitting the securement portion 122 to relax sufficiently to grip the medical tube 120 in the tube passage 116, for securement of the medical tube 120 to the securement device 100. As will be appreciated, the medical tube 120 illustrated in FIGS. 7 and 8 can be released from being gripped by the securement portion 122 to permit the medical tube 120 to be repositioned relative to the securement portion 122 or to be removed entirely from the securement portion 122. In this way, a medical tube inserted into a patient and held by the securement device 100 may be repositioned within the patient's body or removed and replaced with a different medical tube. The new or repositioned medical tube may then be secured to the securement device 100 by again releasing the securement portion 122 of longitudinally-applied compression to permit the securement sleeve 106 to relax and grip the new or repositioned medical tube. In other situations, after release of the medical tube 120 from securement, the securement device 100 can be removed from the patient without removing the medical tube from the patient, and a new securement device 100 can then be attached to the patient, for example if attachment of the prior securement device 100 to the patient becomes compromised, or to clean the wound and/or replace wound dressings. In still other situations, both the medical tube 120 and the securement device 100 may be replaced with a new medical tube and a new securement device 100.

Figure 9:
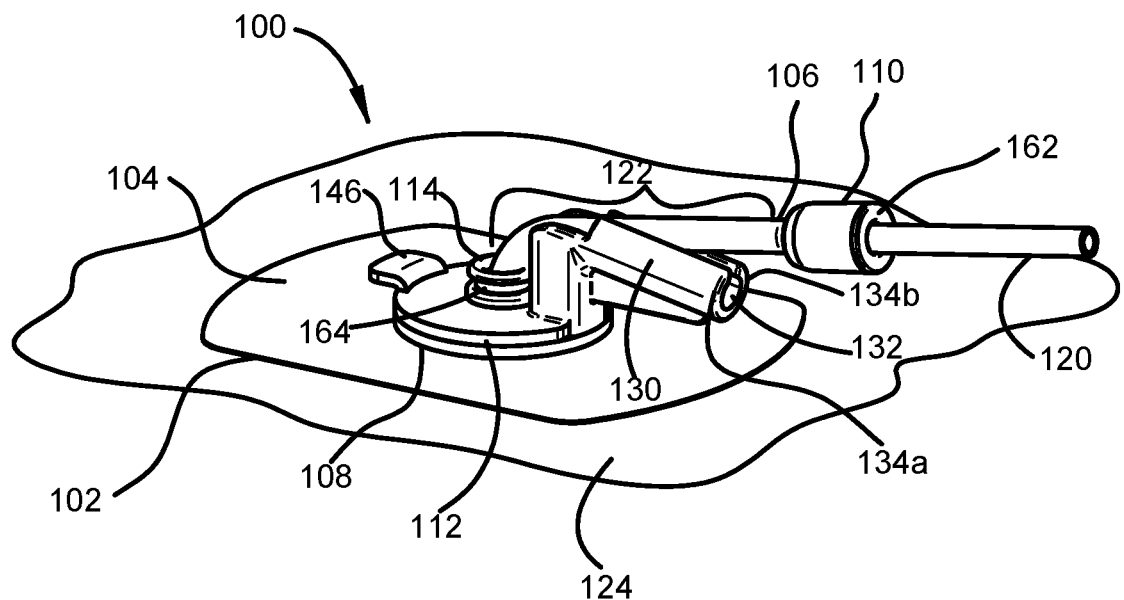
FIG. 9 is a perspective view of the medical tube securement device of FIG. 1 shown attached to skin of a patient with a medical tube secured in the securement sleeve and with the securement sleeve being configured into a bent configuration.
Figure 10:
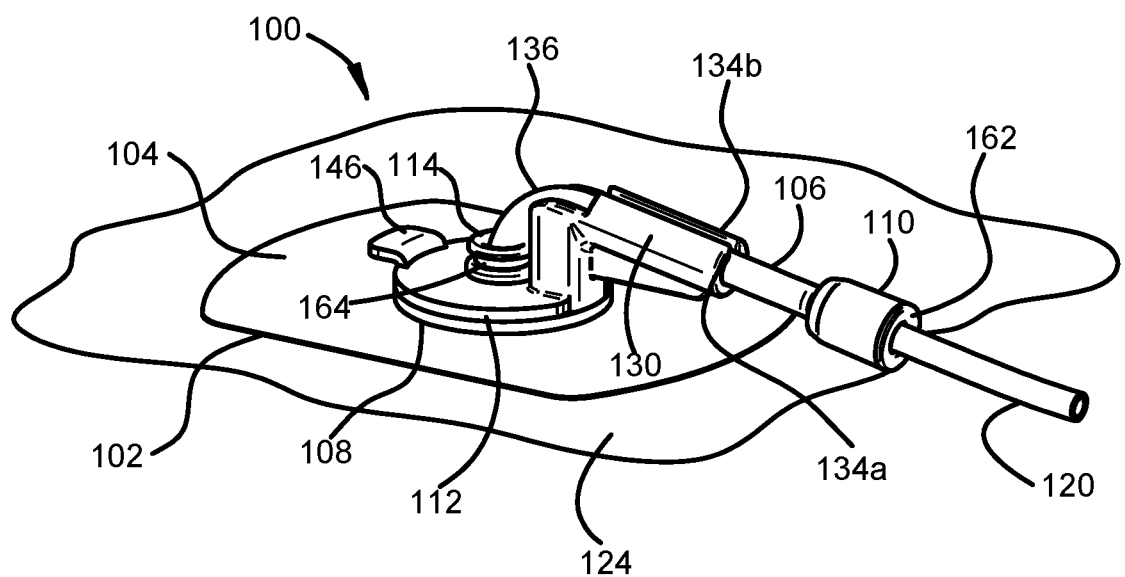
FIG. 10 is a perspective view of the medical tube securement device of FIG. 1 shown attached to skin of a patient with a medical tube secured in the securement sleeve and with the securement sleeve retained in a bent configuration.

Reference is now made primarily to FIGS. 9 and 10, together with FIGS. 1-8. FIGS. 9 and 10 show the securement device 100 of FIG. 1 attached to the skin 124 of a patient during use and with the medical tube 120 disposed through the securement sleeve 106 and into the body of the patient. The securement device 100 includes a bent sleeve holder 130, which in the illustrated embodiment of the securement device 100 includes a retaining channel 132 configured to selectively receive and hold a longitudinal portion of the securement sleeve 106 to retain the securement sleeve 106 in a bent configuration in which a distal portion of the securement sleeve 106 is biased toward the skin 124, and toward an attachment plane of the attachment pad 102. As referred to herein, an attachment plane of the attachment pad 102 refers to a plane perpendicular to the longitudinal axis 118 of the tube passage 116 at a point where the tube passage 116 is open at a proximal side of the attachment pad 102. The holder 130 includes flexible tabs 134a,b that are sufficiently flexible to permit the securement sleeve 106 to be pushed into the channel 132, with the flexible tabs 134a,b temporarily deflecting to the sides as the securement sleeve 106 is pushed into the retaining channel 132. FIG. 9 shows the securement sleeve 106 being pushed into the retaining channel 132 with the flexible tabs 134a,b deflecting to the sides as the securement sleeve 106 is pushed into the retaining channel 132. The flexible tabs 134a,b should have sufficient rigidity, however, to retain the received portion of the securement sleeve 106 in the retaining channel 132 to retain the securement sleeve 106 in a bent configuration, as illustrated in FIG. 10. As illustrated in FIG. 10, in the bent configuration the securement sleeve 106 has a bend 136 through a portion of the securement sleeve 106 between the proximal end of the securement sleeve 106 and the retaining channel 132. In the bent configuration, a portion of the securement sleeve 106 distal of the bend 136 is biased toward the skin 124 and an attachment plane of the attachment pad 102, and with a relatively small standoff of the securement sleeve 106 from the attachment pad 102 and the surrounding skin 124 of the patient. The securement sleeve 106 may be released from the bent configuration by pulling the securement sleeve 106 out of the retaining channel 132, with the flexible tabs 134a,b temporarily deflecting as the securement sleeve 106 is removed from the retaining channel 132. As illustrated in FIG. 10, in the bent configuration the securement sleeve 106 is bent through an angle of approximately 90°, although as will be appreciated the bent sleeve holder 130 could be configured to retain the securement sleeve 106 with a bend through an angle greater than or less than 90°. The tabs 134a,b may be made of any material of construction, for example metallic or polymeric materials of construction, and preferably of a polymeric material (and more preferably a thermoplastic elastomer), providing a desired level of both flexibility to elastically deform and permit the securement sleeve 106 to be pushed into and removed from the channel 132 and to otherwise hold the securement sleeve 106 in the bent configuration when the received portion of the securement sleeve 106 is received in the receiving channel 132. The configuration illustrated in FIGS. 9 and 10 illustrate one preferred implementation in which the bent sleeve holder 130 receives and retains a longitudinal portion of the securement portion 122 of the securement sleeve 106, and with the bend 136 also including a longitudinal portion of the securement portion 122.

One advantage of the securement device 100 configured to selectively retain the securement sleeve in the bent configuration as illustrated in FIG. 10 is that after positioning the medical tube as desired in the patient's body and after securing the medical tube 120 to the securement device 100 with the medical tube 120 gripped by the securement portion 122 of the securement sleeve 106, then the medical tube 120 may be conveniently positioned and held in the bent configuration with a relatively close standoff from the patient, significantly reducing possibility for accidental or unintended interactions with the securement sleeve 106 or the medical tube 120 by the patient or a medical practitioner. Additionally, the design provides advantageous flexibility to easily release the securement sleeve 106 from the bent configuration to permit manipulation of the securement sleeve 106 to release the medical tube 120 to permit the medical tube 120 to be repositioned, to permit removal of the medical tube 120 from the patient, or to permit removal and replacement of the securement device 100 without repositioning or removal of the medical tube. Another advantage is that in the bent configuration, the bend 136 provides additional resistance to release of the securement portion 122 from gripping the medical tube 120 if the patient or medical practitioner should intentionally or inadvertently push on the distal collar 110 to impart a longitudinally-applied compression to the securement sleeve 106 that could otherwise lead to an undesired release of the medical tube 120 from securement by the securement sleeve 106 and an undesired movement of the medical tube 120. The bend 136 helps to resist an inadvertent release of the medical tube 120 from being secured by the securement sleeve 106. Additionally, the structure defining the channel 132 will provide some resistance to enlargement of the cross-section of the securement sleeve 106 within the channel to permit enlargement of the cross-sectional area of the tube passage 116 within the securement portion 122 to release the medical tube from securement. The bent configuration also advantageously provides additional resistance to someone pushing on the medical tube 120 toward the distal collar 110 or pulling the medical tube 120 away from the distal collar 110 with sufficient force to overcome the force with which the medical tube 120 is held by the securement sleeve 106. As will be appreciated from the illustration of FIG. 10, if someone, such as the patient, pushes the medical tube 120 toward the distal collar 110 or pulls the medical tube 120 away from the distal collar 110, the bend 136 provides additional resistance to movement of the medical tube 120 through the securement sleeve 106.

Reference is now made to FIGS. 11-15, together with FIGS. 1-10, in relation to describing a rotational feature of the securement device 100 permitting the bent sleeve holder 130 to be rotated to and positioned at various radial positions relative to the attachment pad 102. In the example securement device 100 illustrated in FIGS. 1 and 2, the bent sleeve holder 130 is mounted on the rotating member 112, which is selectively rotatable relative to the base member 108 to permit the bent sleeve holder 130 to be positioned at different radial positions relative to the attachment pad 102. More particularly, the rotating member 112 has an aperture 140 (seen best in FIG. 12) through which the extension portion 114 of the base member 108 extends and the rotating member 112 is received in and rotatably retained by a circular groove track extending around the perimeter of the extension portion 114, whereby the extension portion 114 acts as an axle about which the rotating member 112 is rotatable to radially position the bent sleeve holder 130. As will be appreciated, in the example configuration of the securement device 100 the longitudinal axis 118 of the tube passage 116 through the attachment pad 102 is coaxial with an aperture through the extension portion 114 about which the rotating member 112 rotates, and accordingly the different radial positions at which the bent sleeve holder 130 may be positioned are radially spaced about the longitudinal axis 118 of the tube passage 116 through the attachment pad 102.

Figure 11:
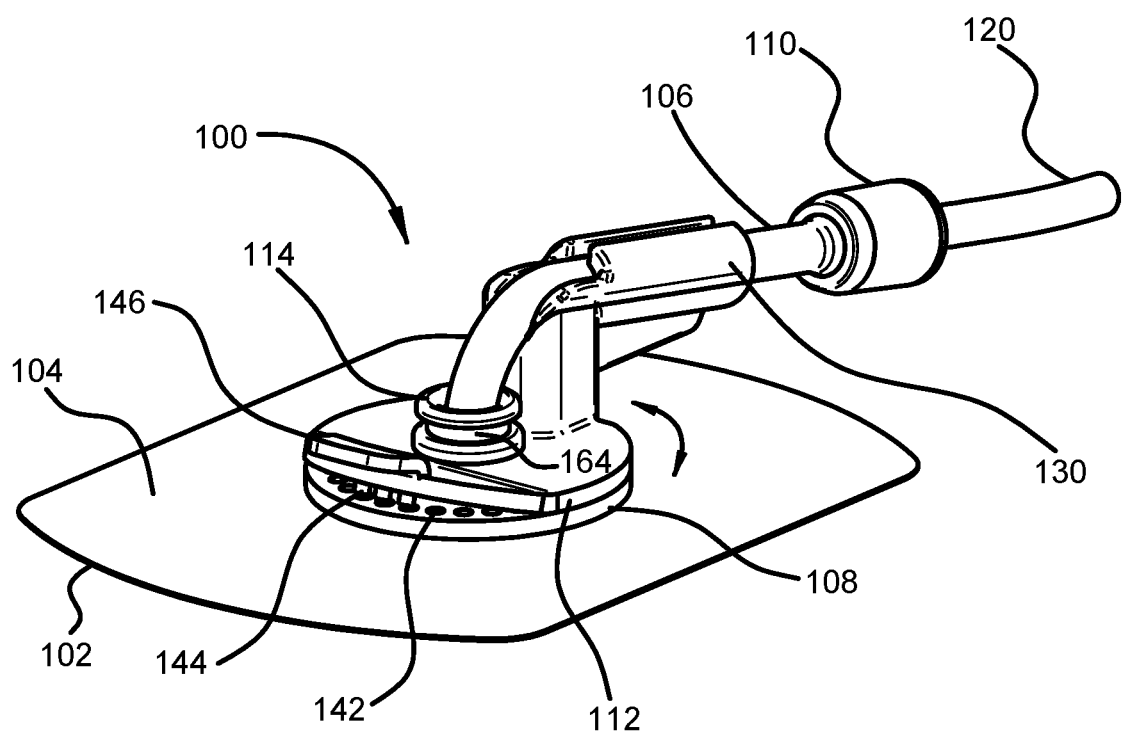
FIG. 11 is a perspective view of the medical tube securement device of FIG. 1 shown attached to skin of a patient with a medical tube secured in the securement sleeve and illustrating features of a rotational lock structure.
Figure 12:
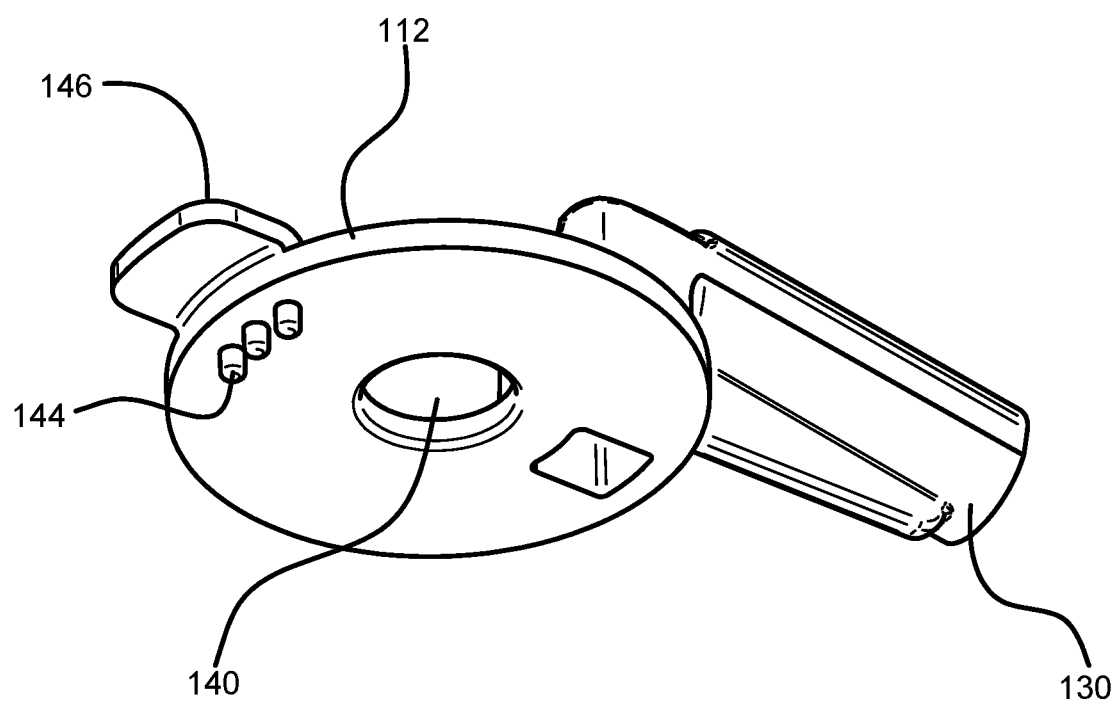
FIG. 12 is a perspective view of a portion of the medical tube securement device of FIG. 1 including a rotating member and a bent tube holder supported on the rotating member.
Figure 13:
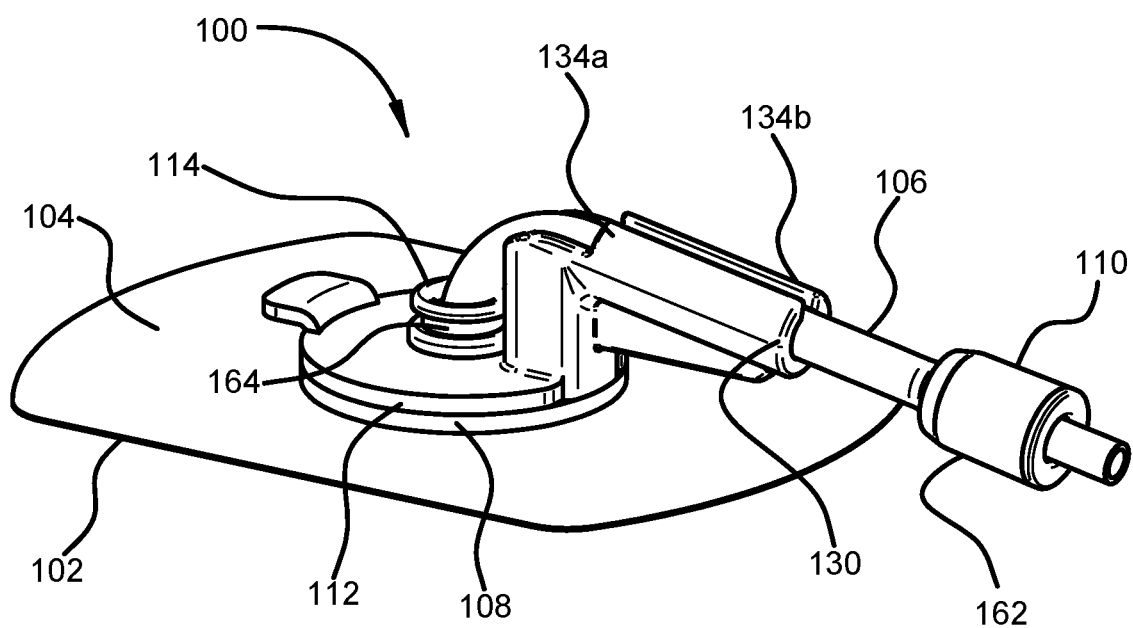
FIG. 13 is a perspective view of the medical tube securement device of FIG. 1 showing an example radial positioning of a bent sleeve holder.
Figure 14:
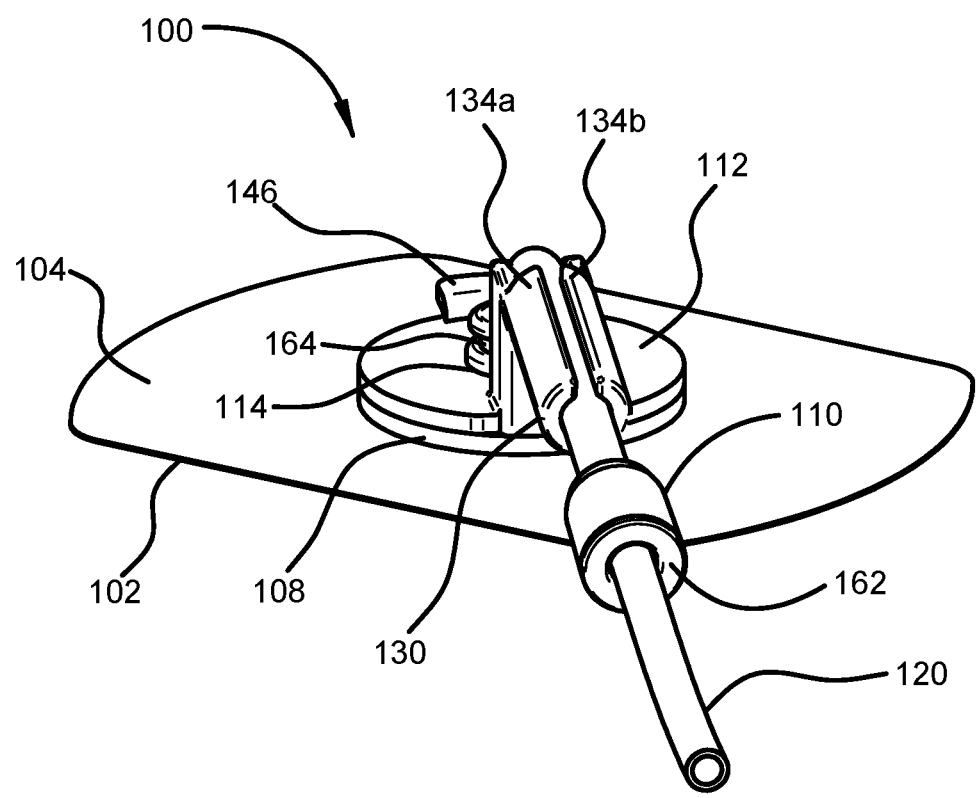
FIG. 14 is a perspective view of the medical tube securement device of FIG. 1 showing another example radial positioning of a bent sleeve holder.
Figure 15:
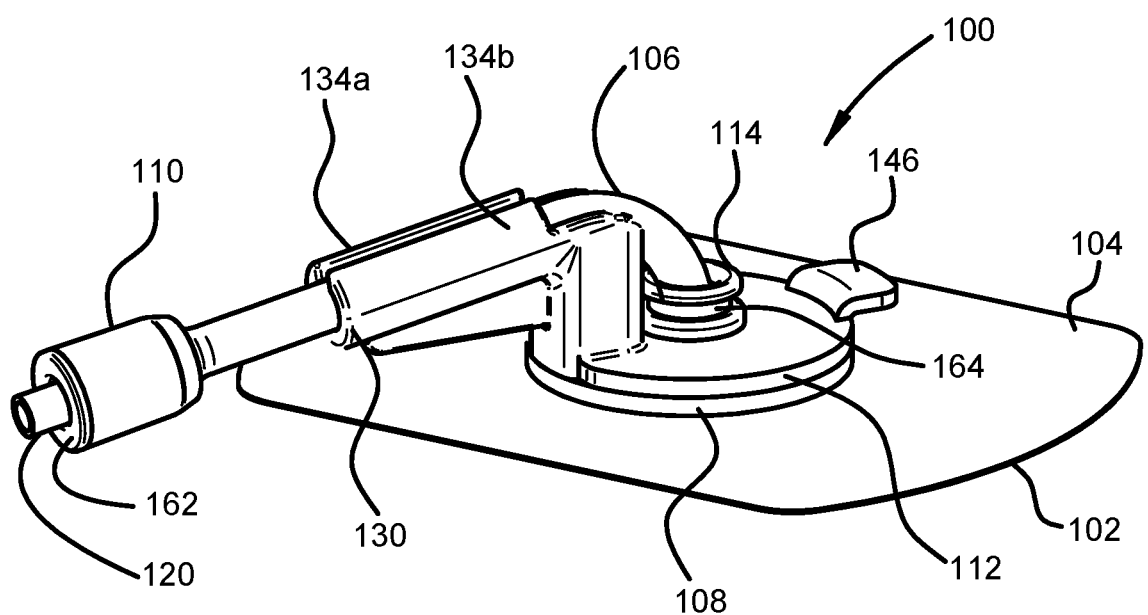
FIG. 15 is a perspective view of the medical tube securement device of FIG. 1 showing yet another example radial positioning of a bent sleeve holder.

The securement device 100 includes a radial positioning lock to selectively lock the bent sleeve holder 130 at different radial positions. The rotatable member 112 and the base member 108 have complementary interlocking lock structures that can be selectively engaged to lock the radial position of the rotating member 112 at different radial positions. In the illustrated example of the securement device 100 the base member 108 has a plurality of recesses 142 spaced radially around the base member 108 and the rotating member 112 has a plurality of projections 144, and the projections 144 are configured to be receivable in the recesses 142 to lock the rotating member 112 in a fixed radial position relative to the base member 108. As illustrated in FIG. 11, the rotating member 112 is made of a material that is suitably flexible to permit a portion of the rotating member 112 to be elastically deformed to disengage the projections 144 from the recesses 142 to permit the rotating member 112 to be rotated relative to the base member 108, as indicated by the rotational arrow in FIG. 11. After rotating the rotating member 112 to a desired radial position, the elastically deformable portion of the rotating member 112 may be manipulated to engage the projections 144 with corresponding ones of the recesses 142 to lock the rotating member 112 at that radial position. A manipulation tab 146 on the rotating member 112 may be used by a person to manipulate the elastically deformable portion of the rotating member 112 to engage and disengage the projections 144 from the recesses 142 and to rotate the rotating member 112 relative to the base member 108 and to then engage the projections 144 with corresponding ones of the recesses 142 at a new radial position. Preferably, the recesses 142 are continued around the complete periphery of the rotating member 112, and the rotating member 112 and the bent sleeve holder 130 are rotatable fully 360° about the longitudinal axis 118 as an axis of rotation to permit the rotating member 112 and the bent sleeve holder 130 to be positioned at various radial positions about the axis of rotation. FIGS. 13-15 illustrate the rotating member 112 and the bent sleeve holder 130 positioned at 3 different example radial positions relative to the attachment pad 102.

In an enhancement, the rotating member 112 and the bent sleeve holder 130 may be provided in a single-piece construction, preferably a single molded piece (e.g., single injection molded piece) made of a single, uniform material of construction, typically a polymeric material, having properties suitable to provide desired properties for functioning of both the flexible tabs 134a,b and the elastically deformable portion of the rotating member 112. In some preferred implementations, such a material of construction for the rotating member 112 and the bent sleeve holder 130 has a hardness in a range of from 60 to 90 Shore A durometer.

A significant advantage in flexible utility of the securement device 100 is provided by the configuration permitting the bent sleeve holder 130 to be positioned at different radial positions relative to the attachment pad. The attachment pad may be positioned relative to a patient for best attachment of the securement device 100 to the patient without regard to the position of the bent sleeve holder 130 of the direction that a medical tube will project from the bent sleeve holder 130. The bent sleeve holder 130 may be positioned at the most advantageous radial positioning relative to the patient's body regardless of the attachment orientation of the attachment pad 102, for example to avoid unintended patient or medical personnel interactions with the medical tube 120 or the securement sleeve 106 or to keep the securement sleeve 106 and medical tube 120 positioned to avoid obstruction of areas on the patient to which medical access may be desired while the drainage tube 120 is secured to the securement device 100. Additionally, the radial position of the bent sleeve holder 130 and medical tube 120 may be adjusted as desired based on patient experience or changing medical access needs. As will be appreciated, if the bent sleeve retainer is radially repositioned while the medical tube 120 is retained in the retaining channel 132, the radial movement will tend to impart a torsional stress to the securement sleeve 106 and to the medical tube 120 gripped by the securement sleeve. As a consequence, it is preferred that prior to repositioning the radial position of the bent sleeve holder, the securement sleeve be removed from the retaining channel 132, so that the bent sleeve retainer can be radially repositioned without imparting such a torsional stress to the securement sleeve 106 or medical tube 120.

Figure 16:
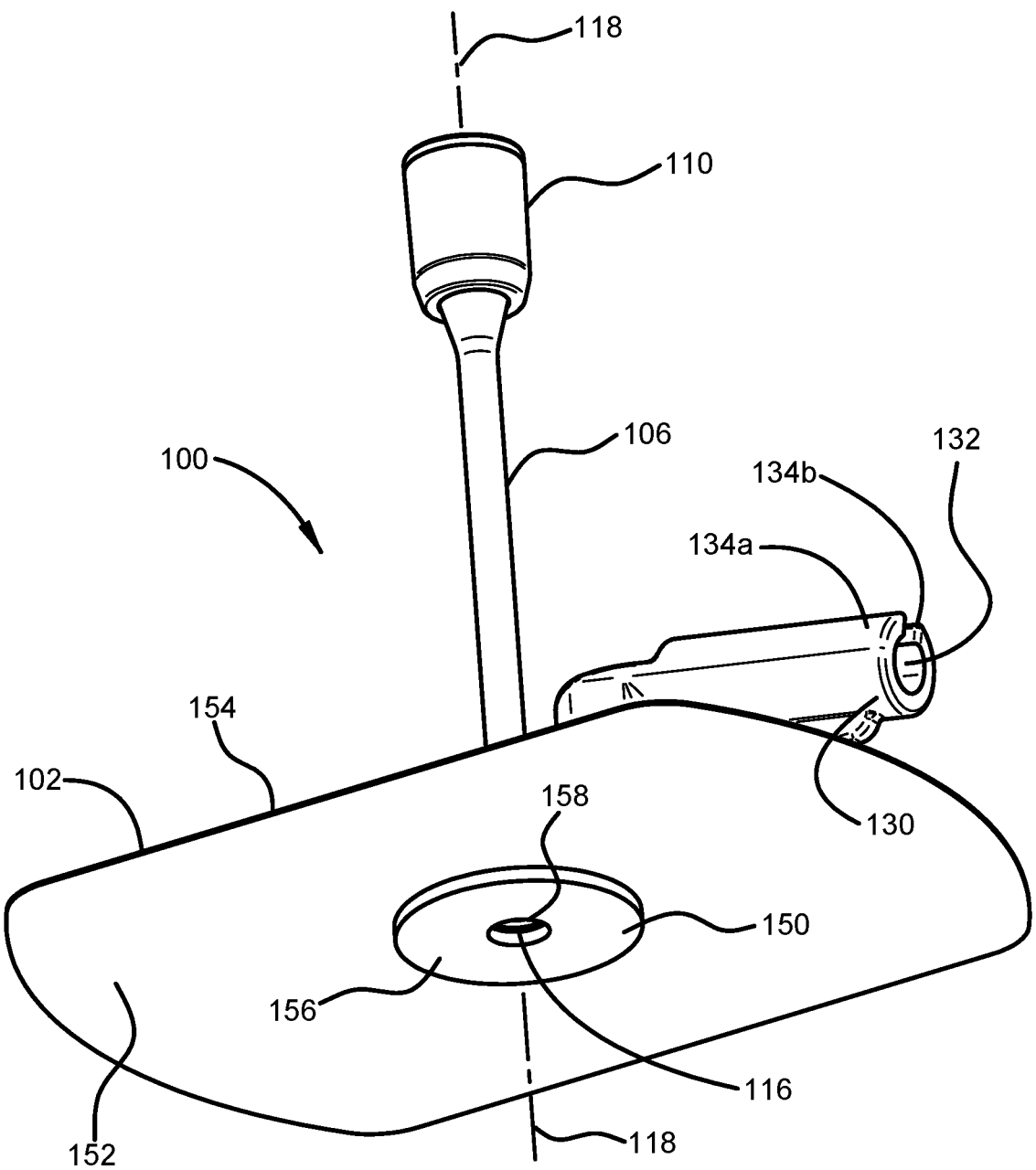
FIG. 16 is a perspective view of the medical tube securement device of FIG. 1 showing an absorbent portion of an attachment pad.

Reference is now made to FIG. 16, together with FIGS. 1-15, in relation to describing an absorbent feature of the securement device 100 to absorb exudate from a patient during use. As shown in FIG. 16, the attachment pad 102 of the example securement device 100 includes an absorbent portion, in the form of an absorbent pad 150, exposed on a proximal side 152 of the attachment pad 102 to provide absorbent capability to absorb exudate from a wound of a patient into which a secured medical tube extends during use of the securement device 100. In the example illustrated in FIG. 16, the absorbent pad 150 is attached, such as with adhesive, to a structural sheet 154 of the attachment pad 102. The absorbent pad 150 has a proximal face 156 configured to contact and interface with skin of the patient during use of the securement device 100. The absorbent pad 150 includes an aperture 158, which forms a part of the tube passage 116. The opening of the aperture 158 at the proximal face 156 of the absorbent pad 150 provides the proximal opening of the tube passage 116 in the example embodiment of the securement device 100 illustrated in FIGS. 1-16. In an alternative variation, the securement device 100 may be in the absence of (may not include) the absorbent pad 150, in which case an aperture of the structural sheet 154 would provide the proximal opening of the tube passage 116. The structural sheet 154 may be made of any suitable material or materials that impart a desired structural integrity to the attachment pad 102 and that are suitably flexible to conform to topography of a patient's skin to which the attachment pad 102 is to be attached. As will be appreciated, it may be desirable at times to remove the securement device 100 from the patient without removing the medical tube from the patient, and then replace the removed securement device 100 with a new securement device, for example a new securement device 100 with a fresh absorption pad 150. Some example materials of construction for the structural sheet include flexible plastic and fabric materials.

Also illustrated in FIG. 16 is the longitudinal axis 118 of the tube passage 116, which for the portion of the tube passage 116 that extends through the attachment pad 102 is substantially perpendicular to a proximal face on the proximal side 152 of the attachment pad 102 adjacent a location where proximal end of the tube passage 116 is open on the proximal side 152 of the attachment pad 102. In the illustrated example of the securement device 100, the proximal end of the tube passage 116 opens through and is perpendicular to the proximal face 156 of the absorbent pad 150. As will be appreciated, although the longitudinal axis 118 may bend through the securement sleeve 106 when the securement sleeve 106 is bent, such as illustrated in any of FIGS. 9-15, the longitudinal axis 118 will typically be in a substantially straight line for the portion of the tube passage 116 through the attachment pad 102, even when the securement sleeve 106 is bent distal of the attachment pad 102, such as illustrated in FIGS. 9-15. As will also be appreciated, a medical tube (e.g., the medical tube 120) exiting the body of a patient will typically enter the proximal end of the tube passage 116 substantially perpendicular to the skin of the patient in that vicinity.

Including the absorbent pad 150 in the example embodiment of the securement device 100 advantageously permits absorption of exudate migrating out of a wound of the patient into which the medical tube is inserted. Such absorption of exudate advantageously helps to maintain the area around the wound in a clean state and also helps to inhibit exudate from seeping between the structural sheet 154 and skin of the patient, which could loosen and adhesive bond between the attachment pad 102 and the skin of the patient. The attachment pad 102 may comprise absorbent material and may have a desired absorbent capacity, for example as disclosed elsewhere herein. The absorbent pad 150 may beneficially contain an antimicrobial agent. Examples of some possible antimicrobial agents for use with an absorbent portion of the attachment pad 102 or elsewhere in connection with a securement device or product or kit including a securement device, include polymyxin, bacitracin, mupirocin, silver, chlorhexidine gluconate and similar derivatives, or iodine and its derivatives. More generally, the attachment pad 102 may include an antimicrobial agent, which may include for example any of the example microbial agents described for the absorbent pad. Such an antimicrobial agent may be included in the absorbent pad, adhesive layer and/or another other layer or feature of the attachment pad 102, and preferably when the attachment pad 102 includes an antimicrobial agent, the antimicrobial agent is contained in one or more portions of the attachment pad 102 that is open to fluid communication with the patient (e.g., the skin or wound of the patient) for contact or release of the antimicrobial agent to contact the patient (e.g., for the antimicrobial to contact the skin or wound of the patient).

Figure 17:
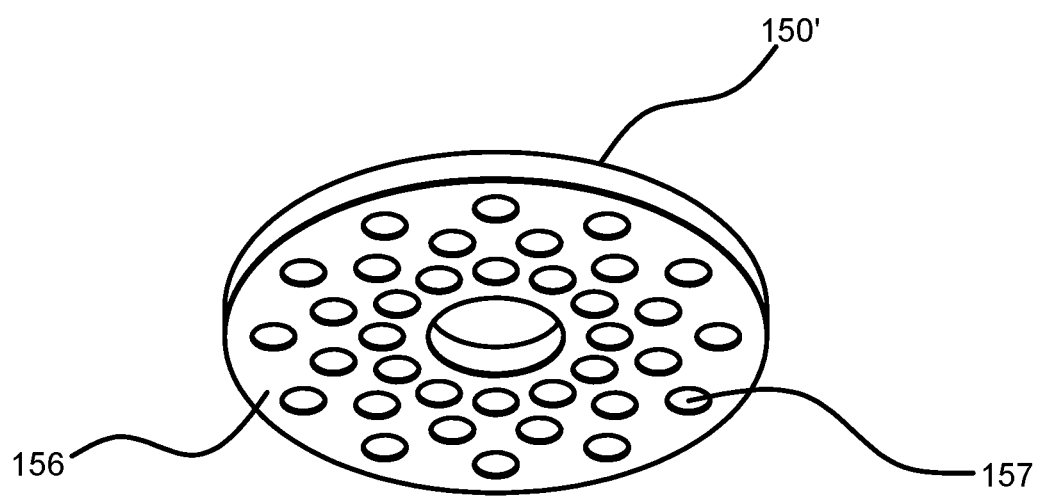
FIG. 17 is a perspective view of an alternative configuration of an absorbent portion of an attachment pad.

In the embodiment of the securement device 100 as illustrated in FIG. 16, a proximal surface of the structural sheet 154 completely surrounds a periphery of the absorbent pad 150. In some preferred implementations of the securement device 100, the proximal side 152 of the attachment pad 102 includes a layer of adhesive covering the portion of the proximal surface of the structural sheet 154 that surrounds the periphery of the absorbent pad 150. Such an adhesive layer may thus be exposed on the proximal side 152 of the attachment pad and may advantageously be used to adhere the attachment pad 102 to the skin of the patient completely around the periphery of the absorbent pad 150. The absorbent pad 150 may or may not include adhesive on the proximal surface 156. In some preferred implementations, the proximal face 156 of the absorbent pad 150 is substantially in the absence of adhesive, which could otherwise interfere with effective absorption of exudate coming from an adjacent a wound. However, in some alternative implementations the attachment pad 102 may include adhesive over at least a portion of the proximal face 156 to adhere the adsorbent pad 150 to skin of the patient, however in such alternative implementations the adhesive preferably does not cover the entire proximal face 156 and a portion of the proximal face 156 is uncovered by adhesive to provide better fluid communication at those locations for exudate to permeate into the absorbent material of the absorbent pad 150. For example such adhesive on the proximal face 156 may be in a perforated layer of adhesive, with areas of the perforations comprising a portion of the proximal face 156 being free of adhesive. FIG. 17 illustrates an example of a variation of an absorbent pad 150' on which a perforated layer of adhesive is disposed over a portion of the proximal face, through which areas of perforations 157 are free of adhesive to provide enhanced fluid communication through those areas. As will be appreciated, other configurations for adhesive on the proximal face 156 could be provided other than the perforated configuration illustrated in FIG. 17, provided that adhesive coverage over the proximal face 156 is sufficient to provide a desired level of adherence of the proximal face 156 to skin of the patient while not unduly inhibiting fluid communication into absorbent material of the absorbent pad 150.

The absorbent pad 150 can be sized to provide more or less absorbent material to alter the absorbent capacity of the absorbent pad 150, for example through changes in the thickness of the absorbent pad or the areal proportion of the proximal side 152 of the attachment pad 102 that is provided by the proximal face 156 of the absorbent pad 150. As will be appreciated, the more of the proximal side 152 that is made up by the proximal face 156, the smaller will be the exposed proximal surface of the structural sheet 154. In one alternative implementation, the proximal face 156 of the absorbent pad 150 can make up the entirety of the proximal side 152 of the attachment pad 102, and in such an alternative implementation, the proximal face 156 may include adhesive exposed at a portion of the proximal face to adhere the attachment pad 102 to the patient while other portions of the proximal face are in the absence of adhesive, for example with a perforated adhesive pattern as illustrated in FIG. 17 or as may be provided with other adhesive patterns on the proximal face 156. In an implementation where the proximal face 156 of the adhesive pad 150 makes up the entirety of the proximal side 152 of the attachment pad 102, the attachment pad 102 may still include the structural sheet 154 adhered to a distal face of the absorbent pad 150 to enhance durability of the attachment pad 102, to provide structural support to the absorbent pad 150 and/or to provide a protective cover over a distal side of the absorbent pad 150. The structural sheet 154 may be made of any material, for example a polymeric material, used to make wound bandages.

Figure 18:
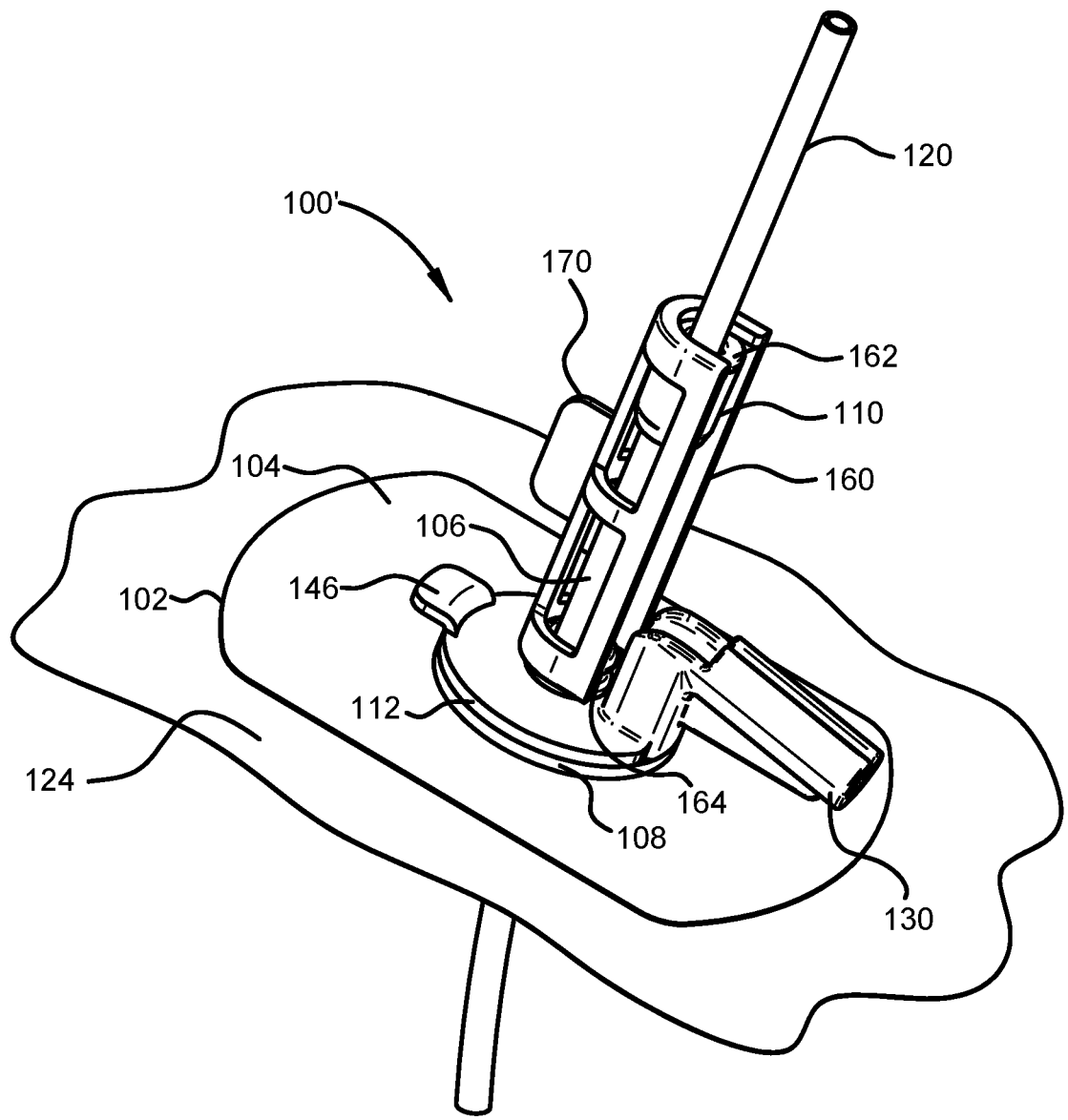
FIG. 18 is a perspective view of a variation of the medical tube securement device of FIG. 1 including a compression retainer, and shown attached to skin of a patient with a medical tube received through the securement sleeve.
Figure 19:
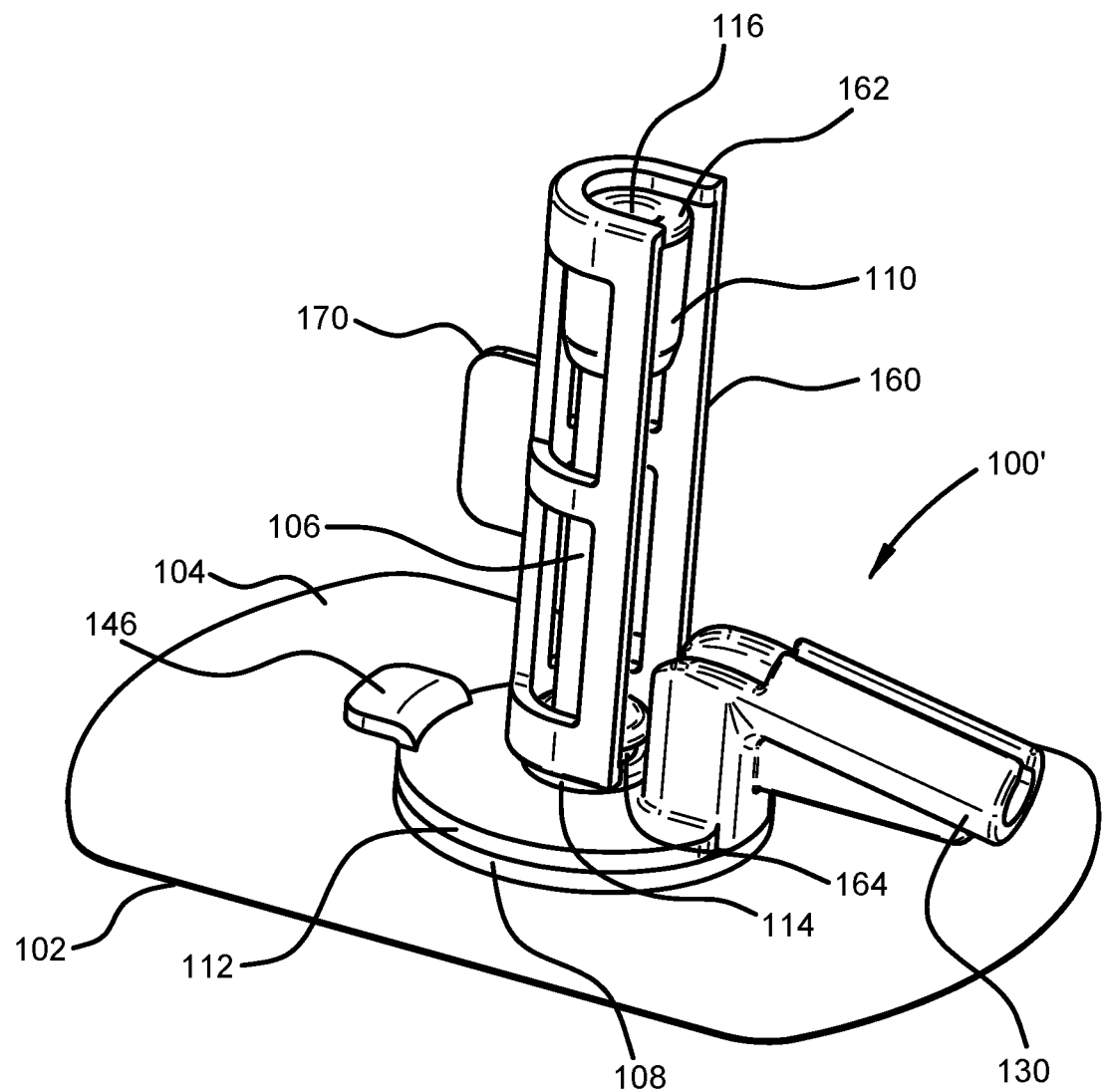
FIG. 19 is a perspective view of the variation of the medical tube securement device of FIG. 18.
Figure 20:
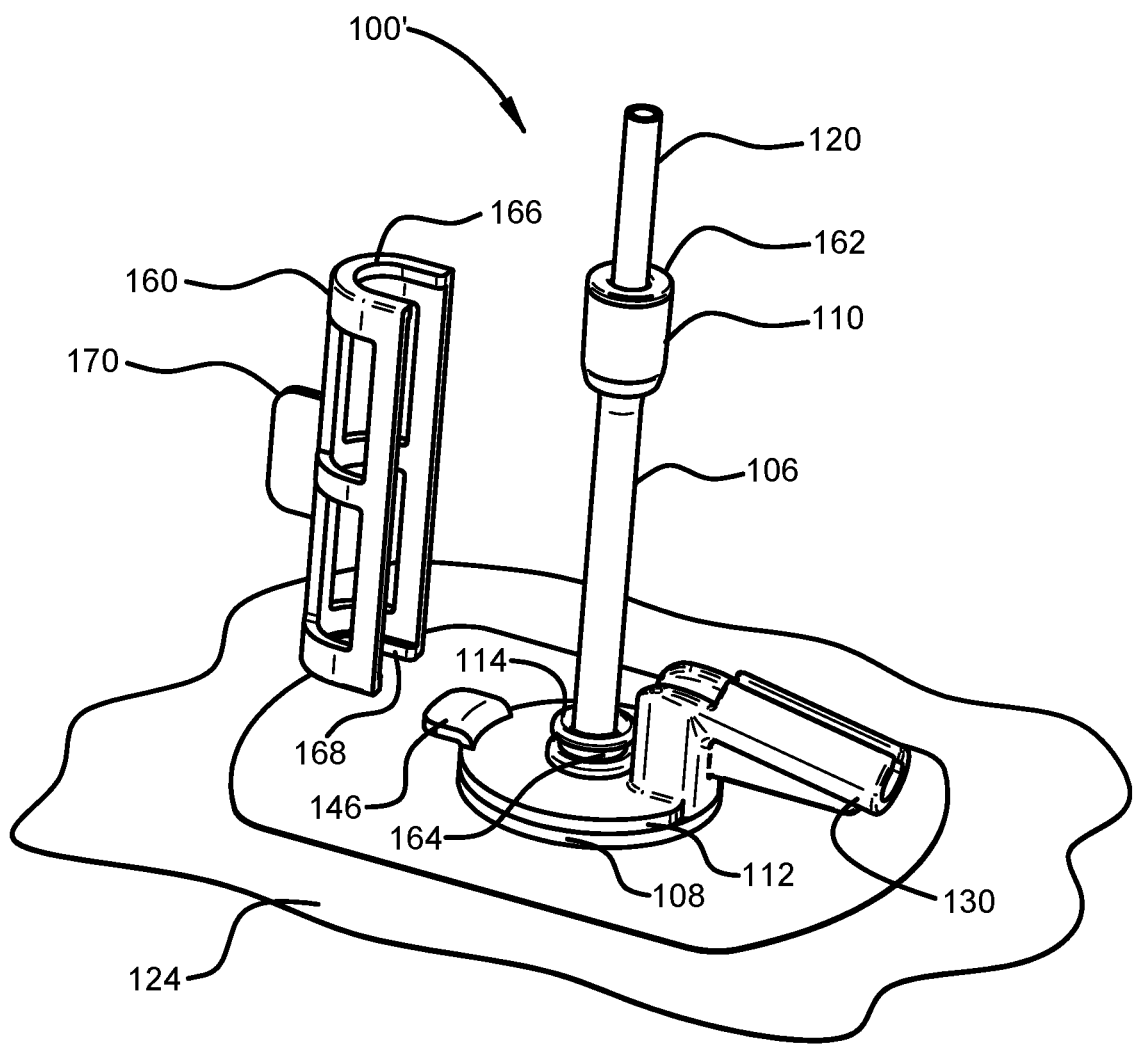
FIG. 20 is a perspective view of the variation of the medical tube securement tube of FIG. 18, shown after removal of the compression retainer to grip the medical tube in the securement sleeve, and with the medical tube securement device shown attached to skin of a patient and with a medical tube received through the securement sleeve.

Reference is now made to FIGS. 18-20, together with FIGS. 1-17, in relation to an example embodiment of a securement device including a compression retainer. FIGS. 18-20 show an example embodiment of a securement device 100', which has the same features and operational capabilities as the securement device 100 illustrated in FIGS. 1-17, but with the securement device 100' also including a compression retainer 160. FIG. 18 shows the compression retainer 160 disposed to retain the securement sleeve 106 in a compressed configuration with the cross-sectional area of the tube passage 116 in an enlarged configuration to receive insertion of a medical tube for positioning within the securement sleeve 106.

FIG. 18 shows the securement device 100' attached to the skin 124 of a patient through the attachment pad 102 and with the medical tube 120 disposed through the securement device 100' and into the body of the patient. In FIG. 19, the securement device 100' is illustrated with the compression retainer 160 disposed to retain the securement sleeve 106 in the compressed configuration ready to receive a medical tube for securement. In the compressed configuration as illustrated in FIGS. 18, the securement portion 122 of the securement sleeve 106 and the medical tube 120 may be configured for example as illustrated in FIGS. 5 and 6.

FIG. 20 shows the securement device 100' after the compression retainer 160 has been manipulated, through removal of the compression retainer 160 in the example embodiment of FIGS. 18-20, to release the securement sleeve 106, and consequently also the securement portion 122 of the securement sleeve 106, from the compressed configuration to permit the securement sleeve 106 to lengthen and with corresponding contraction of the cross-sectional area of the tube passage 116 in the securement portion 122 to grip the medical tube 120 in the tube passage 116. When the compression retainer 160 has been removed, as illustrated in FIG. 20, the securement portion 122 of the securement sleeve 106 and the medical tube 120 may be in a configuration, for example, as illustrated in FIGS. 7 and 8. As will be appreciated, other configurations for a compression retainer are possible, for example in which the securement sleeve 106 could be released from the compressed configuration without removal of the compression retainer from other components of the securement sleeve 100'. For example, a compression retainer could be pivotally-connected or slidably-connected to other components of the securement device 100' and being manipulable to release the securement sleeve 106 from the compressed configuration without disconnection of the compression retainer from the other assembled components of the securement device 100'. However, complete disengagement and removal of the compression retainer 160 as illustrated in FIG. 20 is preferred, to remove complications and obstructions that may otherwise be present if the compression retainer 160 is not fully removed from other remaining components of the securement device 100'.

As illustrated in FIGS. 18 and 19, when the compression retainer 160 is disposed to retain the securement sleeve 106, and the securement portion 122, in a compressed configuration, the compression retainer 160 has retaining projections 166 and 168 that engage, respectively, a top surface 162 of the distal collar 110 and a securement recess 164 on the extension portion 114 of the base member 108. The compression retainer 160 includes a handle tab 170 configured to be easily grasped by a medical practitioner to remove the compression retainer 160 to release the securement sleeve 106 from the compressed configuration.

As will be appreciated, if the securement device 100' is configured as shown in FIG. with the compression retainer 160 disengaged from the top surface 162 of the distal collar 110 and the securement recess 164 of the extension portion 114 of the base member 108, the distal collar 110 may be pushed toward the extension portion 114 to compress the securement sleeve 106 to the compressed configuration, and while holding the securement sleeve 106 in the compressed configuration the compression retainer 160 may be placed in position to engage the top surface 162 and the securement recess 164 to hold the securement sleeve 106 in the compressed configuration, for example to permit convenient repositioning or replacement of the medical tube 120 or removal and replacement of the securement device 100 without removal of the medical tube 120. As will also be appreciated, the securement device 100' may be initially provided in a product form with the compression retainer 160 preinstalled to retain the securement sleeve 106 in the compressed configuration until the securement device 100' is used to secure a medical tube. Alternatively, the securement device 100' may be initially provided in a product form with the compression retainer 160 not preinstalled to retain the securement sleeve 106 in the compressed configuration, and the compression retainer 160 may be installed as needed to hold the securement sleeve 106 in the compressed configuration while the medical tube is inserted into the securement sleeve 106 for positioning prior to gripping the medical tube with the securement portion 122 of the securement sleeve 106. Providing the securement device 100' in a product form with the compression retainer 160 preinstalled provides the benefit of not having to install the compression retainer 160 prior to insertion of a medical tube into the securement portion 122 of the securement sleeve 106. However, providing the securement device 100' in a product form with the compression retainer 160 not preinstalled to retain the securement sleeve 106 and the compressed configuration may provide a benefit of a longer shelf-life of the securement device 100' by not losing expansive capability of the securement sleeve 106 over long periods of storage with the securement sleeve held in a compressed configuration.

After use of a securement device, such as the securement device 100, is complete the securement device may be detached from the patient. Detachment may include application of an alcohol or other solvent around the edges of the attachment pad, such as with a swab or wipe, to degrade adhesive, permitting the adhesive pad to be more easily peeled away from the patient's skin. As portions of the attachment pad are peeled away from the skin, the solvent may continue to be applied around adhered areas of the attachment pad until all adhered portions of the attachment pad have been detached from the skin. Prior to detachment of the securement device, the securement sleeve may be manipulated to release the medical tube from securement and the medical tube removed from the patient and the securement sleeve. Alternatively, the securement device and the secured medical tube may be removed as a unit, with the medical tube gripped by the securement portion of the securement sleeve while the securement device is detached from the patient, and the proximal end of the medical tube may then be pulled out of the patient as the securement device is removed. When the medical tube remains secured to the securement device while the securement device is detached from a patient, the medical tube may or may not be retained in the bent configuration by a bent sleeve holder of the securement device. Retaining the medical tube in the bent configuration helps to prevent movement of the medical tube relative to the securement device as the securement device is detached. Alternatively, the medical tube may be released from the bent configuration prior to detachment of the securement device.

Reference is now made to FIGS. 21-32, together with FIGS. 1-17, in relation to further describing features of the example securement device 100 and an example method of making the example securement device 100.

Figure 21:
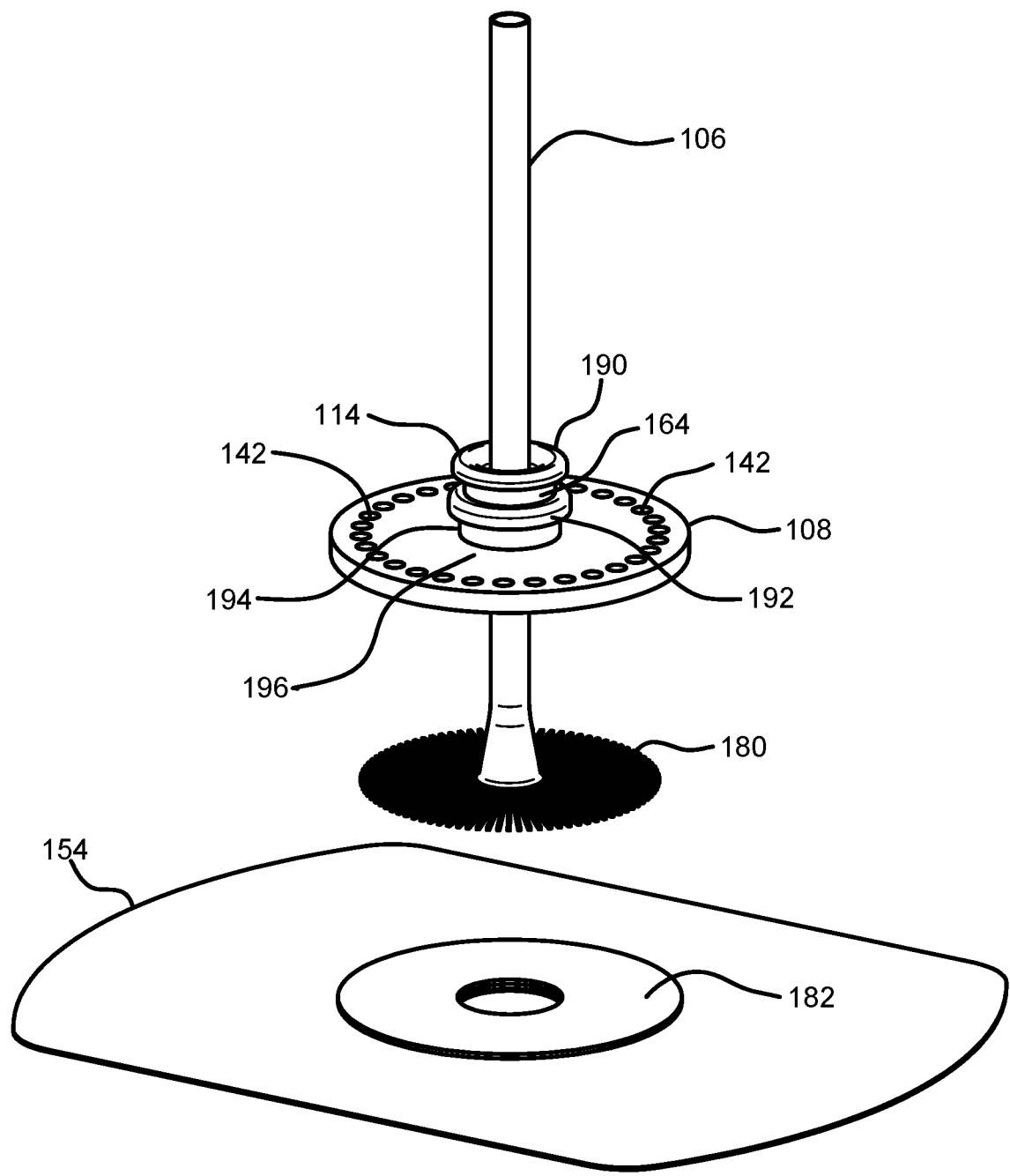
FIG. 21 illustrates relative positioning of some components for manufacture of an example medical tube securement device.

FIG. 21 shows components and their relative positioning for a coupling structure between the securement sleeve 106 and the structural sheet 154 for the attachment pad 102 for the securement device 100 of FIG. 1. As shown in FIG. 21, the securement sleeve 106 is disposed through an aperture through the base member 108 and with a proximal end portion 180 of the securement sleeve 106 disposed between a proximal side of the base member 108 and a distal side of the structural sheet 154. Disposed on the distal side of the structural sheet 154 is an adhesive layer 182 of pressure-sensitive adhesive. As will be appreciated, adhesive can also or alternatively be provided on the distal side of the structural sheet 154.

Figure 22:
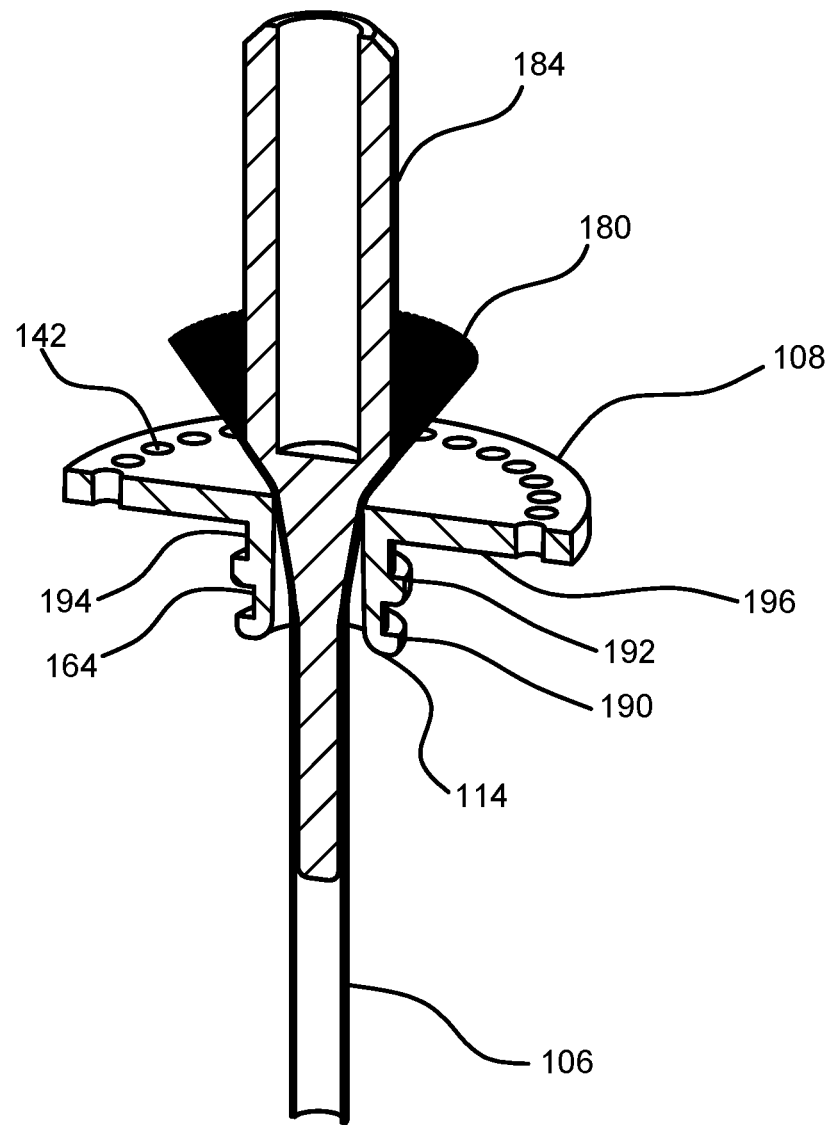
FIG. 22 illustrates an example of flaring a proximal end portion of the securement sleeve during manufacture of a medical tube securement device.
Figure 23:
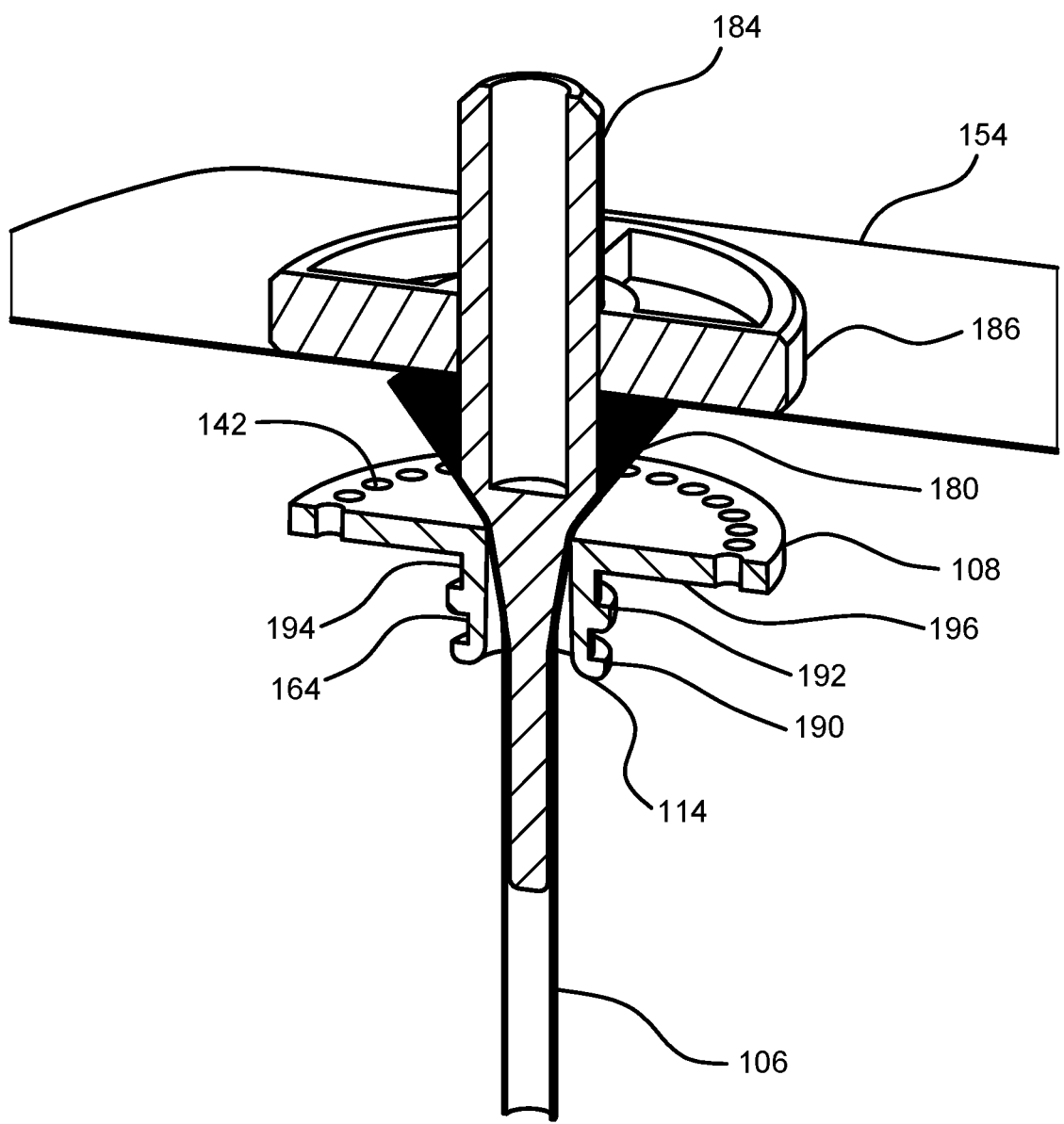
FIG. 23 illustrates an example of coupling a securement sleeve to a structural sheet for an attachment pad during manufacture of an example medical tube securement device.
Figure 24:
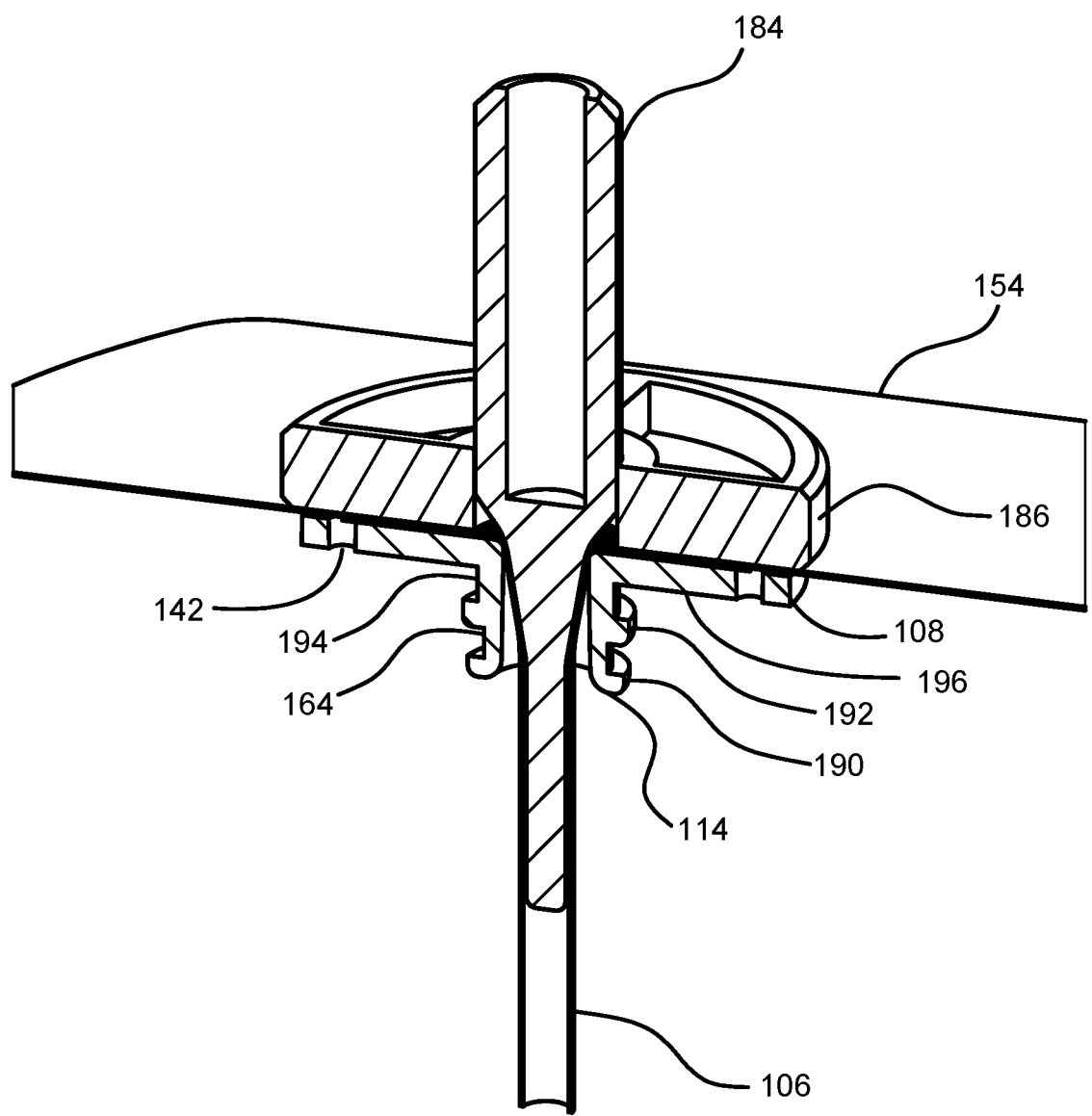
FIG. 24 further illustrates the example of coupling the securement sleeve to a structural sheet for an attachment pad during manufacture of an example.
Figure 25:
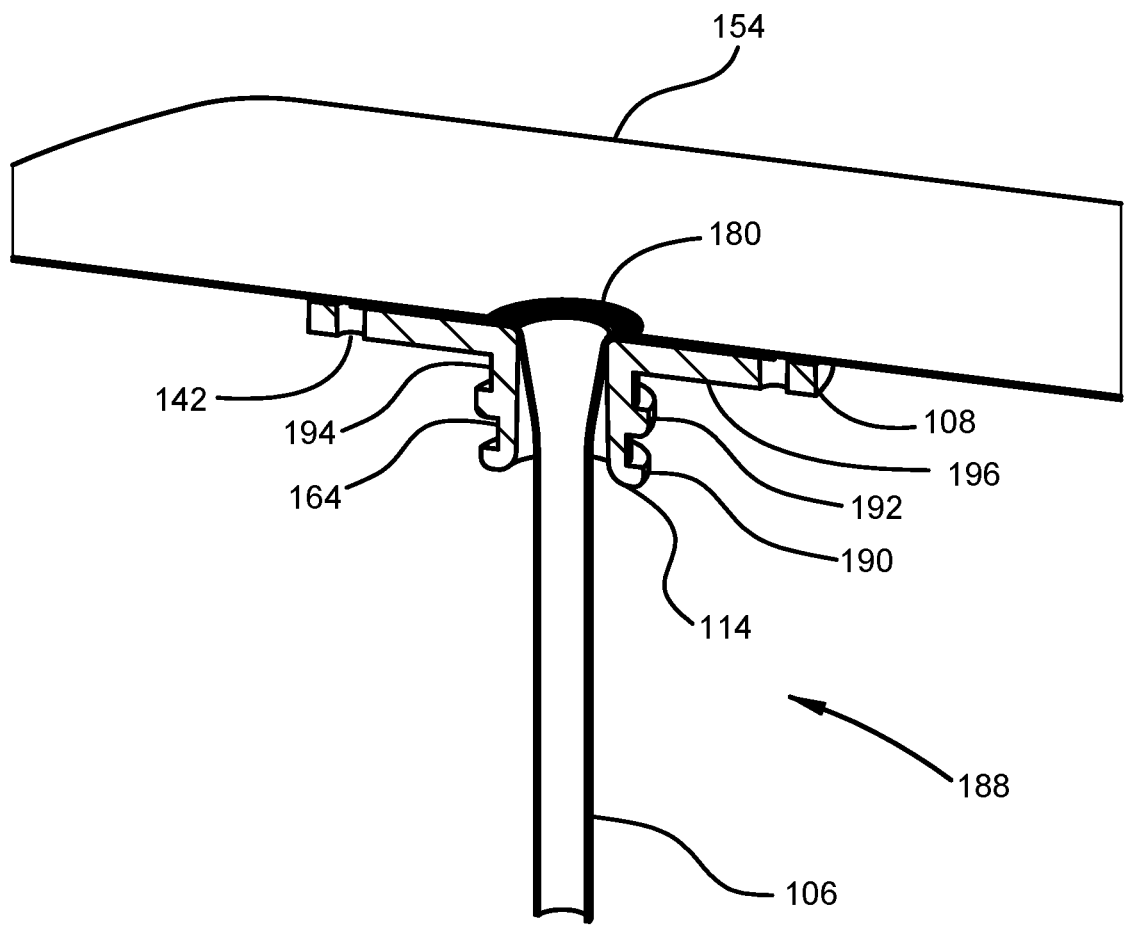
FIG. 25 shows a sectional view of an example of a first preliminary product form during manufacture of a medical tube securement device.
Figure 26:
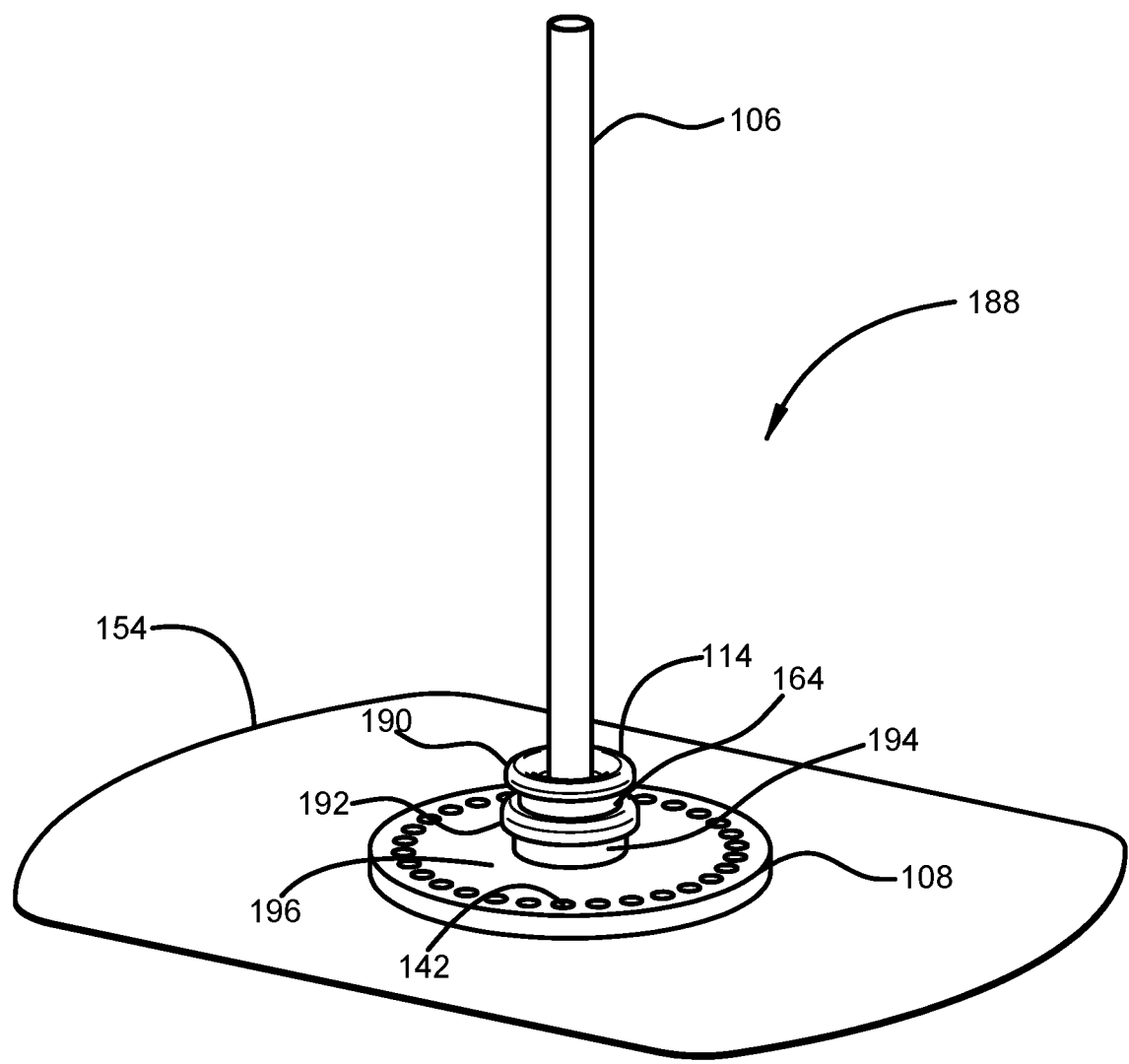
FIG. 26 shows a perspective view of the first preliminary product form shown in FIG. 25.

FIGS. 22-26 illustrate processing to couple together the base member 108, securement sleeve 106 and structural sheet 154. FIG. 22 illustrates the securement sleeve 106 disposed through the aperture of the base member 108 and with a flaring tool 184 inserted into a proximal end of the securement sleeve 106 to flare the proximal end portion 180 of the securement sleeve 106. FIG. 23 shows a compression ring tool 186 disposed over a mandrel portion at the top of the flaring tool 184 and with the compression ring tool 186 being advanced over the mandrel portion to press a distal side of the structural sheet 154 toward the proximal face of the base member 108 with the proximal end portion 180 of the securement sleeve 106 disposed between the proximal face of the base member 108 and the distal side of the structural sheet 154. As the compression ring tool 186 is advanced along the mandrel portion of the flaring tool 184 to advance the structural sheet 154 toward the base member 108, the distal side of the structural sheet 154 engages the proximal end portion 180 of the securement sleeve 106 and continues to flare the proximal end portion 180 to a 90° flare angle with the proximal end portion 180 flattened between the proximal face of the base member 108 and the distal side of the structural sheet 154 and in contact with the pressure sensitive adhesive of the adhesive layer 182 (not shown in FIG. 23, shown in FIG. 21). FIG. 24 shows the compression ring tool 186 fully advanced, and in the configuration shown in FIG. 24 the compression ring tool 186 is pressed toward the base member 108 with sufficient force to adhere the proximal face of the base member 108 to the distal side of the structural sheet 154 with the pressure sensitive adhesive, and with the flared proximal end portion 180 of the securement sleeve 106 sandwiched between the proximal face of the base member 108 and the distal side of the structural sheet 154 and held by the adhesive. FIGS. 25 and 26 show a resulting first preliminary product form 188 including the base member 108, securement sleeve 106 and structural sheet 154 after removal of the compression ring tool 186 and the flaring tool 184.

Figure 27:
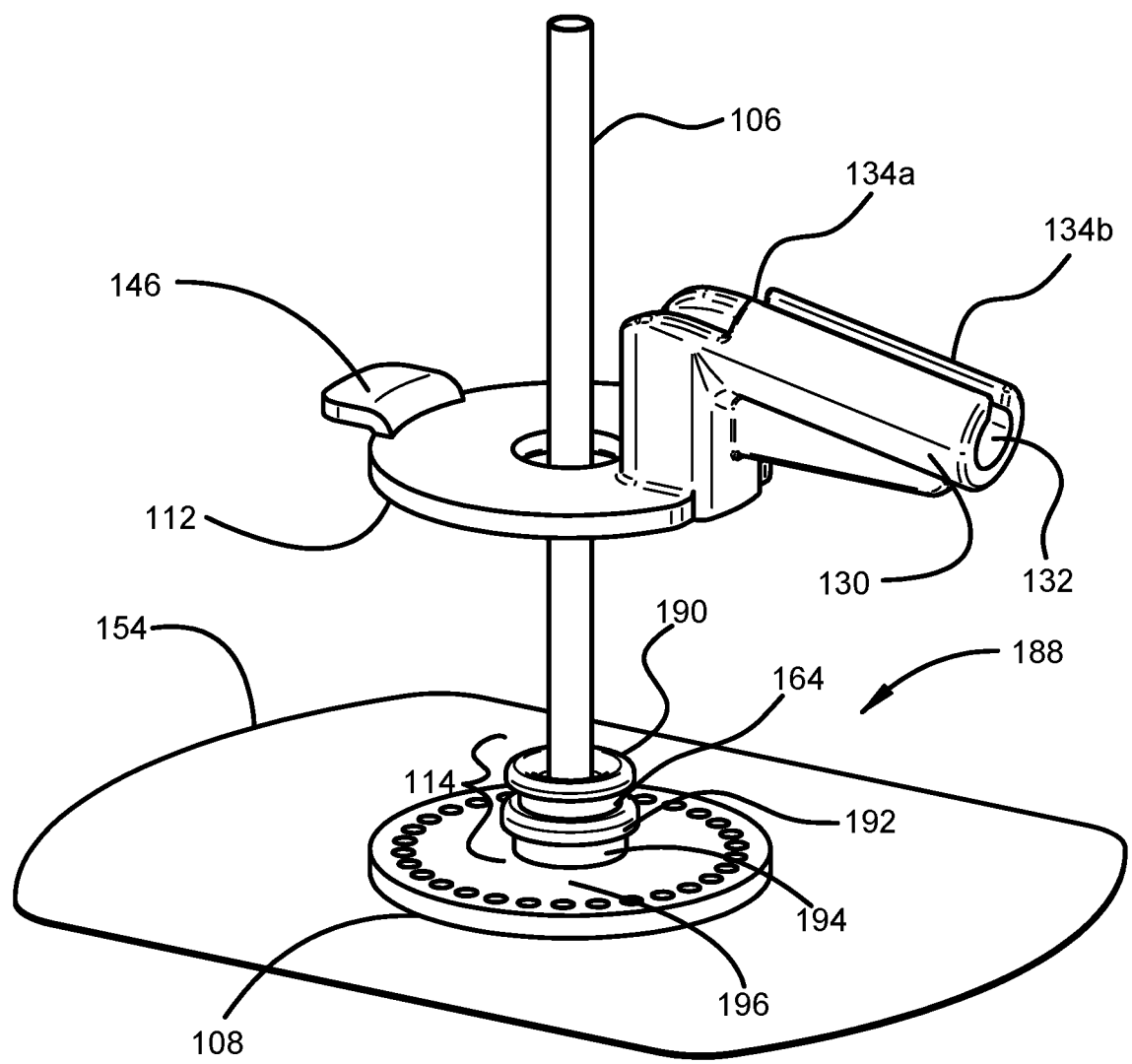
FIG. 27 illustrates addition of a bent tube holder with rotatable mounting on the first preliminary product form of FIGS. 25 and 26, during manufacture of an example medical tube securement device.
Figure 28:
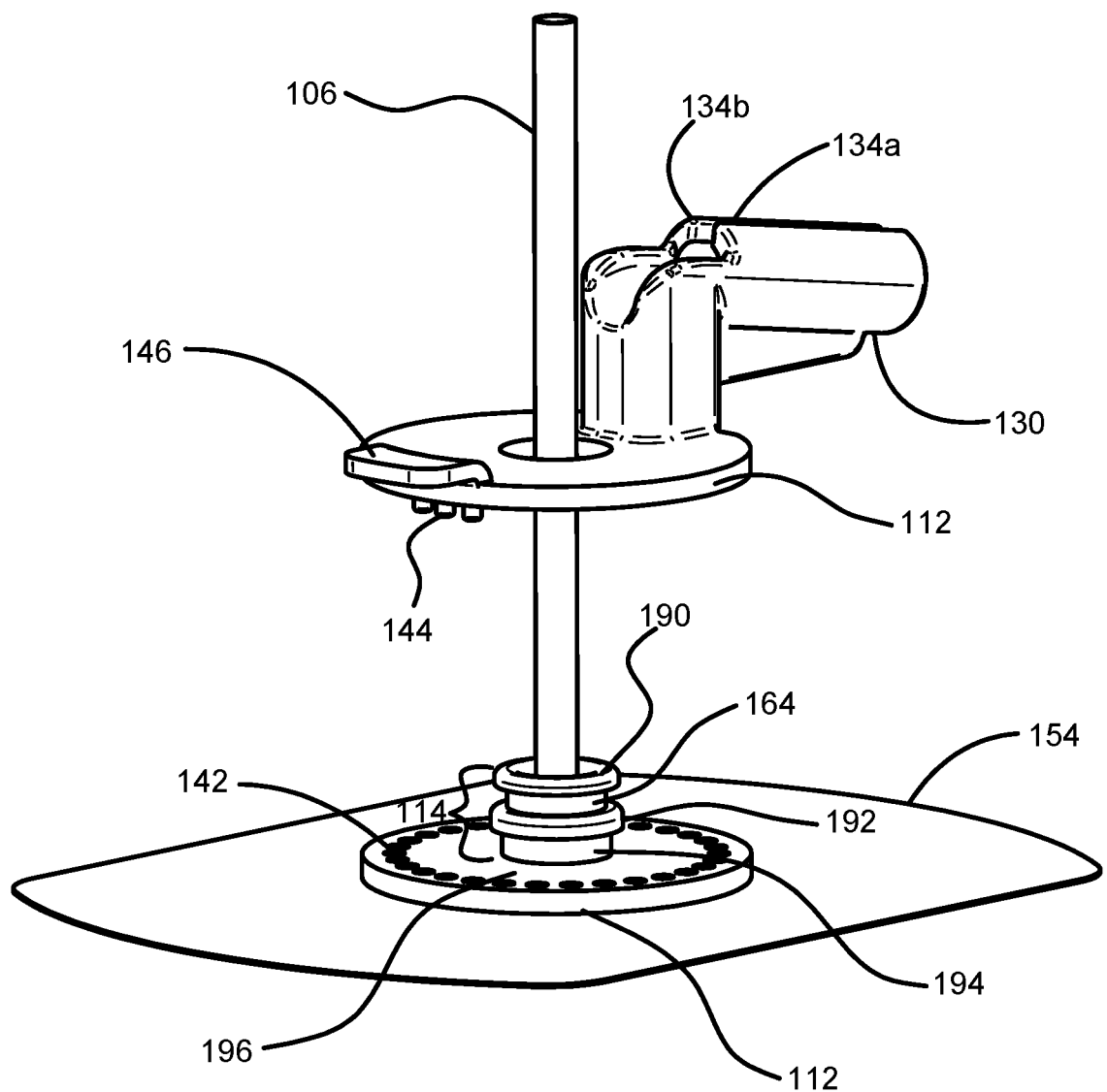
FIG. 28 further illustrates addition of the bent tube holder on the first preliminary product form of FIGS. 25 and 26, during manufacture of an example medical tube securement device.
Figure 29:
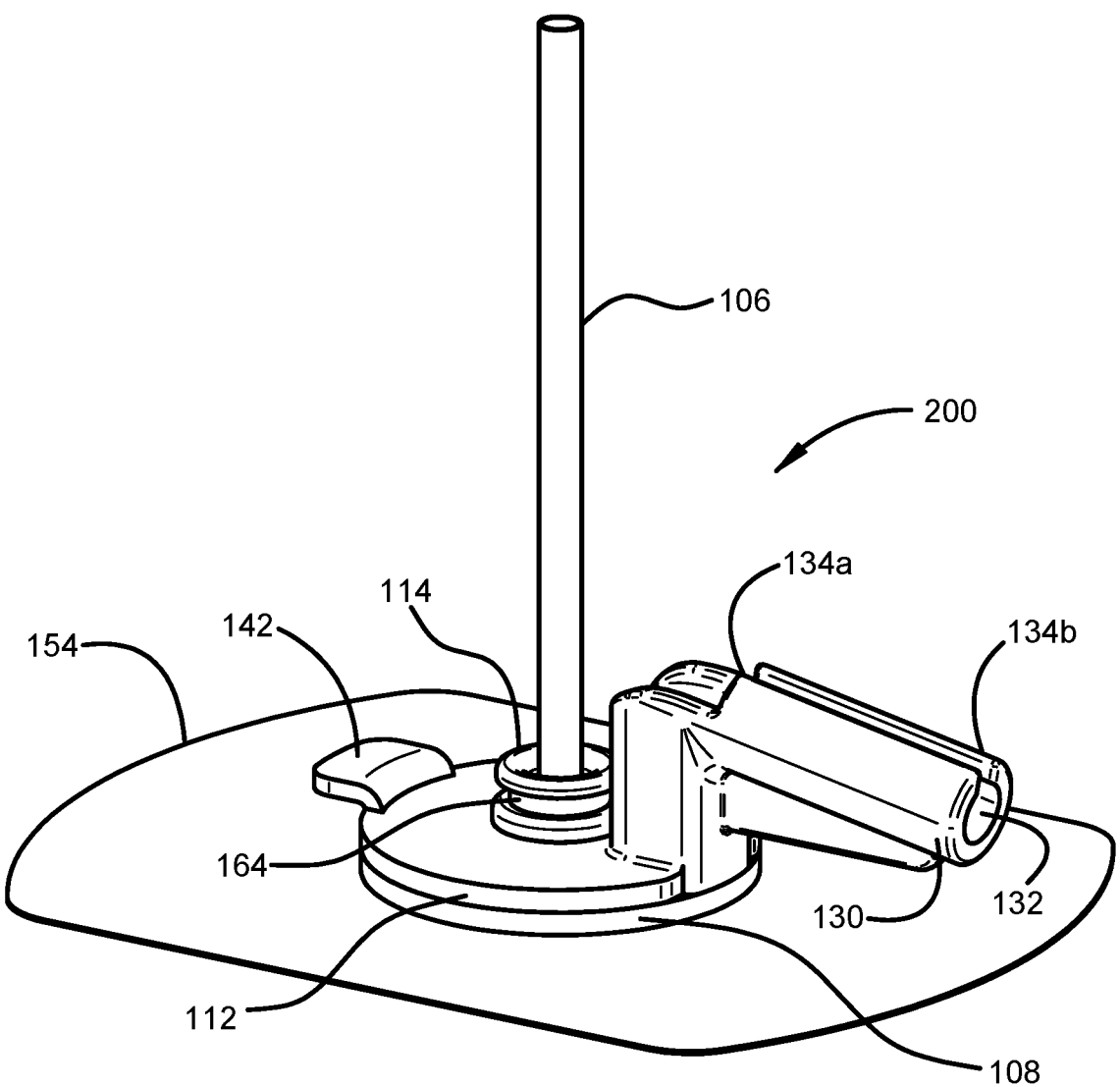
FIG. 29 is a perspective view of an example of a second preliminary product form during manufacture of an example medical tube securement device.

FIGS. 27-29 illustrate processing to attach the rotating member 112, including the bent sleeve holder 130, to the preliminary product form 188 shown in FIGS. 25 and 26. As shown in FIGS. 27 and 28, with the securement sleeve 106 disposed through an aperture of the rotating member 112 with a proximal face of the rotating member 112 facing a distal side of the base member 108, the rotating member 112 is advanced along the securement sleeve 106 toward the extension portion 114 of the base member 108. FIG. 27 shows the extension portion 114 of the base member 108 as including a first lip ring 190 and a second lip ring 192 and with the securement recess 164 being between the first lip ring 190 and the second lip ring 192. The extension portion 114 also includes a circular groove track 194 between the second lip ring 192 and a flange surface 196 of the base member 108. The rotating member 112 is advanced over the securement sleeve 106 and over the extension portion 114 of the base member 108 until the rotating member 112 is engaged in the circular groove track 194. The rotating member 112 is made of a suitably flexible material to permit the material at the perimeter of the aperture to deflect over the first circular lip 190 and over the second circular lip 192 and then snap into place in the circular groove track 194 with the rotating member 112 being rotatably retained in the circular groove track 194 and rotatable about the extension portion 114 of the base member 108. As shown in FIG. 28, as the rotating member 112 is advanced to engage the extension portion 114, the projections 144 may be aligned with corresponding recesses 142 to position the engaged rotating member 112 at a desired radial position relative to the base member 108. FIG. 29 shows an assembled second preliminary product form 200 including the added rotating member 112.

Figure 30:
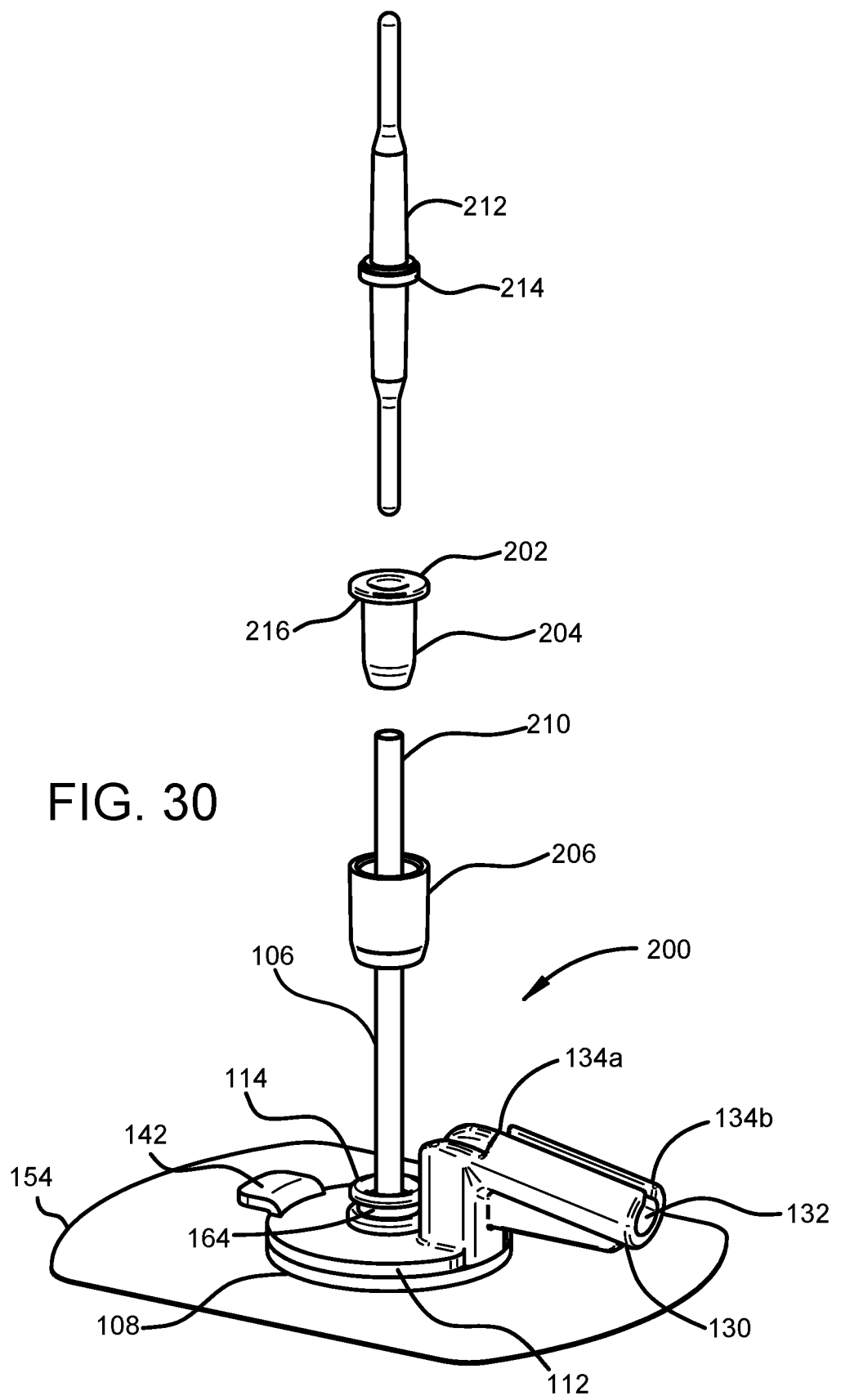
FIG. 30 illustrates assembly of additional components with the second preliminary product form of FIG. 29 during manufacture of an example medical tube securement device.
Figure 31:
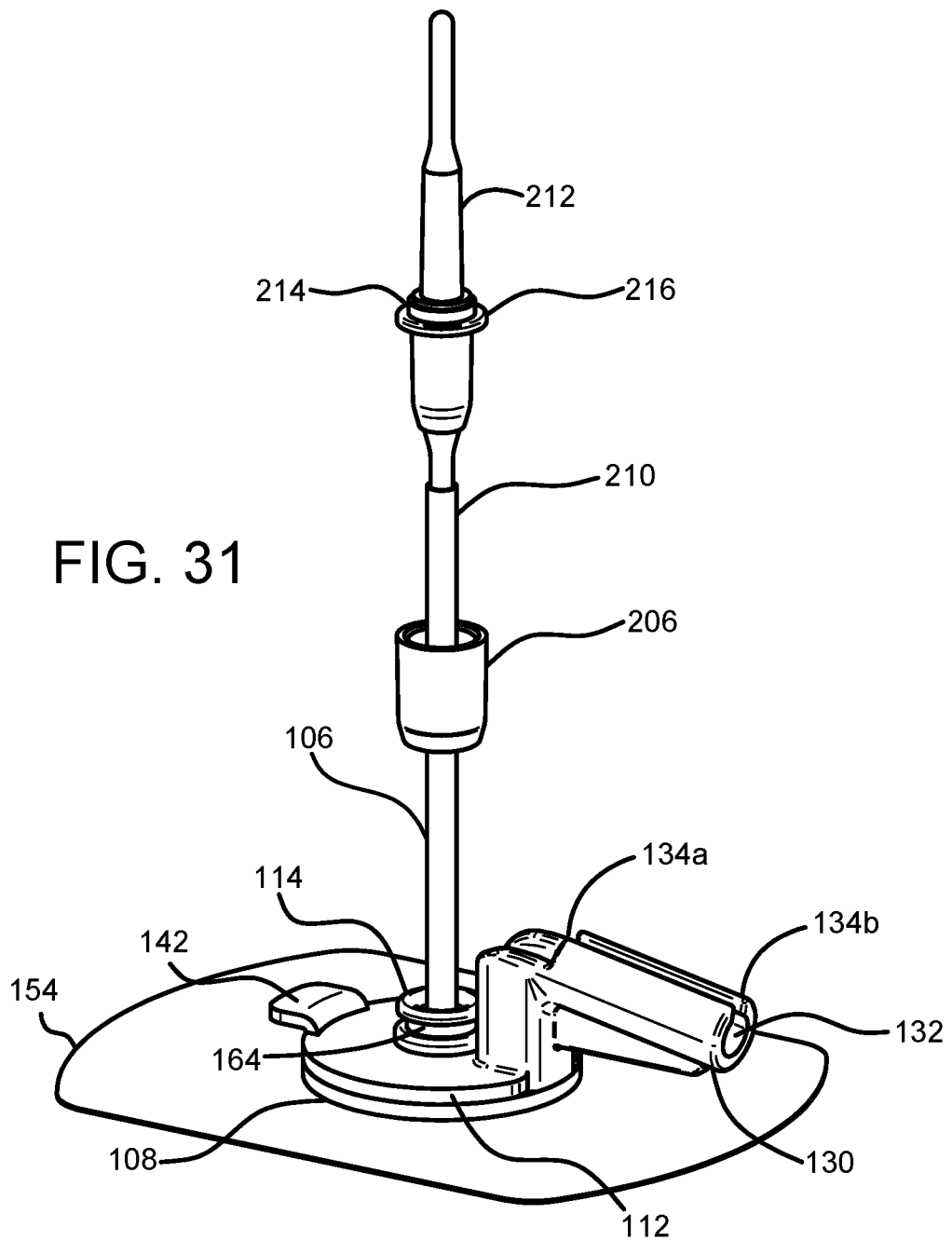
FIG. 31 further illustrates assembly of additional components with the second preliminary product form of FIG. 29 during manufacture of an example medical tube securement device.
Figure 32:
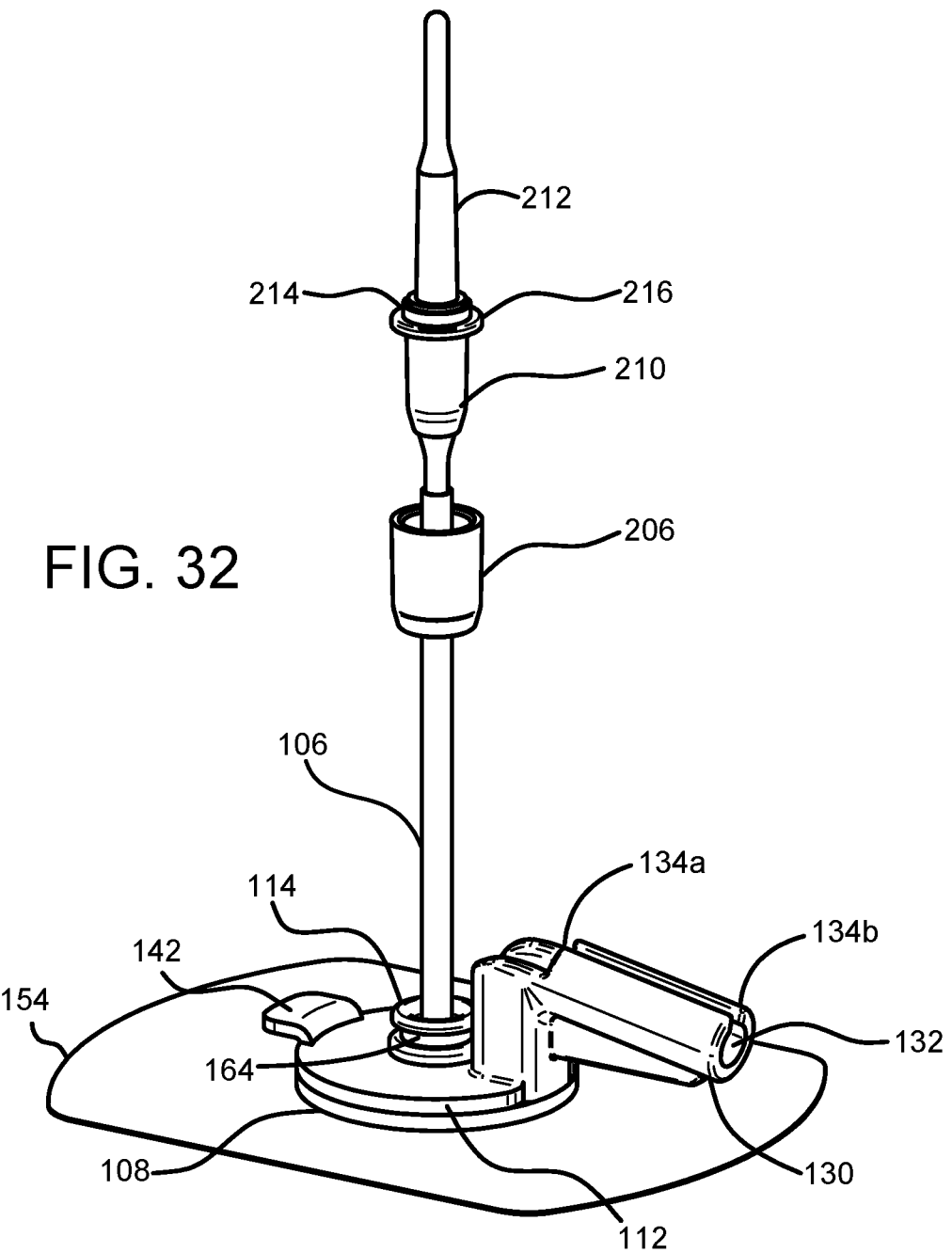
FIG. 32 further illustrates assembly of additional components with the second preliminary product form of FIG. 29 during manufacture of an example medical tube securement device.
Figure 33:
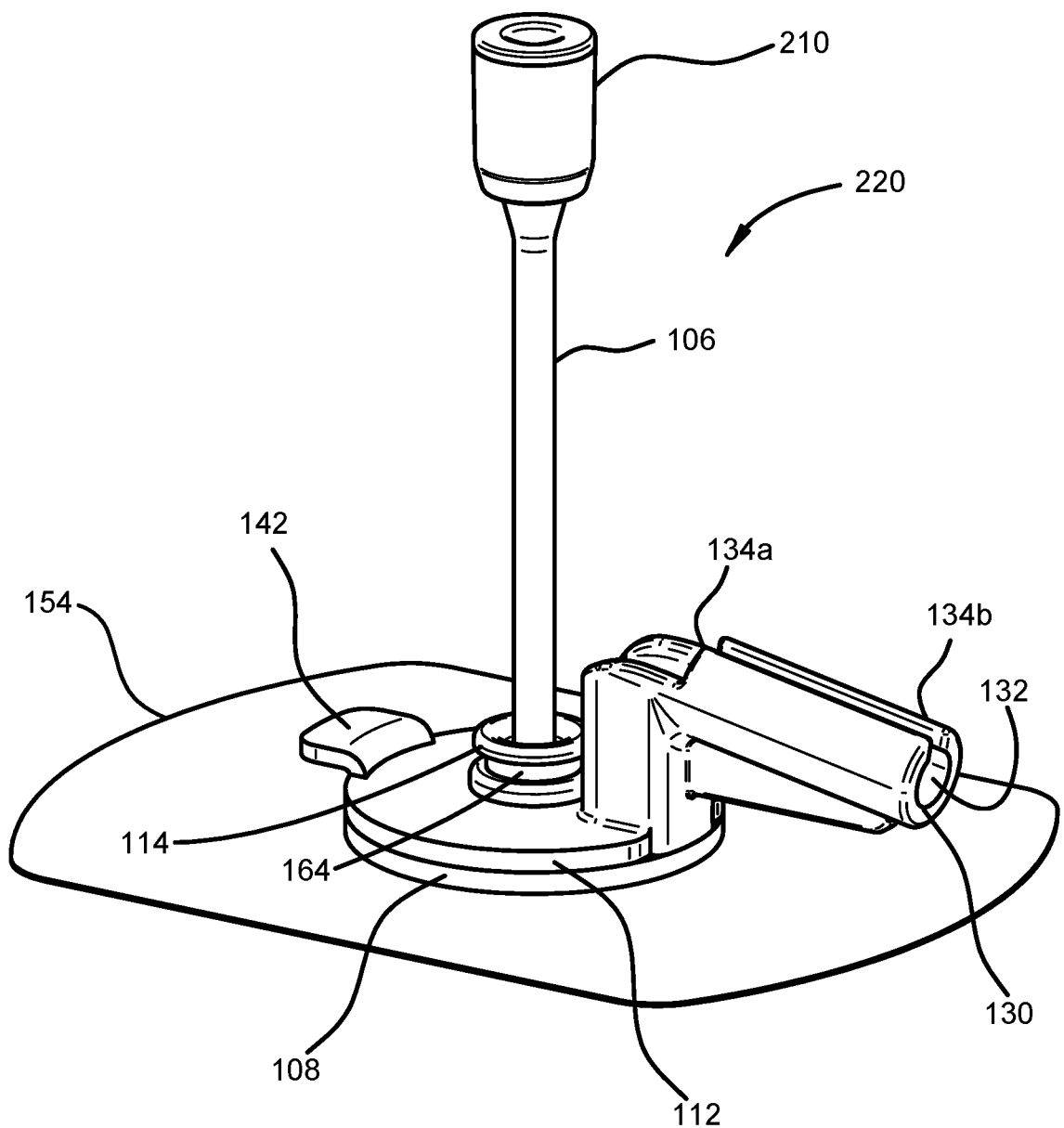
FIG. 33 is a perspective view of a third preliminary product form during manufacture of an example medical tube securement device.

FIGS. 30-33 illustrate processing to add the distal collar 110 at the distal end of the securement sleeve 106 of the second preliminary product form 200. A collar assembly of the distal collar 110 includes a collar member 202 with a collar nipple 204 and a retaining member 206. FIG. 30 illustrates the securement sleeve 106 disposed through an opening through the retaining member 206 and the collar member 202 positioned for engagement with a distal end portion 210 of the securement sleeve 106 using an insertion tool 212. FIG. 31 shows a leading end of the insertion tool 212 inserted into the distal end portion 210 of the securement sleeve 106 and FIG. 32 shows the insertion tool 212 fully advanced into the distal end portion 210 of the securement sleeve 106 with the distal end of the securement sleeve 106 contacting a stop collar 214 of the insertion tool 212. The retaining member 206 is then advanced over the distal end portion 210 of the securement sleeve 106 to bias a sleeve wall of the distal end portion 210 against the collar nipple 204. The retaining member 206 is advanced until a distal end of the retaining member 206 is adjacent, and preferably contacting, a distal collar portion 216 of the collar member 202. The assembled collar member 202 and the retaining member 206 holding the distal end portion 210 form the distal collar 110, which is illustrated in a resulting third preliminary product form 220 in FIG. 33.

Figure 34:
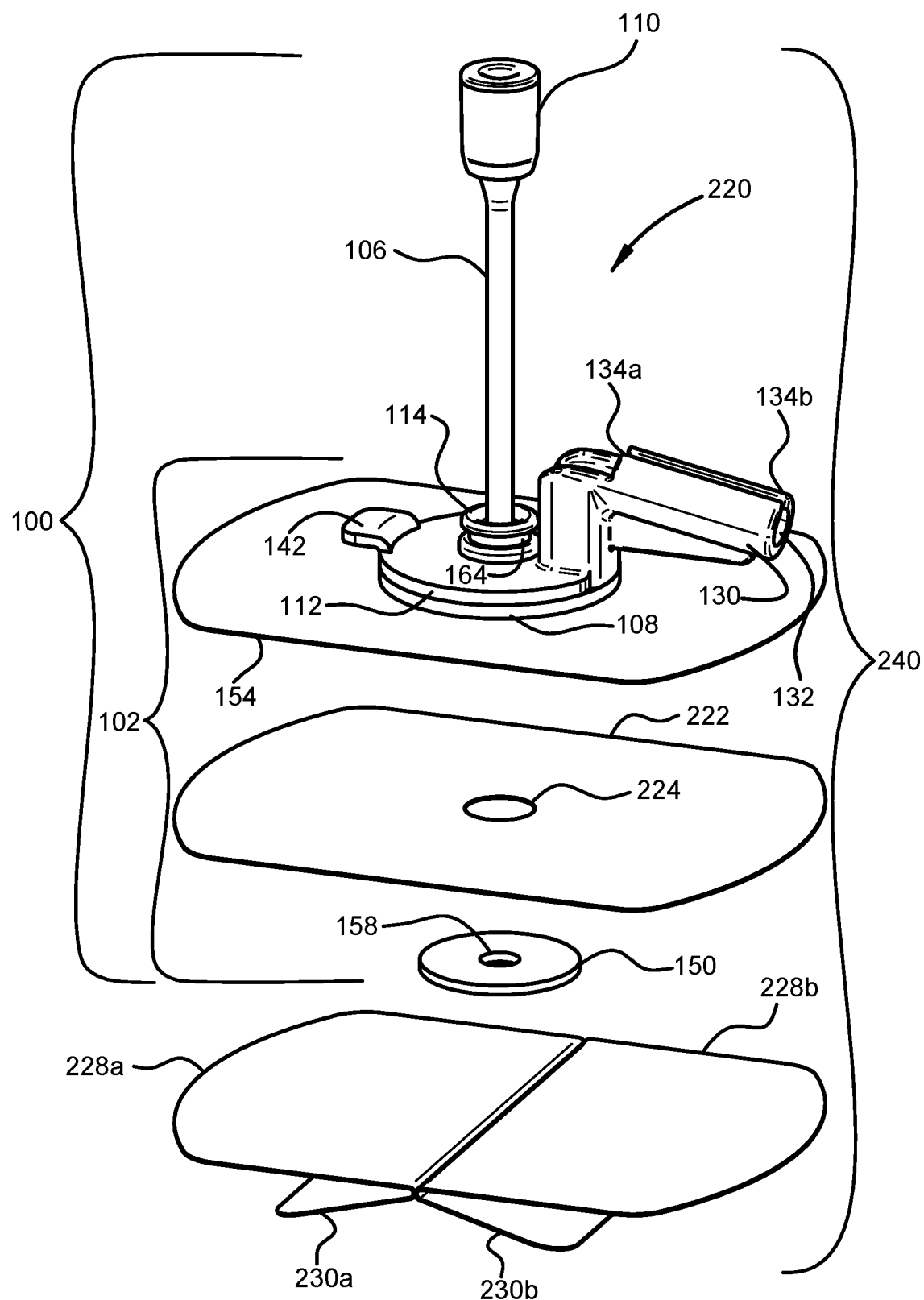
FIG. 34 illustrates assembly of additional components with the third preliminary product form of FIG. 33 to prepare an example medical tube securement product including an example medical tube securement device.

Reference is now made to FIG. 34 illustrating processing to add the absorbent pad 150 to the third preliminary product form 220 to complete the attachment pad 102 and prepare the securement device 100 of FIG. 1. FIG. 34 also shows adding a peelable backing over a proximal side 152 of the attachment pad 102 to prepare a medical drain securement product including the securement device and the peelable backing. FIG. 34 shows a layer of pressure-sensitive adhesive 222 that is applied to a proximal side of the structural sheet 154 of the third preliminary product form, and the absorbent pad 150 is attached to the proximal side of the structural sheet 154 using a portion of the adhesive layer 222 and with the aperture 158 of the absorbent pad 150 aligned with an aperture 224 of the adhesive layer 222 and with a corresponding aperture of the structural sheet 154. As shown in FIG. 34, the structural sheet 154, adhesive layer 222 and absorbent pad 150 make up the attachment pad 102 when assembled. The adhesive layer 222 may contain an antimicrobial agent, similar to the discussion of a possible antimicrobial agent for the absorbent pad 150. The aligned apertures through the absorbent pad 150, adhesive layer 222 and structural sheet 154 form the portion of the tube passage 116 that is through the attachment pad 102. As illustrated in FIG. 34, addition of the attachment pad 102 to the third preliminary product form 220 forms the securement device 100 of FIG. 1.

Also shown in FIG. 34 is application of a peelable backing over the proximal side 152 (shown in FIG. 16) of the attachment pad 102, with the peelable backing being adhered to the attachment pad 102 through the adhesive layer 222 to form a medical tube securement product 240. In the illustrated example in FIG. 34, the peelable backing is made of two flexible backing pieces 228a,b adhered to the adhesive layer 222 around the absorbent pad 150 and covering the absorbent pad 150. The flexible backing pieces 228a,b have peeling tabs 230a,b which a person may grab and pull apart to remove the peelable backing sheets 228a,b from the attachment pad 102 to expose the absorbent pad 150 and the adhesive layer 222 around the periphery of the absorbent pad 150, for example to permit the proximal side 152 of the attachment pad to be adhered to skin of a patient during use of the securement device 100.

As will be appreciated, the securement device 100' including the engaged compression retainer 160 as illustrated in FIGS. 18 and 19 may be made from the securement device 100 illustrated in FIG. 34 by compressing the securement sleeve 106 to the compressed configuration and positioning the compression retainer 160 to engage the distal collar 110 and the extension portion 114 of the base member 108 to retain the securement sleeve 106 in the compressed configuration as illustrated in FIGS. 18 and 19. Thus, the medical tube securement product 240 may be prepared to include the securement device 100' by inclusion of the compression retainer 160. The compression retainer 160 may be included preinstalled to retain the securement sleeve 106 in the compressed configuration or the compression retainer 160 may be included but not preinstalled in such a manner, for example as a separate piece that may be installed by a medical practitioner to hold the securement sleeve 106 in the compressed configuration as desired.

Figure 35:
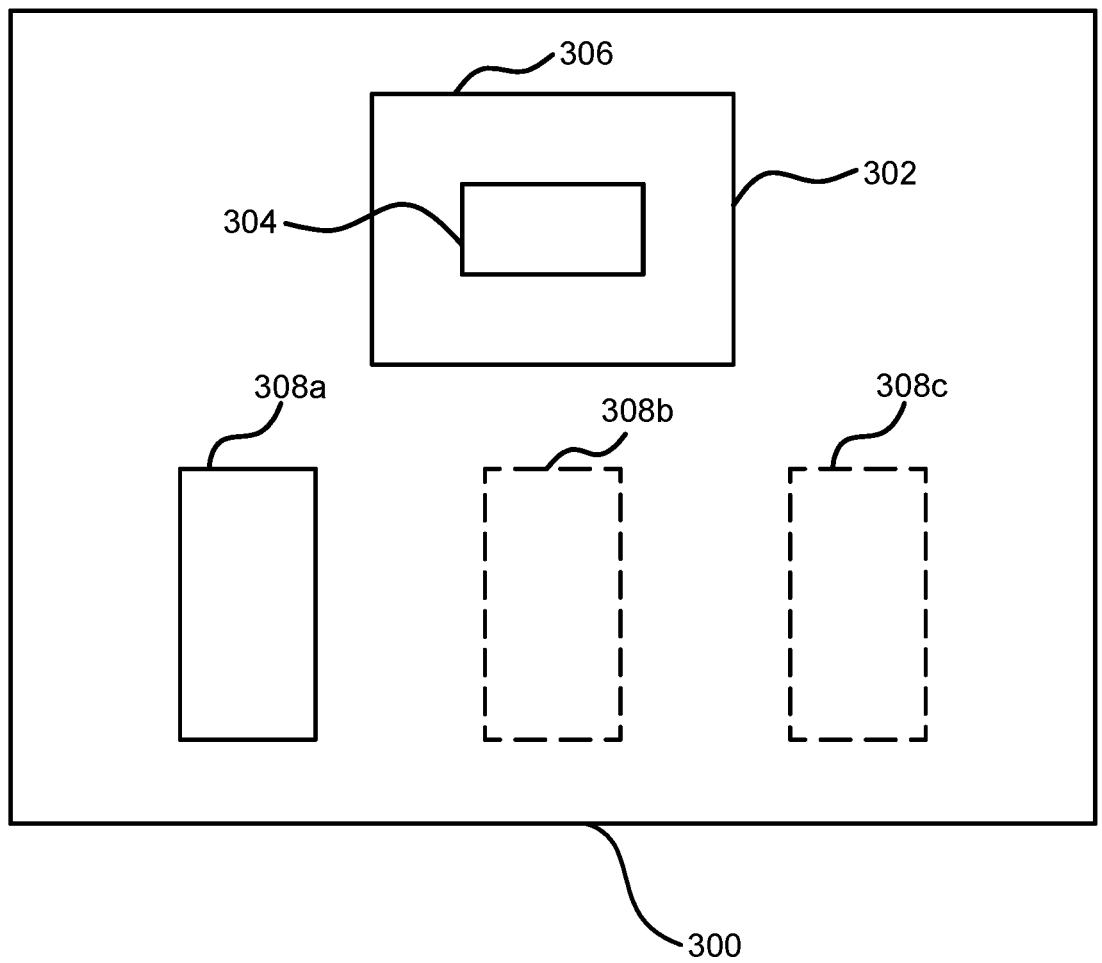
FIG. 35 is an illustration of an example kit including a medical tube securement device and one or more additional components.

Reference is now made to FIG. 35 showing an example kit 300 including a medical tube securement product 302. The medical tube securement product 302 includes a medical tube securement device 304 disposed in a hermetically-sealed enclosure 306. The medical tube securement device 304 can for example be, or include any features of, the example securement device 100 or the example securement device 100' illustrated or described in relation to any of FIGS. 1-34, the example securement device 350 illustrated or described in relation to any of FIGS. 36-38, or the example securement device 100" or example securement device 100'" illustrated or described in relation to any of FIGS. 39-51. The medical tube securement device 304 can for example be in the form of, or have any features of, the medical tube securement product including such a securement device, with or without a compression retainer and including a peelable backing, for example as illustrated for the medical tube securement product 240 illustrated in FIG. 34. The medical tube securement device 304 is preferably sterile in the hermetically-sealed enclosure 306. Sterilization of the securement device 304 may be accomplished before or after sealing the securement device 304 in the hermetically-sealed enclosure 306. In one preferred method, the medical tube securement device is sterilized after being sealed in the hermetically-sealed enclosure 306 by exposure to radiation that penetrates the enclosure 306 and sterilizes the medical tube securement device in the enclosure 306. The hermetically-sealed enclosure 306 may for example be made of a polymeric material of a type used to package medical devices. The kit 300 is illustrated as containing only a single medical tube securement product 302, but in alternative variations such a kit can include a plurality of any number of such medical tube securement products 302.

With continued reference to FIG. 35, the kit 300 includes at least one additional component 308a, but may include a plurality of additional components, illustrated in FIG. 35 as including optional additional components 308b and 308c, although it will be appreciated that the kit may include any number of additional components, which may be in excess of three. Examples of product types for the additional component 308a include a medical tube or any other of the product types disclosed herein for an additional product in a kit. When a plurality of additional components are included in the kit 300, each one of the additional components may be the same type of product, or different ones of the additional components may be different types of products.

Figure 36:
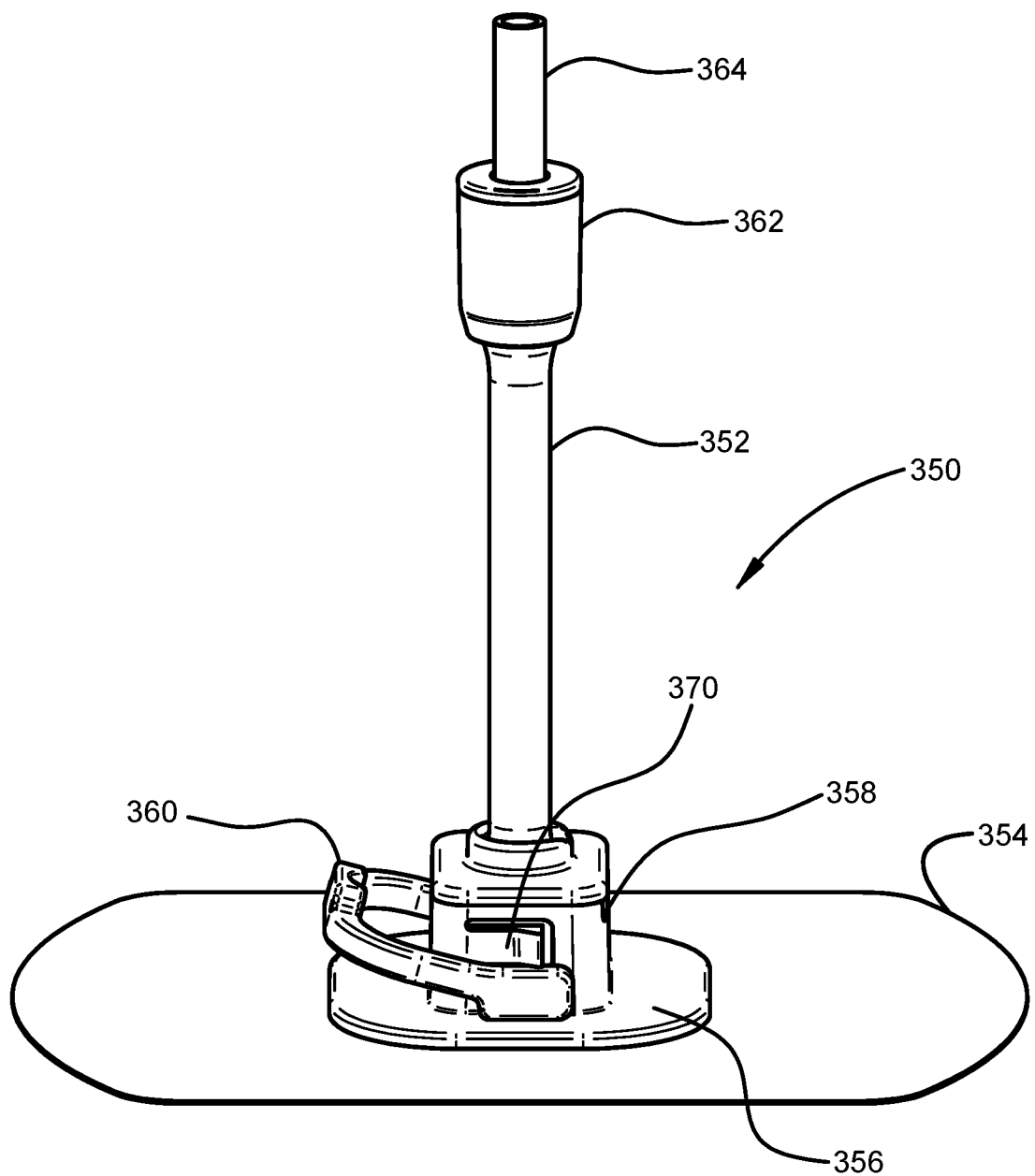
FIG. 36 is a perspective view of an example embodiment of a medical tube securement device.
Figure 37:
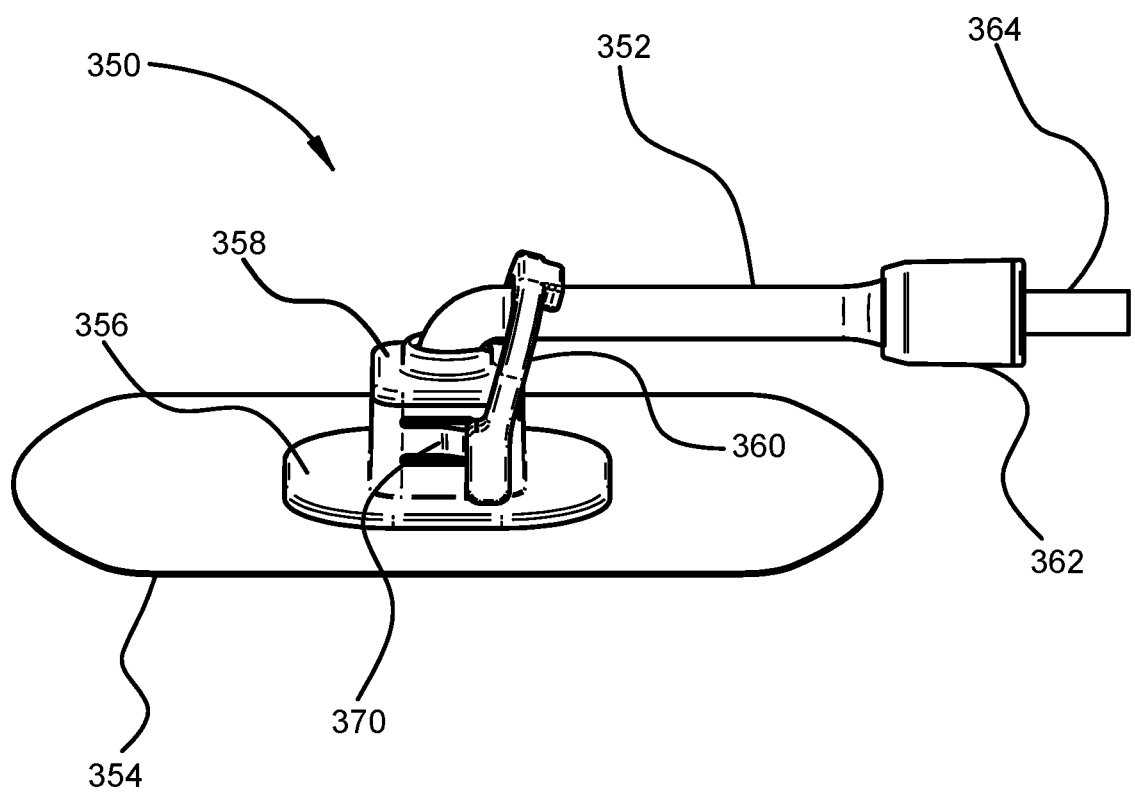
FIG. 37 is a perspective view of the medical tube securement device of FIG. 36 and showing the securement sleeve retained in a bent configuration by a bent tube holder.
Figure 38:
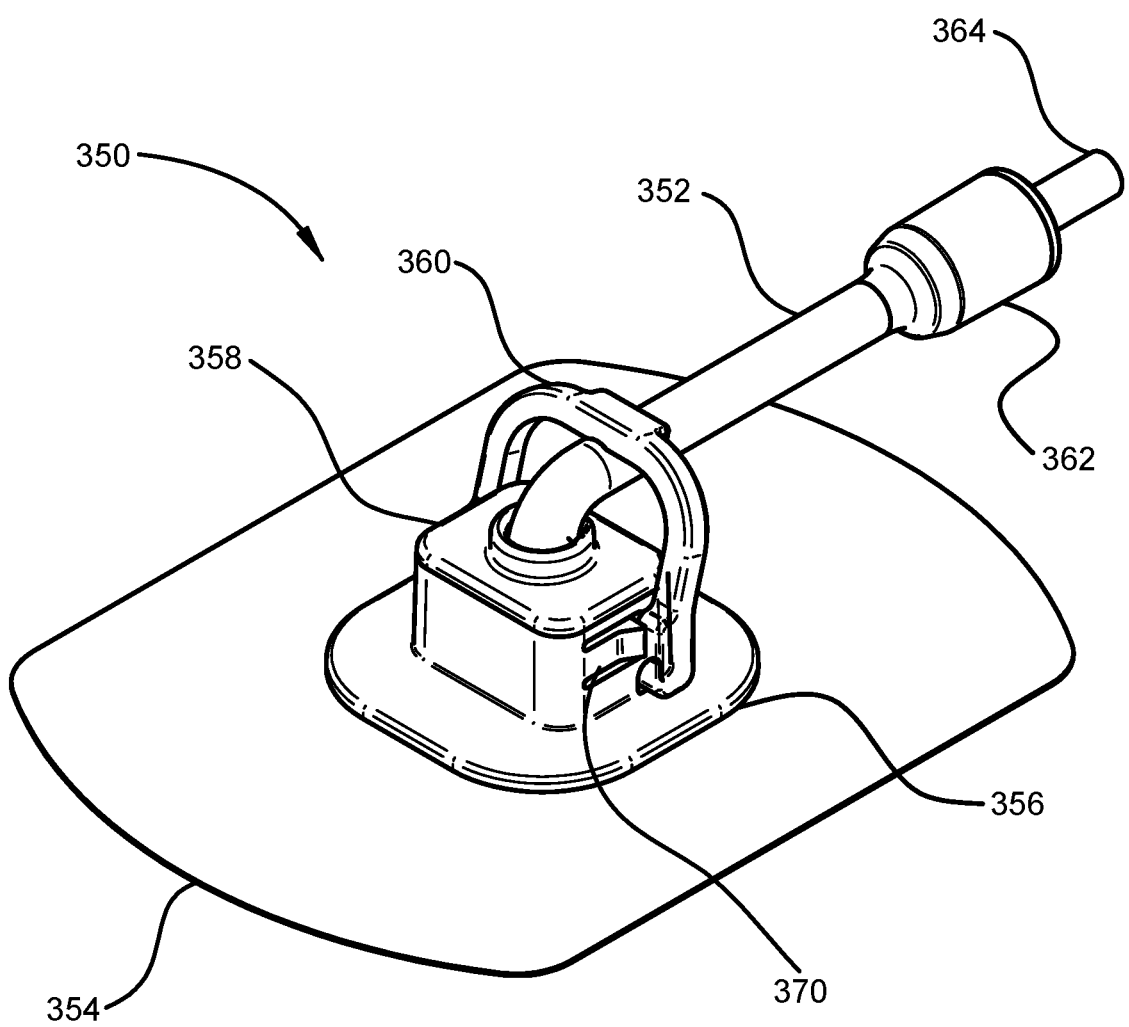
FIG. 38 is another perspective view of the medical tube securement device of FIG. 36 and showing the securement sleeve retained in a bent configuration by a bent tube holder.
Figure 39:
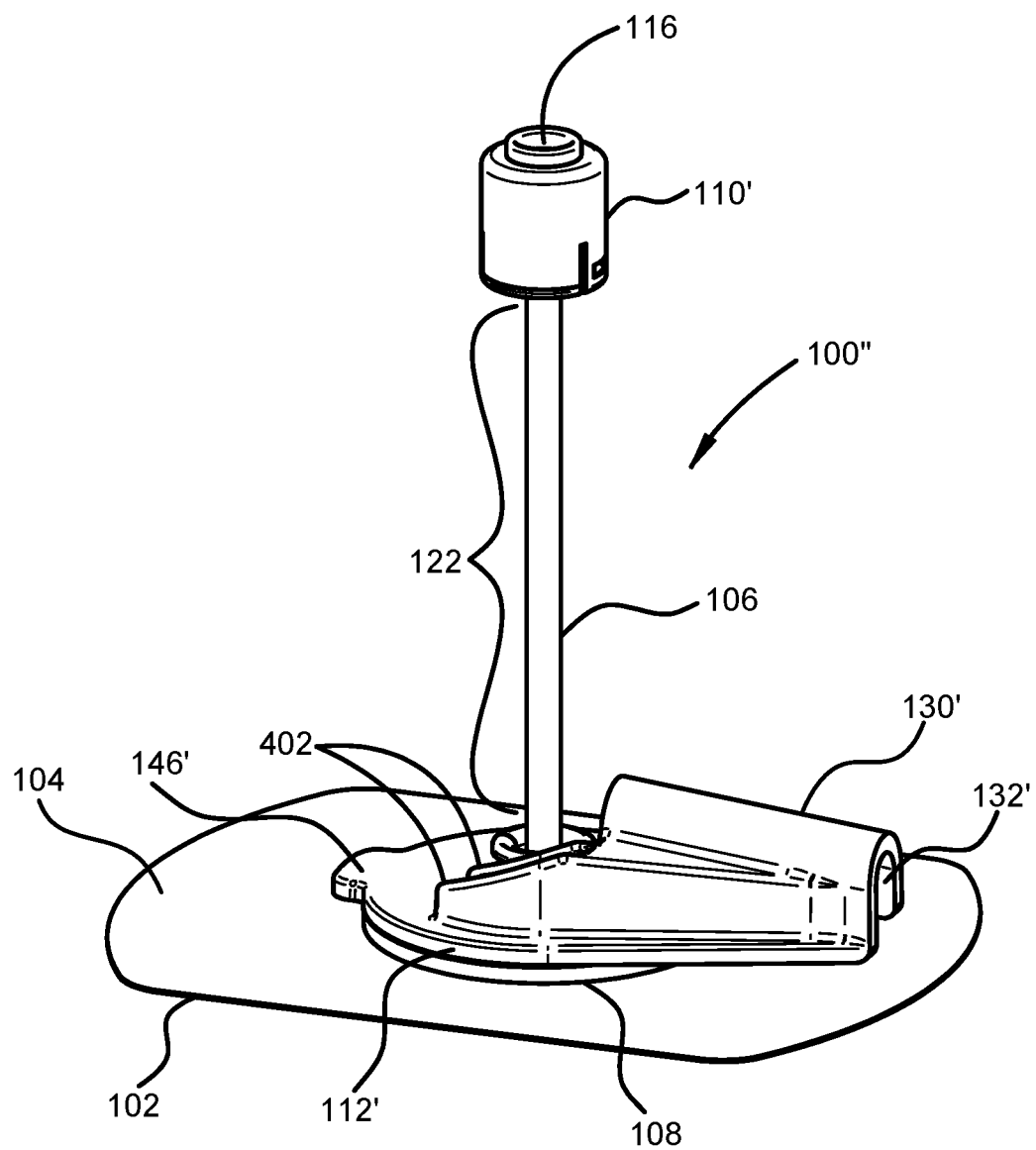
FIG. 39 is a perspective view of another example embodiment of a medical tube securement device.
Figure 40:
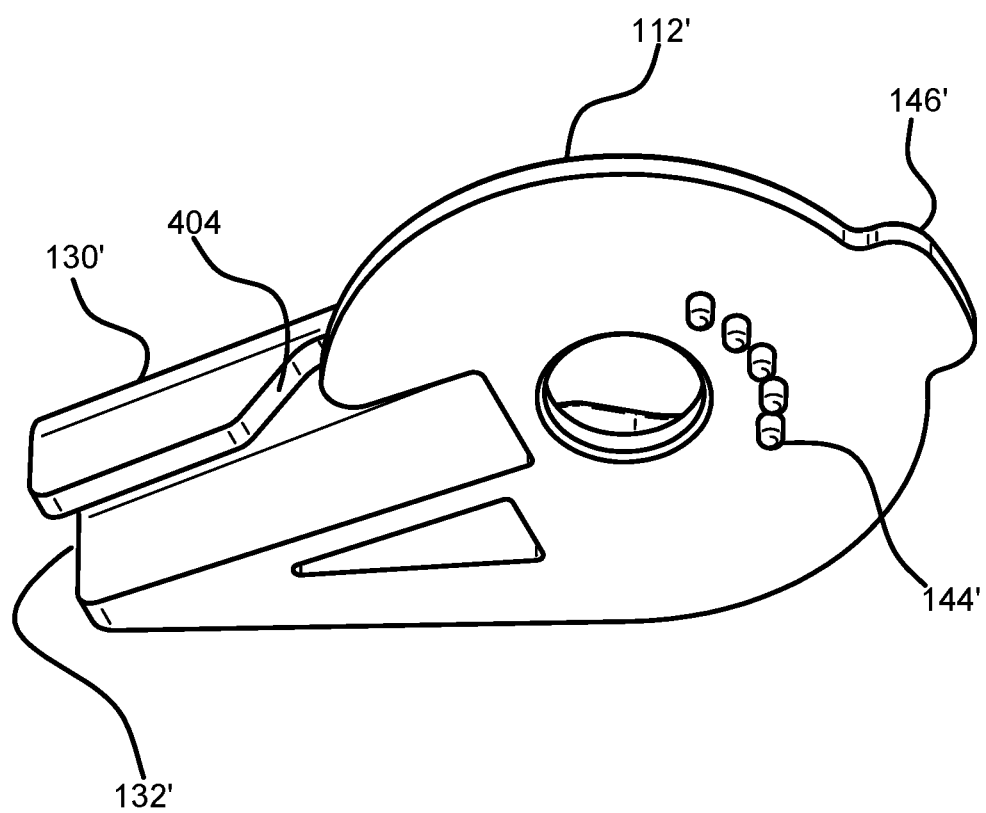
FIG. 40 is a perspective view of a rotating member and bent sleeve holder of the medical tube securement device of FIG. 39.

Reference is now made to FIGS. 36-38 in relation to another example of a medical tube securement device with capability to selectively retain a medical tube in a bent configuration. FIGS. 36-38 illustrate an example medical tube securement device 350 including a securement sleeve 352 with a securement portion made of a braided textile construction. The securement portion can for example be or have properties as described previously with reference to any of FIGS. 1-20. The securement device 350 includes a base structure including an attachment pad 354, a base member 356, a retaining member 358 and a movable bale member 360. The securement device 350 also includes a distal collar 362. The securement sleeve 352 has a proximal end retained in the base structure and a distal end retained in the distal collar 362. The securement sleeve 352, the securement portion of the securement sleeve 352, the attachment pad 354, the base member 356 and the distal collar 362 can have features the same as or similar to those described previously for corresponding features illustrated in any of FIGS. 1-34. For illustration purposes, the securement device 350 is shown with a medical tube 364 disposed through the tube passage through the medical device 350 and secured to the medical device 350 by the securement portion of the securement sleeve 352.

The securement device 350 includes a bent sleeve holder provided by cooperating features of the retaining member 358 and the bale member 360. The bale member 360 is movable between a first configuration in which the securement sleeve 352 is not retained in a bent configuration, as illustrated in FIG. 36, and a second configuration in which the securement sleeve 352 is retained in a bent configuration, as illustrated in FIGS. 37 and 38. When the bale member 360 is moved from the first configuration as shown in FIG. 36 to the second configuration as shown in FIGS. 37 and 38, the bale member 360 contacts the securement sleeve 352 and biases the securement sleeve 352 into the bent configuration. The retaining member 358 includes a lock feature in the form of a depressible tab 370 with a lip projection that locks the bale member 360 in place when the bale member 360 is positioned into the second configuration. The bale member 360 may be released from the second configuration by depressing the tab 370 sufficiently to permit the bale member 360 to be moved over the lip projection and returned to the first configuration, and with a corresponding release of the securement sleeve 352 from the bent configuration.

In the illustrated example of the securement sleeve of FIGS. 36-38, the retaining member 358 is fixed in position relative to the base member 356 and the attachment pad 358. However in an alternative implementation the retaining member 358 may be rotatably mounted in the base structure so that the retaining member 358 may be rotatable to different radial positions relative to the base member 356 and the attachment pad 358, to permit the securement sleeve 352 in the bent configuration to be bent in different radial directions relative to a longitudinal axis of the tube passage through the attachment pad 352 and the base member 356, similar to that operation of the rotating member 112 illustrated in the securement device 100 of FIGS. 1-16, 18-20 and 34.

Reference is now made to FIGS. 39-42 illustrating another embodiment of a medical tube securement device 100", which has similar features to the securement device 100 of FIGS. 1-16, and reference numerals identifying features of the securement device 100" are the same as those used 1-16 to identify like features, whereas similar but modified alternative features are identified by a like reference number with an added apostrophe at the end. In contrast to the securement device 100 of FIGS. 1-16, the securement device 100" illustrated in FIGS. 39-42 includes alternative configurations for a distal collar 110', rotating member 112' and bent sleeve holder 130'.

As shown in FIGS. 39-42, the bent sleeve holder 130' includes a retaining channel 132' that is open facing the distal side 104 of the attachment pad 102 to receive a portion of the securement sleeve 106 to retain the securement sleeve 106 in a bent configuration in which a distal portion of the securement sleeve 106 is biased toward the skin of a patient when the attachment pad 102 is secured to the skin. The retaining channel 132' is mechanically reinforced with reinforcing ribs 402 that help to stabilize and reduce potential for twisting or bending of the retaining channel 132' during use. On a side of the retaining channel 132' opposite the reinforcing ribs 402, a wall of the retaining channel 132' includes an open side portion 404 that facilitates movement of the bent securement sleeve 106 into and out of the retaining channel 132'.

Figure 41:
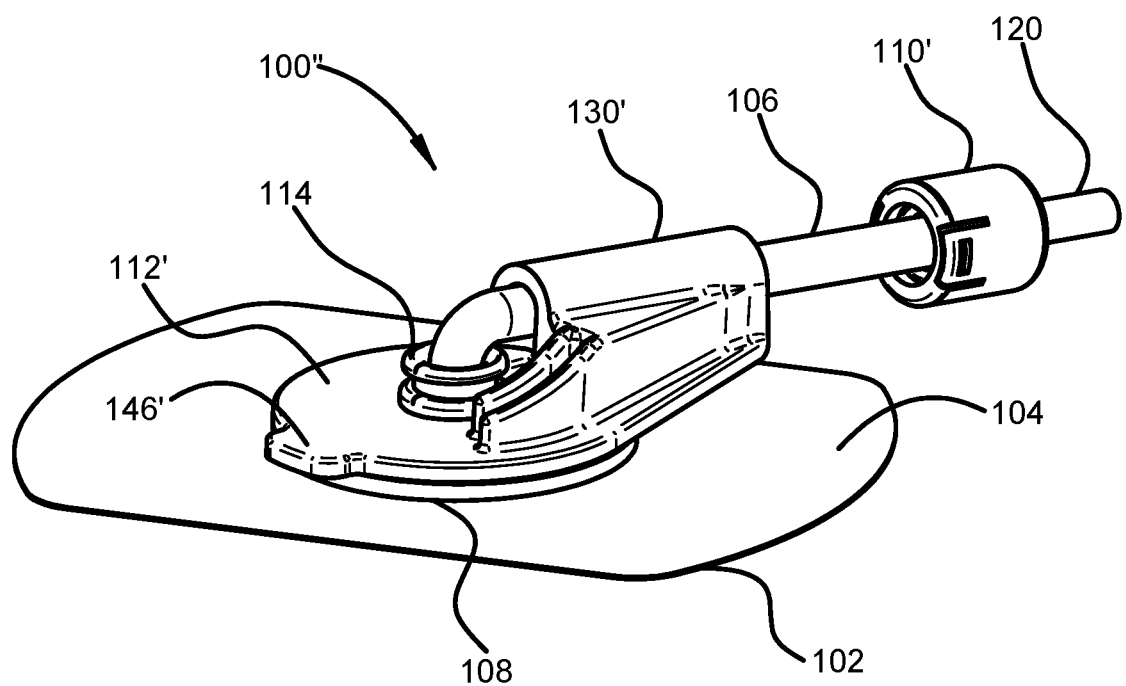
FIG. 41 is a perspective view of the medical tube securement device of FIG. 39 shown securing a medical tube in a bent configuration and with the rotatable member set at an example radial position.
Figure 42:
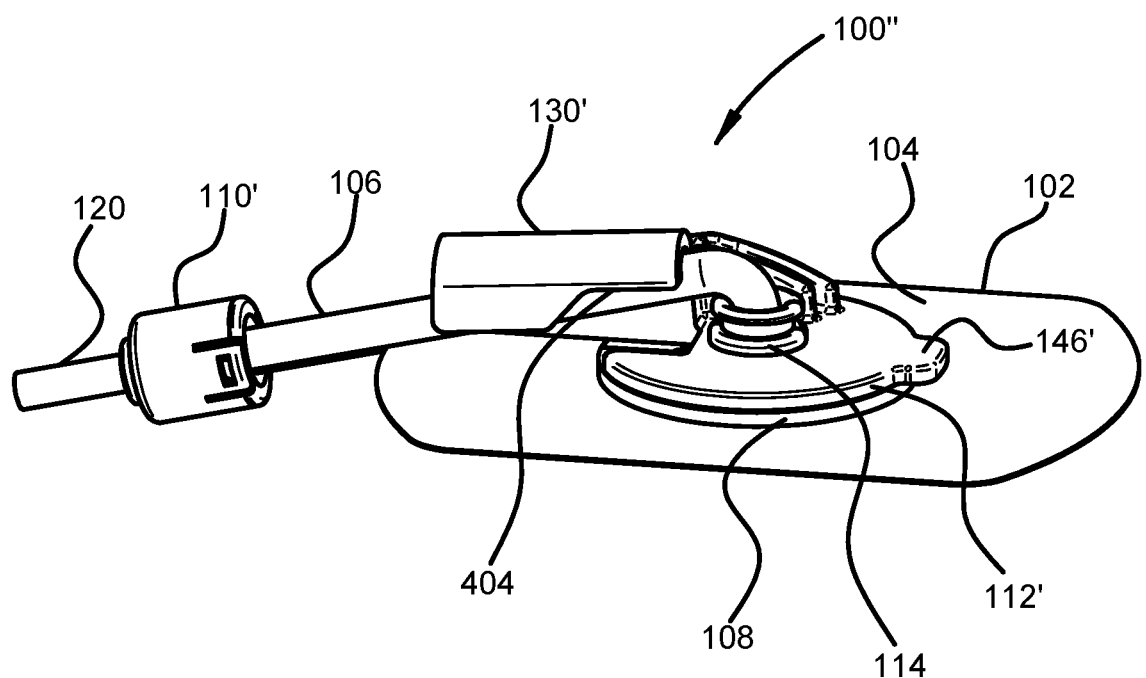
FIG. 42 is a perspective view of the medical tube securement device of FIG. 39 shown securing a medical tube in a bent configuration and with the rotatable member set at a different example radial position relative to that shown in FIG. 40.

Similar to the securement device 100 illustrated in FIGS. 1-16, the securement device 100" includes the bent sleeve holder 130' supported by the rotating member 112'. The rotating member 112' is similar to the rotating member 112 of the securement device 100 illustrated in FIGS. 1-16, except with a somewhat modified design for a manipulation tab 146' and with five projections 144' (shown in FIG. 40) rather than three corresponding projections as illustrated in FIGS. 1-16. As with the securement device 100 illustrated in FIGS. 1-16, the rotating member 112' is rotatable to different radial positions relative to the base member 108. The base member 108 in the securement device 100" has the same configuration as illustrated for the securement device 100 of FIGS. 1-16, with recesses (not shown in FIGS. 39-42) in the base member 108 configured to receive the projections 144' to lock the rotating member 112' at different radial positions. The manipulation tab 146' is deformable in the same manner as described for the manipulation tab 146 of FIGS. 1-16, permitting a user to elastically deform a portion of the rotating member 112' to engage and disengage the projections 144' with the corresponding recesses in the base member 108. FIGS. 41 and 42 illustrate the securement device 100' with the securement sleeve 106 received in the retaining channel 132' of the bent sleeve holder 130' and with the rotatable member 112' locked at different radial positions relative to the base member 108.

The alternative design of the bent sleeve holder 130' has been found to provide enhanced retainment of the securement sleeve 106 in the bent configuration and to be less susceptible to the securement sleeve 106 being inadvertently dislodged from the bent sleeve holder during use.

The alternative distal collar 110' of the securement device 100" of FIGS. 39-42 is constructed with a waterfall design to retain a distal end of the securement sleeve 106, features of which will be better appreciated with reference to FIGS. 43-49.

Figure 43:
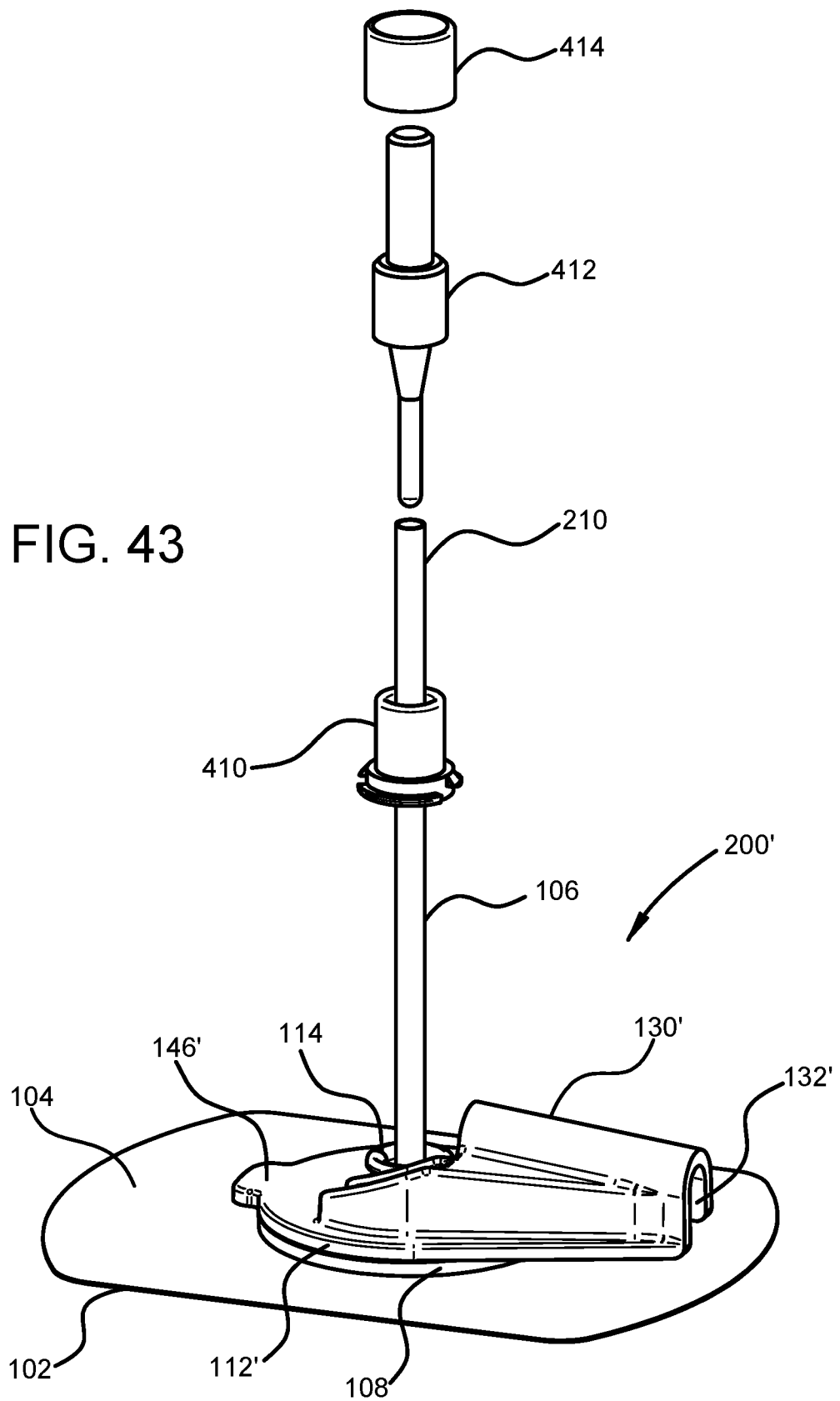
FIG. 43 illustrates a stage of assembly of a distal collar of the medical tube securement device during manufacture of the medical tube securement device of FIG. 39.
Figure 44:
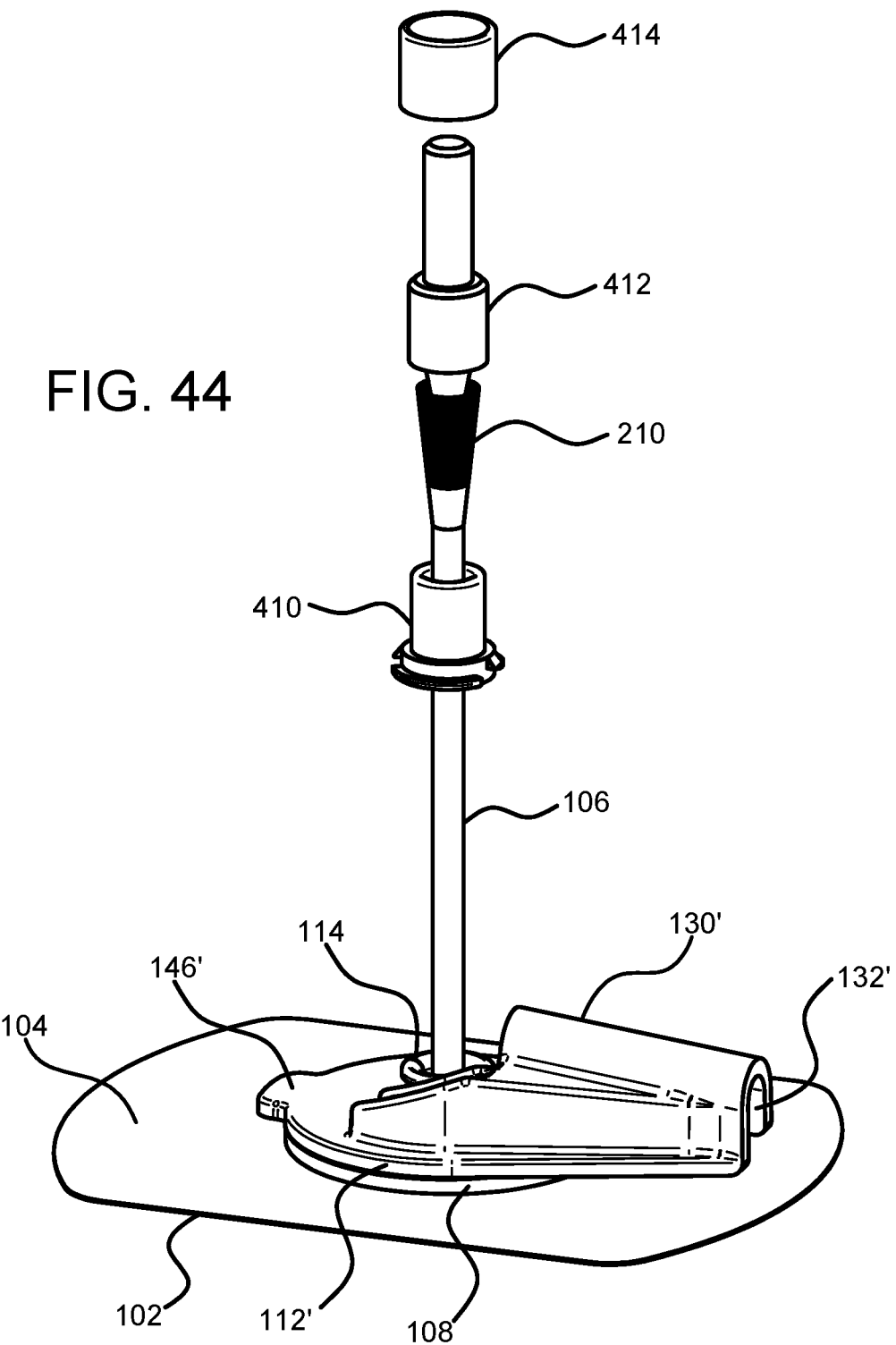
FIG. 44 illustrates another stage of assembly of a distal collar of the medical tube securement device during manufacture of the medical tube securement device of FIG. 39.

Manufacture of the securement device 100" is similar to the method illustrated in and described with reference to FIGS. 21-34, except for modified processing for assembling the modified distal collar 110' of the securement device 100". Reference is now made to FIGS. 43-49 illustrating assembly of the distal collar 110' during manufacture of the securement device 100". FIG. 43 shows a second preliminary product form 200' with an intermediate assembly of the structural sheet 154, base member 108, rotating member 112', securement sleeve 106 and bent sleeve holder 130', and with the rotating member 112' held by and rotatable about the extension portion 114 of the base member 108, similar to the second preliminary product form 200 illustrated in FIG. 29 during manufacture of the securement device 100 of FIGS. 1-16.

Figure 45:
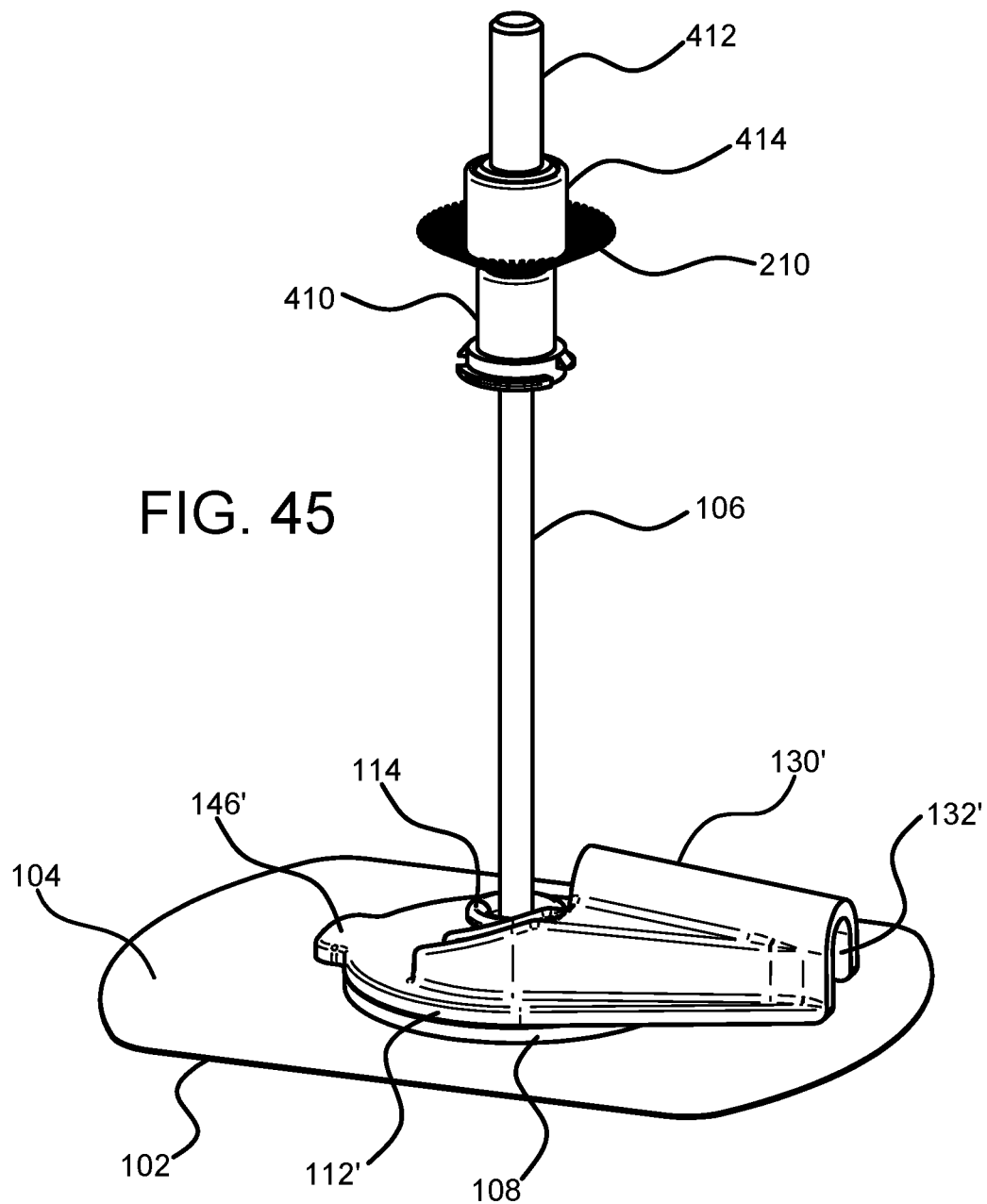
FIG. 45 illustrates another stage of assembly of a distal collar of the medical tube securement device during manufacture of the medical tube securement device of FIG. 39.
Figure 46:
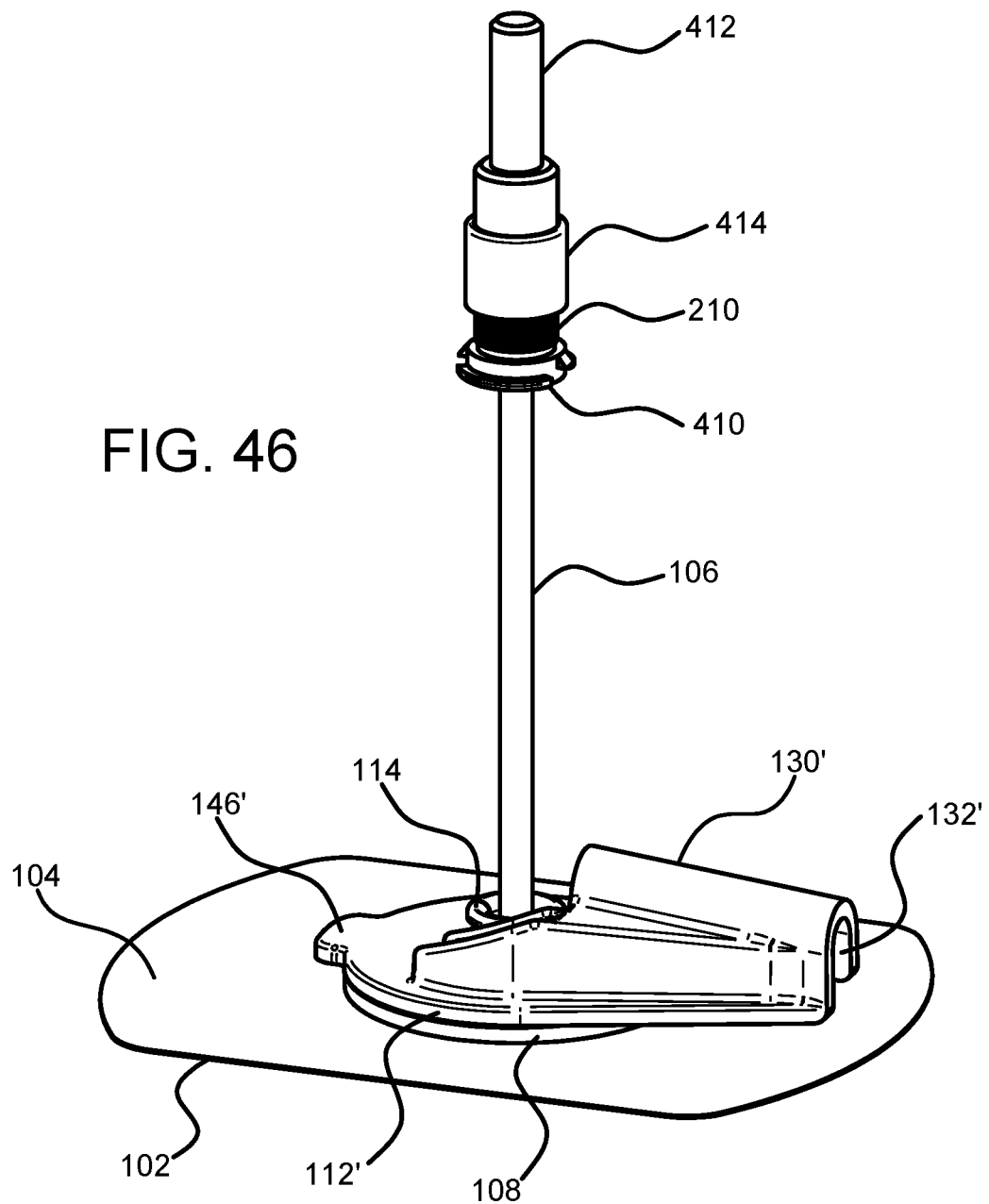
FIG. 46 illustrates another stage of assembly of a distal collar of the medical tube securement device during manufacture of the medical tube securement device of FIG. 39.
Figure 47:
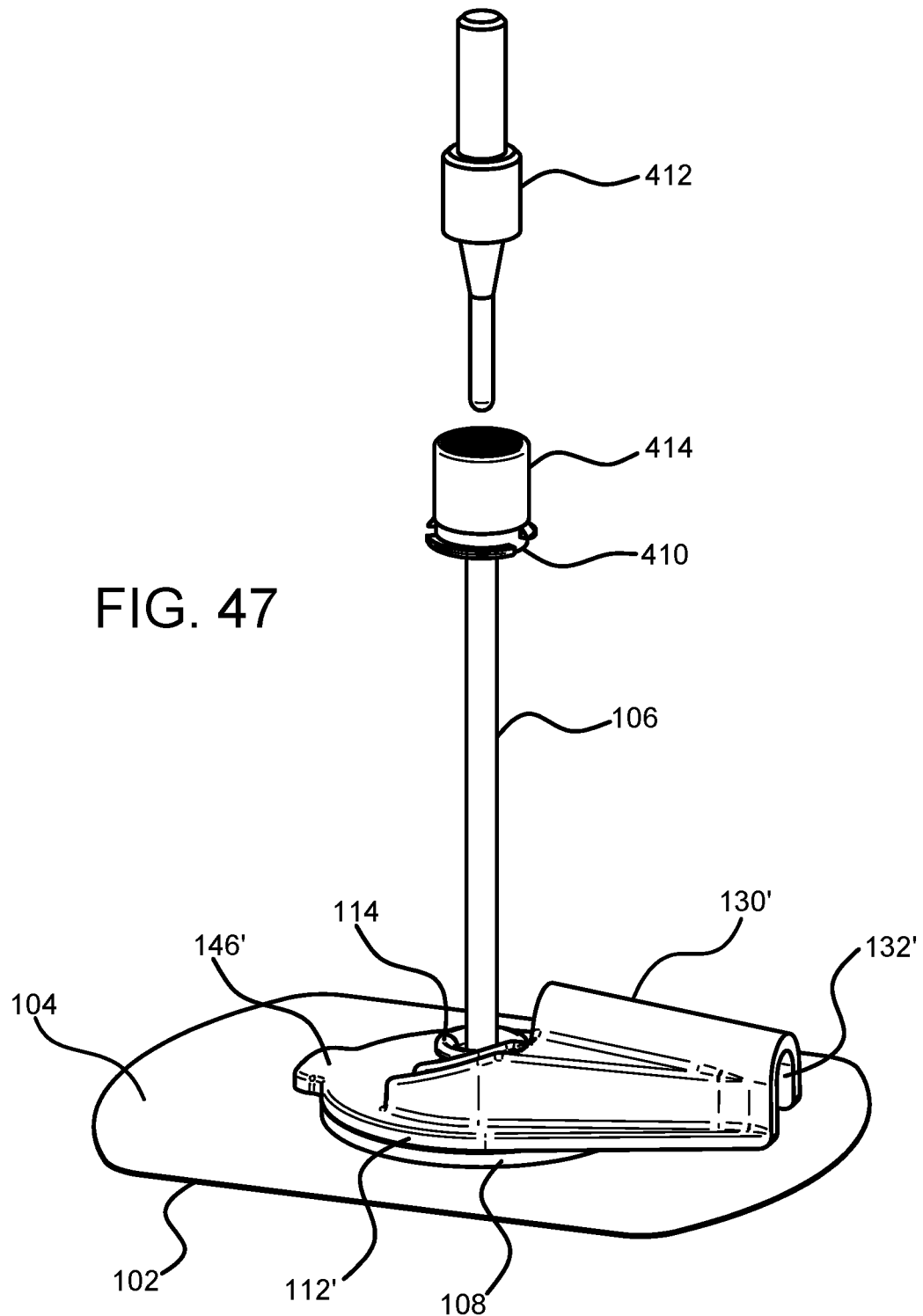
FIG. 47 illustrates another stage of assembly of a distal collar of the medical tube securement device during manufacture of the medical tube securement device of FIG. 39.
Figure 48:
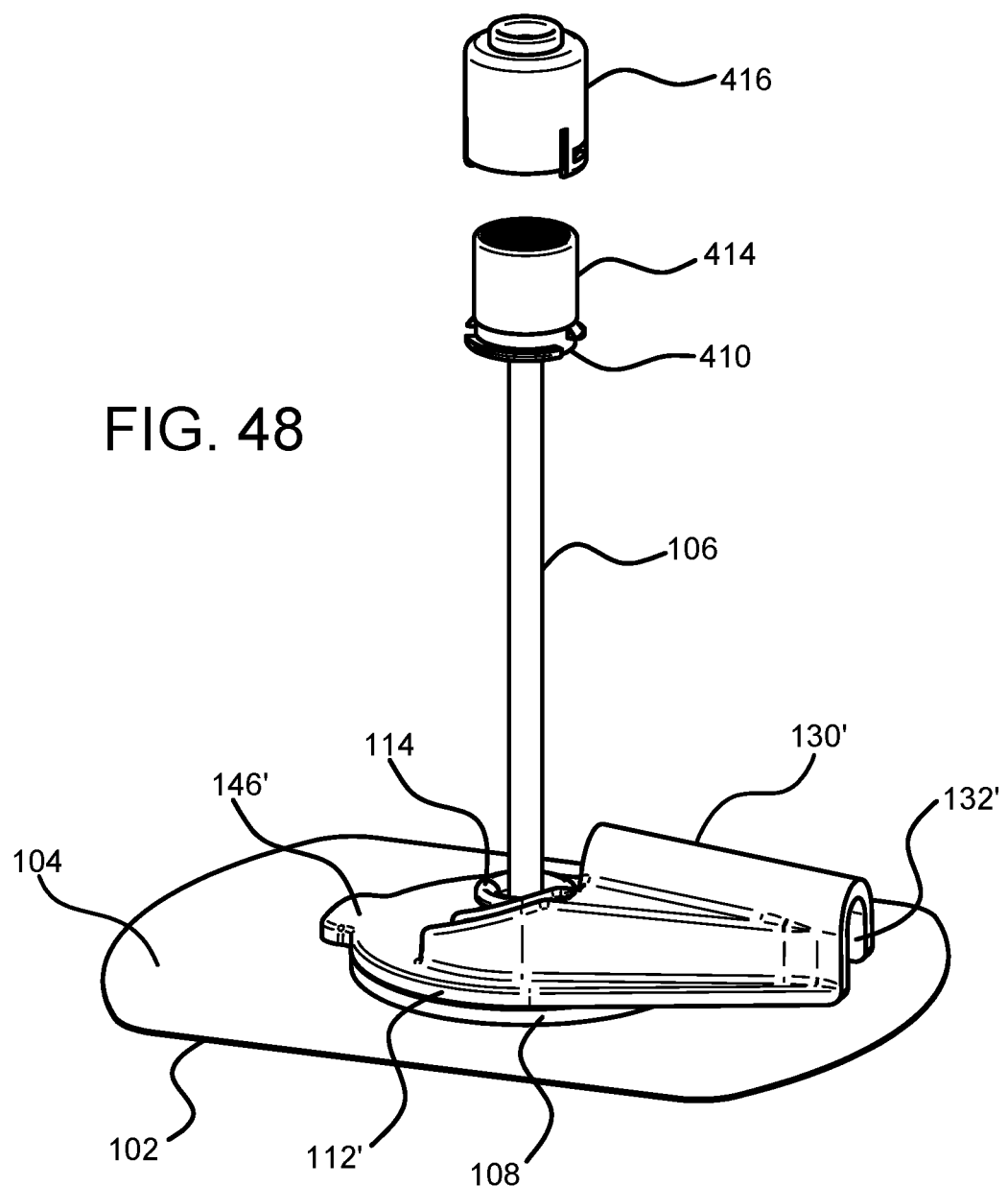
FIG. 48 illustrates another stage of assembly of a distal collar of the medical tube securement device during manufacture of the medical tube securement device of FIG. 39.
Figure 49:
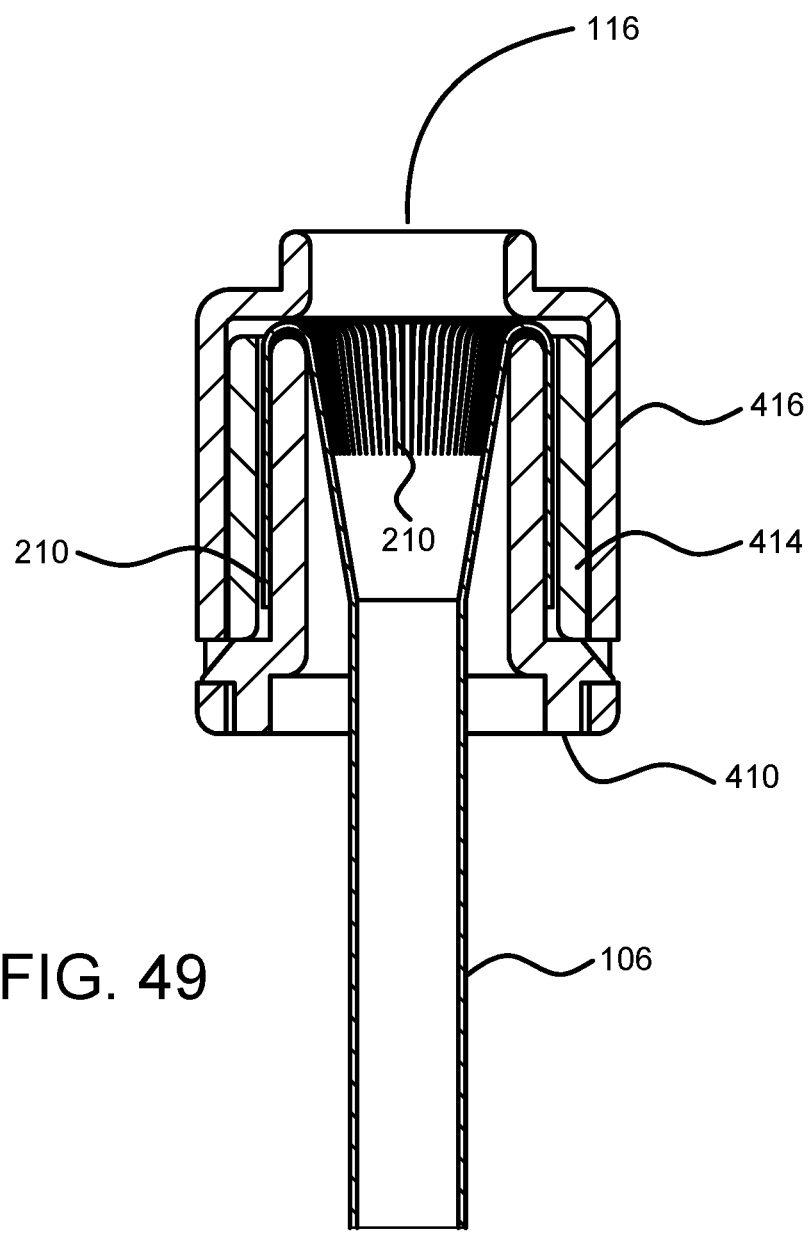
FIG. 49 is a partial sectional view of the assembled medical tube securement device of FIG. 1 showing features of the assembled distal collar retaining a distal end of the securement sleeve.

FIG. 43 shows a waterfall collar 410 disposed over the securement sleeve 106 of the second preliminary product form 200' during assembly of the distal collar 110' of the securement device 100" of FIGS. 39-42. As illustrated in FIG. 43, a leading edge of a flaring tool 412 is inserted into the distal end portion 210 of the securement sleeve 106. The flaring tool 412 is advanced into the securement sleeve 106 to flare the distal end portion 210 of the securement sleeve 106 as illustrated in the sequential processing illustrated in FIGS. 44 and 45. After the distal end portion 210 of the securement sleeve 106 has been flared open as shown in FIG. 45 by full advancement of the flaring tool 412, then the waterfall collar 410 is positioned adjacent the flared distal end portion 210 of the securement sleeve 106 and a waterfall sleeve 414 is advanced over the flaring tool 412 to engage the flared distal end portion 210 of the securement sleeve 106, as illustrated in FIG. 45. As the waterfall sleeve 414 is further advanced over the waterfall collar 410, as illustrated in FIG. 46, the flared distal end portion 210 of the securement sleeve 106 is folded over the securement collar 410 in a waterfall configuration around the exterior of the waterfall collar 410, and the waterfall sleeve 414 is advanced over the waterfall collar 410, and over the folded portion of the distal end portion 210 of the securement collar 410, until the advancing end of the waterfall sleeve 414 is adjacent a bottom lip portion of the waterfall collar 410, and the flaring tool 412 is then removed from the securement sleeve 106, as illustrated in FIG. 47. As illustrated in FIG. 48, a waterfall retainer 416 is then disposed over the waterfall sleeve and engaged with and connected to the waterfall collar 410 to form the final assembled distal collar 110' for the securement device 100". The finished configuration of the distal collar 110' is illustrated in the partial sectional view of FIG. 49, showing the flared distal end portion 210 of the securement sleeve 106 folded over and disposed between the waterfall collar 410 and the waterfall sleeve 414 and with the waterfall retainer 416 engaged with the waterfall collar. Completion of manufacture of the securement device 100" may then proceed with the addition of the absorbent pad 150, similar to as illustrated in FIG. 34, and a securement product may be formed by adding a peelable backing, for example as provided by the peelable backing sheets 228*a,b* similar to the illustration in FIG. 34.

Figure 50:
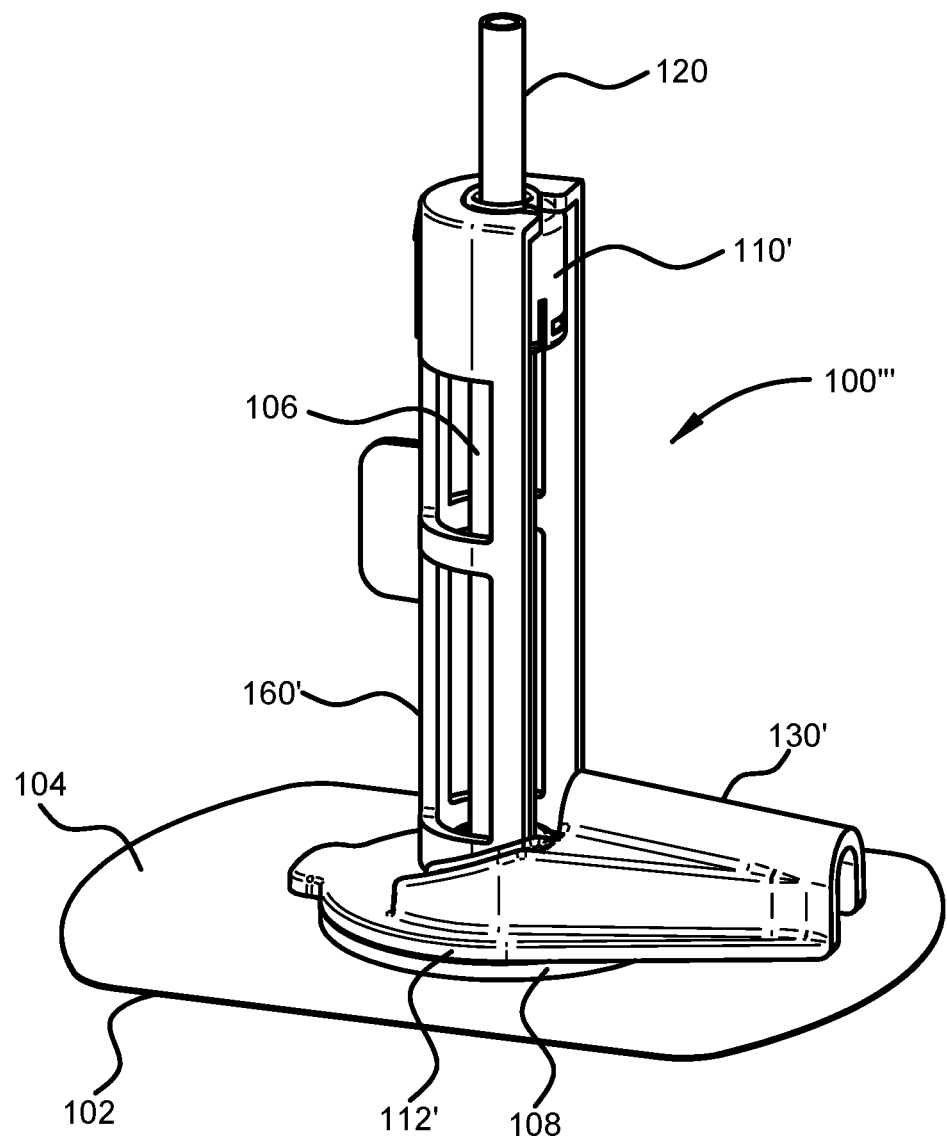
FIG. 50 is a perspective view of a variation of the medical tube securement device of FIG. 39 including a compression retainer, and shown with a medical tube received through the securement sleeve in a compressed state.
Figure 51:
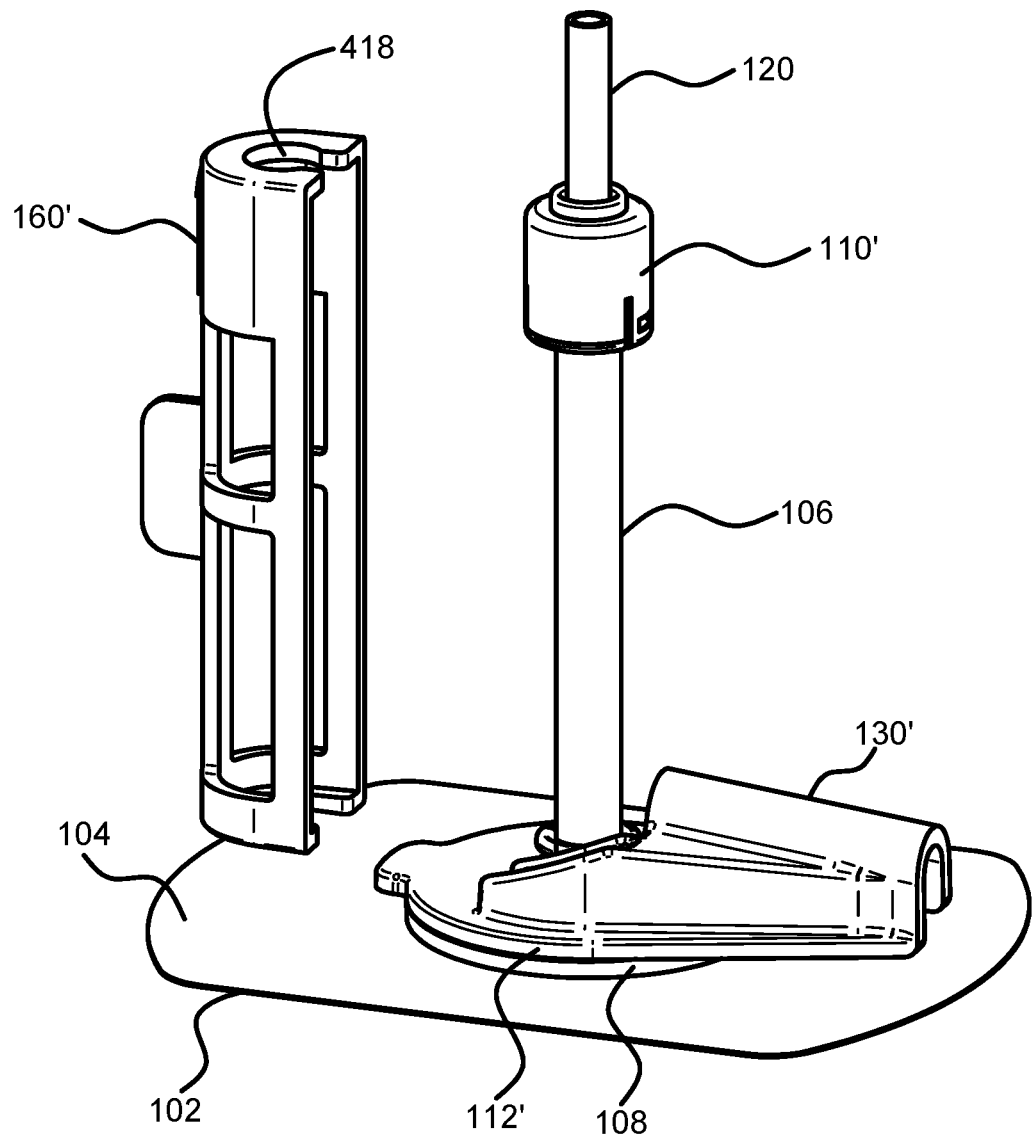
FIG. 51 is a perspective view of the variation of the medical tube securement tube of FIG. 50, shown after removal of the compression retainer to grip the medical tube in the securement sleeve, and shown with a medical tube received through and gripped by the securement sleeve after release from the compressed state.

The securement device 100" may also be combined with a compression retainer, similar to the configuration of the securement device 100' illustrated in FIG. 18-20. With reference to FIG. 50, together with FIGS. 39-49, a securement device 100—is illustrated, in which a compression retainer 160' is engaged with the distal collar 110' and the extension portion 114 of the rotating member 112' to retain the securement sleeve 106 in a compressed configuration with the cross-sectional area of the tube passage 116 through the securement sleeve 106 in an enlarged configuration to receive insertion of a medical tube for positioning within the securement sleeve 106. The compression retainer 160' is similar in design to the compression retainer 160 of FIGS. 18-20, but includes a keyhole cutout in the top to snap around a correspondingly shaped top projection on the distal collar 110' to more securely hold the securement sleeve in the compressed configuration for application of the securement device 100''' to a patient during a medical procedure. In FIG. 50, the securement device 100''' is illustrated with the medical tube 120 disposed through the securement sleeve 106 in the compressed configuration. FIG. 51 shows the securement device 100—after disengagement of the compression retainer 160', permitting the securement sleeve to lengthen and grip the medical tube 120 for securement of the medical tube 120 to the securement sleeve 106.

Exemplary Implementation Combinations.

Some other contemplated embodiments of implementation combinations for various aspects of this disclosure, with or without additional features as disclosed above or elsewhere herein, are summarized in the numbered paragraphs presented below, and in the appended claims:

1. In some embodiments, a securement device is provided to secure to a patient a medical tube when inserted into the patient, the securement device comprising:
   an attachment pad configured to interface with skin of a patient for attachment of the securement device to the skin, and preferably the attachment pad has an adhesive surface to adhere the attachment pad to a surface of the skin;
   a variable-length securement sleeve having a proximal end and a distal end at a longitudinal end opposite the proximal end, the securement sleeve being coupled to the attachment pad through a coupling structure adjacent the proximal end of the securement sleeve;
   a tube passage configured to receive therethrough a medical tube for securement to a patient, the tube passage extending longitudinally through the securement sleeve; and
   the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and the length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device.

Bent Sleeve Retainer

2. The securement device of paragraph 1, comprising a bent sleeve holder selectively engageable and disengageable with the securement sleeve to selectively retain and not retain the securement sleeve in a bent configuration in which the securement sleeve has a bend in which the tube passage is correspondingly bent, and preferably in the bent configuration the bend biases a portion of the sleeve distal of the bend toward the attachment pad.

3. The securement device of paragraph 2, wherein in the bent configuration the securement sleeve is bent by an angle of at least 60°, preferably at least 80° and more preferably at least 90° between the distal end and the proximal end of the securement sleeve.

4. The securement device of either one of paragraph 2 or paragraph 3, wherein in the bent configuration, at least a longitudinal portion of the securement portion of the securement sleeve is bent.

5. The securement device of any one of paragraphs 2-4, wherein the bent sleeve holder engages at least a longitudinal portion of the securement portion of the securement sleeve when the securement sleeve is engaged with the bent sleeve holder to retain the securement sleeve in the bent configuration.

6. The securement device of any one of paragraphs 2-5, wherein the bent sleeve holder comprises a movable member that is movable between a first configuration in which the securement member is not retained in the bent configuration and a second configuration in which the movable member contacts and biases the securement sleeve in the bent configuration.

7. The securement device of paragraph 6, comprising a lock configured to retain the movable member in the second configuration when the movable member is repositioned from the first configuration to the second configuration.

8. The securement device of paragraph 7, wherein the lock is selectively releasable to permit repositioning of the movable member from the second configuration to the first configuration.

9. The securement device of any one of paragraphs 2-5, wherein the bent sleeve holder comprises a retaining channel into which a corresponding portion of the securement sleeve is receivable in a received position to retain the securement sleeve in the bent configuration.

10. The securement device of paragraph 9, wherein the bent sleeve holder comprises flexible tabs that flex when the corresponding portion of the securement sleeve is inserted into the channel to be received in the channel in the received position to retain the securement sleeve in the bent configuration and when the corresponding portion of the securement sleeve is removed from the channel to release the securement sleeve from the bent configuration.

11. The securement device of paragraphs 10, wherein the flexible tabs, and optionally the entire bent sleeve holder, are made of a polymeric material of construction, preferably a thermoplastic elastomer, and optionally selected from the group consisting of thermoplastic polyurethanes, thermoplastic vulcanizates and combinations thereof.

12. The securement device of either one of paragraph 10 or paragraph 11, wherein the flexible tabs, and optionally the entire bent sleeve holder, are made of a material of construction having a hardness in a range of from 60 to 90 Shore A durometer.

13. The securement device of either one of paragraph 11 or paragraph 12, wherein the bent sleeve holder comprises a channel member comprising the flexible tab portions, and the channel member is made of the material of construction.

13.1 The securement device of any one of paragraphs 9-13, wherein the retaining channel is open facing away from the attachment pad.

13.2 The securement device of any one of paragraphs 9-13, wherein retaining channel is open facing toward the attachment pad.

14. The securement device of any one of paragraphs 2-13.2, wherein the bent sleeve holder is rotationally mounted and rotatable to different radial positions relative to the attachment pad, preferably with the bent sleeve holder maintaining a constant standoff from the attachment pad at all said radial positions; and optionally the different radial positions are radially spaced with a radial spacing of no more than 30 degrees, preferably no more than 15 degrees, and optionally of at least 5 degrees, and preferably the proximal end of the securement sleeve is in a fixed position relative to the attachment pad and rotation of the bent sleeve holder relative to the attachment pad also rotates the bent sleeve holder relative to the securement sleeve.

15. The securement device of paragraph 14, wherein the radial positions are radially spaced about a longitudinal axis of the tube passage through the attachment pad.

16. The securement device of either one of paragraph 14 or paragraph 15 wherein the attachment pad has a proximal side to be disposed facing the skin of a patient during use and the radial positions are radially spaced about an axis perpendicular to a face of the proximal side of the attachment pad.

17. The securement device of any one of paragraphs 14-16, comprising a radial positioning lock to selectively lock the bent sleeve holder at different ones of the radial positions.

18. The securement device of any one of paragraphs 14-17, wherein the bent sleeve holder is rotatable by at least 90 degrees about an axis of rotation, preferably at least 180 degrees and more preferably at least 360 degrees.

19. The securement device of any one of paragraphs 14-18, comprising a base member and a rotating member that is rotatable relative to the base member, and wherein the bent sleeve holder is supported on the rotating member, and preferably the base member has a fixed orientation relative to the attachment pad, wherein rotation of the rotating member relative to the base member results in rotation of the rotating member also relative to the attachment pad.

20. The securement device of paragraph 19, wherein:
the base member and the rotating member comprise corresponding interlocking first and second lock structures that are selectively engageable to lock the radial position of the rotating member at different ones of the radial positions.

21. The securement device of paragraph 20, wherein the rotating member has at least a portion that is elastically deformable to disengage the first and second lock structures and to permit repositioning of the bent sleeve holder between different said radial positions.

22. The securement device of any one of paragraphs 19-21, wherein the rotating member, and optionally the base member, is made of a polymeric material of construction, preferably a thermoplastic elastomer, and optionally selected from the group consisting of thermoplastic polyurethanes, thermoplastic vulcanizates and combinations thereof, and wherein both the rotating member and the base member are made of a said polymeric material of construction, the properties (e.g., hardness) of each said polymeric material of construction of the rotating member and the base member can be the same or different.

23. The securement device of paragraph 22, wherein the rotating member, and optionally the base member, is made of a material of construction having a hardness in a range of from 60 to 90 Shore A durometer.

24. The securement device of any one of paragraphs 19-23, wherein the bent sleeve holder and the rotating member are in a single molded piece, preferably a single injection molded piece, and preferably the single molded piece is made of a single material of construction.

25. The securement device of any one of paragraphs 19-24, wherein the base member comprises an extension portion extending through an aperture in the rotating member, and the rotating member is rotatable about the extension portion, and optionally the rotating member is retained in and rotatable relative to a circular groove track extending around a perimeter of the extension portion.

26. The securement device of any one of paragraphs 19-24, wherein the base member is a molded piece, preferably an injection molded piece, and optionally the molded piece of the base member is made of a single material of construction.

27. The securement device of any one of paragraphs 2-26, wherein:
  the bent sleeve holder is configured to retain the securement sleeve in the bent configuration with the entire length of the tube passage in the securement sleeve disposed within a standoff distance from a proximal surface plane of the attachment pad;
  a minimum insertion cross-section of the tube passage in the securement portion, transverse to a longitudinal path of the tube passage through the securement portion, varies in size as the length of the securement sleeve is varied, the minimum insertion cross-section having a maximum cross-dimension (e.g., diameter in preferred implementations when the minimum insertion cross-section is circular) that correspondingly varies as the size of the minimum insertion cross-section is varied;
  the standoff distance is not greater than 10 times, preferably not greater than 7 times and more preferably not greater than 6 times, a relaxed-state maximum cross-dimension of the minimum insertion cross-section of the tube passage through the securement sleeve, and optionally is preferably at least 3 times or even at least 4 times the relaxed-state maximum cross-dimension; and
  the relaxed-state maximum cross-dimension is the maximum cross-dimension of the minimum insertion cross-section when the securement sleeve is in a relaxed state not under longitudinally-applied compression or tension. As will be appreciated, the relaxed-state maximum cross dimension will typically not correspond to the bent configuration. As will be appreciated, such relaxed-state maximum cross-dimension will typically be slightly smaller than a maximum outer cross-dimension (e.g., diameter) of an outer cross-section of a portion of the medical tube that the securement sleeve is designed to receive for securement in the securement portion. In one example, such a standoff distance for a sleeve designed to retain a 5 millimeter diameter medical tube can preferably be about 24 millimeters.

Compression Retainer

28. The securement device of any one of paragraphs 1-27, comprising a compression retainer disposed to retain the securement sleeve in a compressed configuration with the securement portion of the securement sleeve under longitudinally-applied compression with the cross-sectional area in an expanded configuration to receive therethrough the medical tube.

29. The securement device of paragraph 28, wherein the compression retainer is manipulable to release the securement portion from the longitudinally-applied compression to lengthen the securement sleeve and to contract the cross-sectional area relative to the expanded configuration, to permit the securement portion to grip a said medical tube when disposed through the tube passage through the securement portion.

30. The securement device of paragraph 29, wherein the compression retainer is removable to release the securement portion from the longitudinally-applied compression and permit the securement sleeve to lengthen and the cross-sectional area to contract relative to the compressed configuration.

31. The securement device of any one of paragraphs 28-30, comprising a distal collar adjacent the distal end of the securement sleeve and a base structure adjacent a proximal end of the securement sleeve, and wherein the compression retainer engages the distal collar and the base structure to retain the securement sleeve in the compressed configuration.

32. The securement device of any one of paragraphs 28-31, comprising the rotating member and the base member according to any one of paragraphs 19-26, and wherein:
  the base structure comprises the base member and the base member comprises the extension portion of paragraph 25 extending through the aperture in the rotating member with the rotating member rotatable about the extension portion; and
  the compression retainer engages the extension portion when the securement sleeve is in the compressed configuration.

33. The securement device of any one of paragraphs 28-32, wherein when the securement sleeve is in the compressed configuration the tube passage through the securement sleeve, and preferably all of the tube passage through the securement device, is maintained in a straight longitudinal configuration.

34. The securement device of paragraph 33, wherein when the compression retainer is manipulated to release the securement sleeve from the compressed configuration, the tube passage is released from the straight longitudinal configuration and the securement sleeve becomes amenable to being bent to produce a corresponding bend in the tube passage to bend a said medical tube when disposed through the tube passage.

35. The securement device of any one of paragraphs 28-34, wherein:
  the securement sleeve has a released configuration when the securement sleeve is released from the compression configuration with nothing disposed in the tube passage through the securement sleeve, the length of the securement sleeve being larger in the released configuration than in the compressed configuration; and
  a minimum insertion cross-section of the tube passage in the securement portion, transverse to a longitudinal path of the tube passage through the securement portion, varies as the length of the securement sleeve is varied, wherein the minimum insertion cross-section is larger in the compressed configuration than in the released configuration.

36. The securement device of paragraph 35, wherein:
  in the compressed configuration the minimum insertion cross-section is at least 10 percent larger than in the released configuration.

37. The securement device of either one of paragraph 35 or paragraph 36, wherein:
  the minimum insertion cross-section has a maximum cross-dimension, and preferably the minimum insertion cross-section is circular and the maximum cross-dimension is a diameter of the circular minimum insertion cross-section; and
  in the released configuration, the maximum cross-dimension of the minimum insertion cross-section in the released configuration is at least 0.5 millimeter smaller than, preferably at least 1.0 millimeter smaller than, and more preferably at least 1.5 millimeters smaller than, in the compressed configuration, and optionally is not more than 4 millimeters smaller than, and alternatively optionally not more than 3 millimeters smaller than, in the compressed configuration;

optionally, the maximum cross-dimension of the minimum insertion cross section is in a range of from 2.5 to 26 millimeters when the securement sleeve is in the compressed configuration.

38. The securement device of any one of paragraphs 35-37, wherein:
the minimum insertion cross-section has a maximum cross-dimension, and preferably the minimum insertion cross-section is circular and the maximum cross-dimension is a diameter of the circular minimum insertion cross-section;
the minimum insertion cross-section is configured to receive in the compressed configuration and retain in the released configuration a corresponding outer cross-section of a medical tube, the outer cross-section having a maximum outer cross-dimension (e.g., outer diameter of a preferred medical tube with a circular outer cross-section);
in the released configuration, the maximum cross-dimension of the minimum insertion cross-section is at least 0.5 millimeter smaller than, preferably at least 1.0 millimeter smaller than, and more preferably at least 1.5 millimeter smaller than, the maximum outer cross-dimension of the outer cross-section of the medical tube, and optionally not more than 4 millimeters smaller than, or alternatively optionally not more than 3 millimeters smaller than, the maximum outer cross-dimension of the outer cross-section of the medical tube.

Proximal Sleeve Coupling

39. The securement device of any one of paragraphs 1-38, wherein the coupling of the securement sleeve to the attachment pad comprises flared proximal end material of the securement sleeve sandwiched between a first securement member and a second securement member, optionally with the flared proximal end material of the securement sleeve flared at an angle of at least 75 degrees, and preferably at least 90 degrees, relative to an adjacent unflared portion of the securement sleeve, and preferably the flared proximal end material of the securement sleeve is sandwiched between opposing surfaces, preferably opposing parallel surfaces, of the first securement member and the second securement member.

40. The securement device of paragraph 39, wherein the flared proximal end material of the securement sleeve is adhered to at least one, and preferably both, of the first securement member and the second securement member, optionally by adhesive disposed between the first securement member and the second securement member.

41. The securement device of paragraph 40, comprising the adhesive disposed between the first securement member and the second securement member, and wherein the adhesive is a pressure-sensitive adhesive, and optionally the pressure-sensitive adhesive is selected from the group consisting of acrylic adhesives, silicone adhesives and combinations thereof.

42. The securement device of either one of paragraph 40 or paragraph 41, wherein the adhesive comprises;
an adhesive layer applied to at least one surface selected from the group consisting of the first surface of the first securement member and the second surface of the second securement member, and preferably the adhesive layer comprises pressure sensitive adhesive; and
optionally the adhesive comprises:
a first adhesive layer on a first surface of the first securement member and disposed toward the flared end material of the securement sleeve;
a second adhesive layer on a second surface of the second securement member facing; and
wherein the first adhesive layer and second adhesive layer are optionally of the same adhesive composition and alternatively optionally are of different adhesive compositions, and preferably each of the first and second adhesive layers comprise pressure-sensitive adhesive.

43. The securement device of any one of paragraphs 39-42, wherein the first securement member is the attachment pad.

44. The securement device of any one of paragraphs 39-43, wherein the second securement member is the base member of any one of paragraphs 19-26.

Distal Collar Assembly

45. The securement device of any one of paragraphs 1-44, wherein a distal end portion of the securement sleeve is retained by a distal collar assembly.

46. The securement device of paragraph 45, wherein the distal collar assembly comprises a collar member with a collar nipple disposed inside the distal end portion of the securement sleeve and a retaining member disposed over the distal end portion of the securement sleeve biasing a sleeve wall of the distal end portion toward the collar nipple.

46.1 The securement device of paragraph 45, wherein the distal collar assembly comprises a waterfall securement configuration.

46.2 The securement device of paragraph 46.1, wherein the distal collar assembly comprises a waterfall collar through which a portion of the securement sleeve is disposed and with a flared distal end portion of the securement sleeve folded over an exterior of the waterfall collar.

46.3 The securement device of paragraph 46.2, wherein the distal collar assembly comprises a waterfall sleeve disposed over at least a portion of the waterfall collar with the flared distal end portion of the securement sleeve folded over the exterior or the waterfall collar disposed between the waterfall collar and the waterfall sleeve.

46.4 The securement device of paragraph 46.3, wherein the distal collar assembly comprises a waterfall retainer disposed over the waterfall sleeve and engaged with the waterfall collar.

47. The securement device of any one of paragraphs 45-46.4, comprising the compression retainer of any one of paragraphs 28-38 retaining the securement sleeve in the compressed configuration with the compression retainer engaging the distal collar assembly.

Attachment Pad and Absorbent Portion

48. The securement device of any one of paragraphs 1-47, wherein the attachment pad comprises an absorbent portion configured to absorb exudate during use of the securement device;
optionally the attachment pad comprises a structural sheet and a distal side of the absorbent portion, to be disposed away from a patient during use of the securement device, is covered by the structural sheet, and further optionally the attachment pad comprises adhesive over at least a portion of a proximal side of the structural sheet for adherence of the attachment pad to the skin of a patient.

49. The securement device of paragraph 48, wherein the tube passage extends through an aperture in the absorbent portion.

50. The securement device of either one of paragraph 48 or paragraph 49, wherein the absorbent portion has a proximal face to be disposed toward the patient when the securement device is attached to the patient, and optionally the proximal face of the absorbent portion includes a fluid communication surface for fluid communication with the patient, and optionally in contact with the patient, when the securement device is attached to the skin of the patient.

51. The securement device of any one of paragraphs 48-50, wherein the attachment pad comprises an adhesive surface to adhere the attachment pad to the skin of a patient, and optionally the adhesive surface is configured to adhere the adhesive pad to the skin completely around an outer periphery of the proximal side of the absorbent portion configured to be disposed toward the patient.

52. The securement device of paragraph 51, wherein;
the attachment pad comprises a perforated layer of adhesive covering a least a portion of the proximal face of the absorbent portion; and
perforations through the perforated layer of adhesive provide fluid communication passages across the perforated layer of adhesive, providing for fluid communication of exudate from the patient across the perforated layer of adhesive to be absorbed by the absorbent portion when the attachment pad is attached to the skin of the patient.

53. The securement device of any one of paragraphs 48-52, wherein the absorbent portion has an absorbent capacity of at least 500% by weight, determined as absorption to saturation of 0.9% wt./vol. saline (isotonic saline) relative to the weight of the absorbent portion.

54. The securement device of any one of paragraphs 48-52, wherein the absorbent portion comprises absorbent material, optionally selected from the group consisting of hydrophilic polymers, natural fibers (e.g., cotton), hygroscopic gels (e.g., hydrogels) and combinations thereof.

55. The securement device of any one of paragraphs 48-54, wherein the absorbent portion has an absorbent capacity to absorb at least 1 milliliter, determined as absorption to saturation of 0.9% wt./vol. saline (isotonic saline).

56. The securement device of any one of paragraphs 48-55, wherein the absorbent portion comprises a proximal face configured to be disposed toward the skin of a patient, and preferably with at least a portion of the proximal face configured to contact the skin, when the securement device is attached to the skin.

57. The securement device of paragraph 56, wherein the proximal face of the absorbent portion has a surface area of at least 4 square centimeters, and optionally up to 18 square centimeters.

58. The securement device of either one of paragraph 56 or paragraph 57, wherein:
optionally, the attachment pad is in the absence of adhesive covering any portion of proximal face of the absorbent portion; and
alternatively optionally, the attachment pad comprises a adhesive covering a portion of but not covering another portion of the proximal face of the absorbent portion, and preferably with this alternative option the adhesive over a portion of the proximal face is in a perforated layer of adhesive on the proximal face with perforations through the perforated layer of adhesive comprising some or all of the other portion of the proximal face not covered by the adhesive and wherein the perforations through the perforated layer of adhesive provide fluid communication across the perforated layer of adhesive to proximal face of the absorbent portion, providing for flow of exudate from the patient across the perforated layer of adhesive to be absorbed by the absorbent portion when the attachment pad is attached to the skin of the patient.

59. The securement device of any one of paragraphs 56-58, wherein the proximal face has a circular outer perimeter.

60. The securement device of any one of paragraphs 56-59, comprising an opening in the proximal face of the absorbent portion for the tube passage.

61. The securement device of any one of paragraphs 56-60, wherein the proximal face extends in a plane perpendicular to a longitudinal direction of the tube passage through the absorbent portion.

61.1 The securement device of any one of paragraphs 48-61, wherein the absorbent portion comprises an antimicrobial agent, and optionally the absorbent portion is configured for fluid communication between the patient and the antimicrobial agent when the attachment pad is attached to the skin of the patient.

61.2 The securement device of any one of paragraphs 1-61.1, wherein the attachment pad comprises an antimicrobial agent, optionally in an adhesive layer of the attachment pad.

61.3 The securement device of paragraph 61.2, wherein the attachment pad is configured for fluid communication between the patient and the antimicrobial agent with the attachment pad is attached to the skin of the patient.

Other Sleeve Features

62. The securement device of any one of paragraphs 1-61.3, wherein as coupled to the attachment pad, the proximal end of the securement sleeve has a fixed position relative to the attachment pad, and optionally the distal end of the securement sleeve does not have a fixed position relative to the attachment pad.

63. The securement device of any one of paragraphs 1-62, wherein the securement sleeve is configured to vary a maximum cross-dimension of the cross-sectional area (e.g., diameter of a circular cross-section) by at least 10 percent relative to a maximum expanded size of the cross-sectional area.

64. The securement device of any one of paragraphs 1-63, wherein the securement sleeve is configured to vary a maximum cross-dimension of the cross-sectional area (e.g., diameter of a circular cross-section) by at least 1 millimeter and preferably by at least 1.5 millimeters.

65. The securement device of any one of paragraphs 1-64, wherein
the securement sleeve is configured to retain in the securement portion a portion of a medical tube having a maximum outer cross-dimension, transverse to a longitudinal direction of the medical tube, and preferably the outer cross-section of the medical tube is a circular cross-section and the maximum outer cross-dimension is an outer diameter of the circular cross-section of the medical tube; and
the securement sleeve is configured to vary a maximum cross-dimension of the cross-sectional area (e.g., diameter of a circular cross-section) at least over a range of from a lower limit of at least 1 millimeter smaller than, and optionally at least 1.5 millimeters smaller than, the maximum outer cross-dimension and having an upper limit of at least 1 millimeter larger than, and optionally at least 1.5 millimeters larger than, the maximum outer cross-dimension, and optionally the lower limit is not more than 2 millimeters smaller than the maximum outer cross-dimension and, optionally, the upper limit is not more than 2 millimeters larger than the maximum outer cross-dimension.

66. The securement device of any one of paragraphs 1-65, wherein the cross-sectional area of the tube passage is circular.

67. The securement device of any one of paragraphs 1-66, wherein the securement portion of the securement sleeve is made of a textile (e.g., with a braided, woven, knitted, crocheted, knotted, tatted, felted or bonded structure with interlacing fibers), and optionally the securement portion is coated with and/or doped to release a sanitary component selected from the group consisting of an antimicrobial agent and/or an antiseptic.

68. The securement device of paragraph 67, wherein the textile is made of a material of construction selected from the group consisting of metallic materials, polymeric materials and combinations thereof; and preferably the material of construction comprises a polymeric material, optionally the material of construction comprises a polymeric material selected from the group consisting of polyethylene terephthalate, nylon and polyester.

69. The securement device of any one of paragraphs 1-68, wherein;

the securement sleeve is configured to retain in the securement portion a portion of a medical tube having a maximum outer cross-dimension, transverse to a longitudinal direction of the medical tube, and preferably the medical tube has a circular cross-section and the outer cross-dimension is an outer diameter of the circular cross-section; and the securement portion of the securement sleeve has a length longitudinally along the securement sleeve of at least 5 times, preferably at least 10 times and more preferably at least 12 times, the maximum outer cross-dimension, and optionally up to 30 times, preferably up to 25 times and more preferably up to 20 times, the maximum outer cross-dimension, with one preferred range for 5 millimeter outer diameter medical tube being from 6 to 10 centimeters.

Products and Kits

70. A medical tube securement product, comprising:

the securement device of any one of paragraphs 1-69, wherein the attachment pad comprises the adhesive surface configured to adhere the attachment pad to the skin of a patient; and a peelable backing adhered to and covering the adhesive surface and configured to be peeled from the adhesive surface to expose the adhesive surface for adherence of the attachment pad to the skin of a patient; and optionally the adhesive surface comprises an acrylic adhesive, and optionally the adhesive is impregnated with an antimicrobial agent.

71. The product of paragraph 70, wherein the securement device comprises the absorbent portion of any one of paragraphs 56-61.1, and wherein the peelable backing covers a proximal face of the absorbent portion and is configured to expose at least a portion of, and optionally all of, the proximal face of the absorbent portion when the peelable backing is peeled from the adhesive surface, and optionally the peelable backing contacts the absorbent portion.

72. The product of either one of paragraph 70 or paragraph 71, wherein the adhesive surface of the attachment pad has a surface area equal to the surface area of the adhesive pad of at least 25, and preferably at least 45 square centimeters, and preferably in a range having an upper limit of 90 square centimeters.

73. The product of any one of paragraphs 70-72, wherein the peelable backing is not adhered to the proximal face of the absorbent portion.

74. The product of any one of paragraphs 70-73, comprising a hermetically-sealed enclosure in which is disposed the securement device with the peelable backing adhered to the adhesive surface of the attachment pad, preferably with the securement device in the enclosure and the interior environment in the enclosure being sterile.

75. A medical tube securement kit, optionally a medical drain tube securement kit, comprising:

the securement device of any one of paragraphs 1-69, optionally in the medical tube securement product of any one of paragraphs 70-74 and alternatively optionally not in the medical tube securement product of any one of paragraphs 70-74; and at least one additional component selected from the group consisting of:

(i) a medical tube configured to be translatable through the tube passage when the cross-sectional area of the tube passage in the securement portion of the securement sleeve is in an expanded configuration and to be gripped and held by the securement portion when the cross-sectional area of the tube passage in the securement portion of the securement sleeve is in a contracted configuration, and optionally with an introduction trocar for the medical tube;

(ii) a tissue penetration instrument configured to penetrate through tissue to provide a surgical path sized for insertion of a medical tube to be secured by the securement device, optionally selected from the group consisting of a trocar, a tendon passer and combinations thereof;

(iii) a fluid collection system configured to fluidly connect with a distal end of a medical tube to be secured by the securement device to collect biological fluid draining through the medical tube, optionally the fluid collection system comprises a collection container configured to collect and retain collected biological fluid and alternatively or additionally optionally the fluid collection system comprises a fluid evacuation container configured to initially collect biological fluid and that is compressible to evacuate biological fluid from the evacuation container (optionally into another fluid container) and apply a vacuum suction to the medical tube (e.g., a bulb evacuator or a bellows-type evacuator, such as for example a HEMOVAC® compact evacuator);

(iv) an absorbent pad (separate from the securement device) configured to absorb exudate prior to or as a consequence of insertion of a medical drain to be secured by the securement device, optionally having any feature or features described for an absorbent portion of the securement device;

(v) an antiseptic wipe (e.g., alcohol wipe) to clean around a location on a patient where a medical tube is to be inserted to be secured by the securement device;

(vi) skin preparation wipes to prepare skin of a patient for attachment of the attachment pad of the securement device, optionally to prepare skin for enhanced adhesion between the attachment pad of the securement device and the skin;

(vii) the compression retainer of any one of paragraphs 28-38 and 47, whether or not in place to retain the securement sleeve in the compressed configuration (e.g., the compression retainer can be included in the kit as a component separate from the securement device and which can be installed on the securement device as needed to retain the securement sleeve in the compressed configuration, or the kit can include the securement device including the compression retainer pre-installed with the securement sleeve held in the compressed configuration);

(viii) an adhesion component to apply to the skin to assist adhesion of the attachment pad to the skin (e.g., benzoin-containing formulations, Mastosol® liquid adhesive), optionally in a wipe or in an ampule;

(ix) an antimicrobial agent for antimicrobial treatment of skin of a patient in a vicinity of the where the securement device is or is to be attached to the skin, optionally the antimicrobial agent is provided in a form selected from the group consisting of a cream, ointment, wipe and combinations thereof; and (x) combinations of any two, three, four, five, six, seven, eight or nine of items (i)-(ix). When a member of any of (i)-(ix) is included in a kit, the kit will include at least one such member, but may include a plurality of such members (e.g., a plurality of absorbent pads, antiseptic wipes, skin preparation wipes, ampules or wipes with an adhesion component, or wipes or other forms with an antimicrobial).

76. The kit of paragraph 75, wherein the medical tube is disposed through the tube passage.

77. The kit of paragraph 76, wherein the cross-sectional area in the securement portion is in an expanded configuration in which the medical tube is not gripped and held by the securement portion of the securement sleeve.

78. The kit of paragraph 76, wherein the cross-sectional area in the securement portion is in the contracted configuration with the medical tube gripped and held by the securement portion of the securement sleeve.

79. The kit of paragraph 78, wherein the medical tube is held by the securement portion up to a tension load applied to the tube distally of a distal end of the securement portion of at least 7 Newtons, and preferably at least 10 Newtons.

80. The kit of paragraph 79, wherein the securement sleeve is retained in a bent configuration with a bend in the securement sleeve that produces a corresponding bend in the tube passage through the securement sleeve and a corresponding bend in the medical tube disposed through the tube passage.

81. The kit of paragraph 80, wherein at least a portion of the bend in the tube passage is in the securement portion of the securement sleeve with the securement portion gripping and holding a bent portion of the medical tube.

82. The kit of paragraph 81, wherein in the bent configuration the medical tube is held by the securement portion up to a tension load applied to the tube distally of a distal end of the securement portion of at least 10 Newtons, and preferably at least 15 Newtons.

83. The kit of either one of paragraph 81 or paragraph 82, wherein the securement sleeve is releasable from being held in the bent configuration, and in the bent configuration the medical tube is held by the securement portion up to a tension load applied to the medical tube of at least 20 percent larger, and preferably at least 30 percent larger, than a corresponding applied tension load when the securement sleeve is released from the bent configuration, and optionally not larger than 100 percent larger than the corresponding applied tension load when the securement sleeve is released from the bent configuration.

84. The kit of paragraph 83, wherein the securement sleeve is engaged with the bent sleeve holder of the securement device of any one of paragraphs 2-27 and bent sleeve holder retains the securement sleeve in the bent configuration.

Method of Use

85. A method of securing a medical tube to a patient with a securement device having a variable-length securement sleeve and a tube passage through the securement sleeve to receive a medical tube for securement, wherein the securement sleeve includes a securement portion and in the securement portion a cross-sectional area of the tube passage transverse to a longitudinal path of the tube passage expands as the securement sleeve is shortened and contracts as the securement sleeve is lengthened and the length of the securement sleeve is adjustable to expand the cross-sectional area to receive the medical tube for translation through the tube passage and to contract the cross-sectional area to grip the medical tube in the tube passage in the securement portion to secure the medical tube to the securement device, the method comprising:
with a medical tube extending through the tube passage and into the body of a patient, gripping the medical tube in the tube passage with the securement portion of the securement sleeve; and
optionally, the securement device is according to any one of paragraphs 1-69, and further optionally the securement device is provided in a product or kit according to any one of paragraphs 70-84.

86. The method of paragraph 85, comprising, with the medical tube gripped by the securement portion in the tube passage, bending the securement sleeve to a bent configuration to impart a corresponding bend in the medical tube in the tube passage in the securement sleeve.

87. The method of paragraph 86, wherein in the bent configuration the securement sleeve, and the medical tube in the tube passage in the securement sleeve, is bent by an angle of at least 60°, preferably at least 80° and more preferably at least 90° between longitudinal ends of the securement sleeve.

88. The method of either one of paragraph 86 or paragraph 87, comprising fixing the securement sleeve in the bent configuration with the medical tube disposed therethrough.

89. The method of paragraph 88, wherein:
the securement device comprises a bent sleeve holder selectively engageable and disengageable with the securement sleeve to selectively retain and not retain the securement sleeve in the bent configuration; and
the fixing comprises engaging the securement sleeve with the bent sleeve holder to retain the securement sleeve in the bent configuration.

90. The method of paragraph 89, wherein the bent sleeve holder is according to any one of paragraphs 2-27.

91. The method of any one of paragraphs 89-90, comprising adjusting a radial position of the bent sleeve holder relative to the securement sleeve, preferably by a radial distance of at least 5°, and optionally prior to the bending.

92. The method of paragraph 91, wherein the adjusting the radial position of the bent sleeve holder is performed prior to the engaging the securement sleeve with the bent sleeve holder to fix the securement sleeve in the bent configuration.

93. The method of either one of paragraph 91 or paragraph 92, wherein the adjusting the radial position is performed prior to the gripping the medical tube in the tube passage with the securement portion of the securement sleeve.

94. The method of either one of paragraph 91 or paragraph 92, wherein the adjusting the radial position is performed while the medical tube is gripped in the tube passage by the securement portion of the securement sleeve.

95. The method of any one of paragraphs 91-94, wherein the adjusting the radial position comprises rotating the rotating member relative to the base member of the securement device of any one of paragraphs 19-26.

96. The method of any one of paragraphs 91-95, comprising after the adjusting the radial position, locking the bent sleeve holder in place in a selected radial position with a radial positioning lock of the securement device, and optionally the locking comprises selective engagement of corresponding interlocking first and second lock structures of the base member and the rotating member of either one of paragraph 20 or paragraph 21.

97. The method of any one of paragraphs 86-96, wherein:
the securement sleeve has a proximal end disposed toward where the medical tube enters the body of the patient and a distal end opposite the proximal end; and
a portion of the medical tube in the securement sleeve has a maximum cross-dimension transverse to a longitudinal direction of the medical tube (e.g., outer diameter of a circular tube) and in the bent configuration at least a portion of, and preferably the entirety of, the medical tube in the tube passage in the securement sleeve distal of the bend in the tube is retained within a standoff distance from the body of the patient of not greater than 10 times, preferably not greater than 7 times and more preferably not greater than 6 times a maximum outer cross-dimension, and optionally the standoff distance is at least 3 times or even at least 4 times the maximum outer cross-dimension.

98. The method of any one of paragraphs 88-97, comprising releasing the securement sleeve from the bent configuration.

99. The method of paragraph 98, comprising after the releasing the securement sleeve from the bent configuration, applying longitudinally-applied compression to the securement portion to release the medical tube from being gripped by the securement portion.

100. The method of paragraph 99, comprising while applying the longitudinally-applied compression, removing the medical tube from the patient and from the securement sleeve; and
optionally, after the removing the medical tube, detaching the securement device from the patient.

101. The method of any one of paragraphs 85-98, comprising detaching the securement device from the patient and removing the medical tube from inside of the patient while the medical tube remains gripped by the securement portion of the securement sleeve; and
optionally, comprising a member selected from the group consisting of:
during the detaching the medical tube, and further optionally during the removing the medical tube, the medical tube is retained in the bent configuration of any one of paragraphs 86-97; and
prior to the detaching the medical tube, the medical tube in the bent configuration of any one of paragraphs 86-97 and is released from the bent configuration, and during the detaching the medical tube, and further optionally during the removing the medical tube, the medical tube is not in the bent configuration.

102. The method of paragraph 99, comprising, after the applying longitudinally-applied compression, performing a procedure selected from the group consisting of:
repositioning the medical tube within the securement portion to adjust a location of the medical tube in the patient, gripping the repositioned medical tube with the securement portion and then bending the securement sleeve with the repositioned medical tube into and fixing the securement sleeve in the bent configuration;
removing the medical tube from the patient and the securement sleeve, inserting a new medical tube through the securement sleeve and into the patient and then bending the securement sleeve with the new medical tube into and fixing the securement sleeve in the bent configuration; and
adjusting a radial position of the bent sleeve holder of any one of paragraphs 89-96 to a new radial position, locking the bent sleeve holder in place in the new radial position and then bending the securement sleeve with the medical tube into the bent configuration and fixing the securement sleeve in the bent configuration with the bent sleeve holder in the new radial position.

103. The method of any one of paragraphs 85-102, wherein:
prior to the gripping, the securement sleeve with the medical tube disposed therethrough is retained in a compressed configuration by a compression retainer, and in the compressed configuration the securement portion of the securement sleeve is under longitudinally-applied compression as a consequence of the compression retainer, and optionally the compression retainer is of the securement device of any one of paragraphs 28-38; and
the gripping comprises manipulating the compression retainer, optionally by disengaging the compression retainer from the securement device, to release the securement sleeve from the compressed configuration and to contract a cross-sectional area of the tube passage in the securement portion to grip the medical tube with the securement portion.

104. The method of any one of paragraphs 85-103, comprising attaching the securement device to the skin of the patient through an attachment pad of the securement device, optionally the attachment pad of the securement device of any one of paragraphs 1-69, and preferably the attaching comprises adhering the attachment pad to the skin with an adhesive.

105. The method of paragraph 104, wherein prior to the attaching, an adhesive surface of the attachment pad is covered by a peelable backing and the attaching comprises removing the backing to expose the adhesive surface and adhering the attachment pad to the skin with adhesive of the adhesive surface.

106. The method of either one of paragraph 104 or paragraph 105, wherein:
the attachment pad comprises an absorbent portion and the attaching comprises retaining the absorbent portion adjacent the skin; and
preferably, the absorbent portion has an aperture to receive therethrough the medical tube when inserted through the securement sleeve and into the patient, wherein the absorbent portion surrounds a periphery of the medical tube passing through the aperture, to absorb exudate from the patient.

107. The method of paragraph 106, wherein:
the absorbent portion comprises a fluid communication surface to be disposed toward the patient, optionally to contact the patient, and in fluid communication with the patient to absorb exudate from the patient when the attachment pad is attached to the skin of the patient;

the fluid communication surface of the absorbent portion is covered by the peelable backing prior to the removing the peelable backing; and the removing the peelable backing exposes the fluid communication surface of the absorbent portion.

108. The method of either one of paragraph 106 or paragraph 107, wherein;

the attachment pad comprises a structural sheet; and prior to the removing the peelable backing, the absorbent portion is disposed between the structural sheet and the peelable backing.

109. The method of either one of paragraph 107 or paragraph 108, wherein:

the attachment pad comprises a perforated layer of adhesive over a proximal face of the absorbent portion disposed toward the patient when the attachment pad is attached to the skin; and perforations through the perforated layer of adhesive provide fluid communication across the perforated layer of adhesive to the absorbent portion, providing for flow of exudate from the patient across the perforated layer of adhesive to be absorbed by the absorbent portion when the attachment pad is attached to the skin of the patient.

110. The method of paragraph 109, wherein;

prior to the removing the peelable backing, the perforations are covered by the peelable backing; and the perforations are exposed when the peelable backing is removed during the removing the peelable backing.

111. The method of any one of paragraphs 106-110, wherein the securement device is according to any one of paragraphs 48-61.1 comprising the absorbent portion, and optionally in the product or kit of any one of paragraphs 70-84.

112. The method of any one of paragraphs 104-111, comprising, prior to the attaching, preparing a site on the patient for attachment of attachment pad to the patient to secure the medical tube at the site, the preparing the site comprising a procedure selected from the group consisting of;

(a) treating skin at the site with a preparation wipe to improve the surface of the skin for adherence to the attachment pad, optionally using preparation wipe of the kit of paragraph 75;

(b) surgically forming an opening in the patient at the site to accept insertion of the medical tube, optionally using the tissue penetration instrument of the kit of paragraph 75;

(c) applying an adhesive component to skin at the site to assist adhesion of the attachment pad to the skin, optionally using the adhesion component of the kit of paragraph 75;

(d) cleaning the site with an antiseptic, optionally using an antiseptic wipe of the kit of paragraph 75;

(e) treating the site with an antimicrobial agent, optionally using the antimicrobial agent of the kit of paragraph 75; and combinations of any two, three, four or five of items (a)-(e).

113. The method of claim 112, comprising the procedure of item (b), and wherein the surgical opening accesses an anatomical region selected from the group consisting of intracranial, brain, stomach, small intestine, trachea, heart (e.g., atrium, ventricle), aorta, vena cava, intra-abdominal, thoracic cavity, intra-muscular, subcutaneous, colon, kidney, ureter, and bladder.

Method of Manufacture

114. A method of making a securement device or a product including a securement device, wherein the securement device is configured to secure to a patient a medical tube when inserted into the patient, and optionally the securement device is according to any one of paragraphs 1-69, the method comprising:

coupling a securement sleeve to a structural sheet for an attachment pad, optionally the attachment pad according to any one of paragraphs 1-69;

the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and the length of the securement sleeve is adjustable to expand the cross-sectional area to receive a medical tube for translation through the tube passage in the securement portion and to contract the cross-sectional area to grip the medical tube in the tube passage by the securement portion to secure the medical tube to the securement device, and preferably the securement sleeve is constructed of a textile, and optionally the securement sleeve is the securement sleeve according to any one of paragraphs 1-69; and the structural sheet for the attachment pad being configured with a proximal side to face a patient during use and a distal side to face away from a patient during use, the proximal side configured to be adhered with adhesive to skin of a patient; and wherein the coupling the securement sleeve to the structural sheet comprises:

securing flared end material adjacent a proximal end of the securement sleeve between a first surface of a first securement member and a second surface of a second securement member;

wherein the first securement member is selected from the group consisting of the structural sheet with the first surface being on the distal side of the structural sheet and an intermediate member coupled, directly or indirectly, to the distal side of the structural sheet; and optionally, and preferably, the second securement member is a base member according to any one of paragraphs 19-26.

115. The method of paragraph 114, wherein the securing the flared end material comprises sandwiching the flared end material between and adhering the flared end material to both the first surface to the second surface.

116. The method of paragraph 115, wherein prior to the sandwiching, at least one, and preferably both, of the first surface and the second surface has applied adhesive.

117. The method of paragraph 116, wherein the applied adhesive is pressure sensitive adhesive and the adhering comprises pressing together the first surface and the second surface together with sufficient pressure to activate the pressure sensitive adhesive to adhere the flared end material to the first and second surfaces, and preferably the pressure is at least 60 kilopascals (kPa).

118. The method of any one of paragraphs 114-117, comprising;

connecting a rotating member, optionally the rotating member of any one of paragraphs 19-26, to a preliminary product form for the securement device, the preliminary product form including the structural sheet, wherein as connected to the preliminary product form the rotating member is rotatable relative to the structural sheet;

optionally, and preferably, the preliminary product form includes the base member of any one of paragraphs 19-26, wherein the connection to the preliminary product form comprises engagement of the rotating member with the base member with the rotating member being rotatable relative to the base member between the base member and the rotating member is a rotatable connection with the rotating member being rotatable relative to the base member;

and preferably the connecting the rotating member to the preliminary product form occurs after any processing according to any of paragraphs 114-117.

119. The method of paragraph 118, wherein the connecting the rotating member to the preliminary product form comprises sliding the rotating member over the securement sleeve disposed through an aperture in the rotating member until the rotating member engages a connection location on the preliminary product form, and preferably the connection location is on the base member.

120. The method of either one of paragraph 118 or paragraph 119 wherein:

the connecting the rotating member to the preliminary product form comprises engaging the rotating member with exterior engagement features of an axle, and wherein as engaged with the axle the rotating member is rotatable about the axle; and optionally, and preferably, the axle comprises at least a portion of the extension portion of the base member according to paragraph 25.

121. The method of paragraph 120, wherein the axle has an aperture extending in a longitudinal direction through the axle, and preferably the aperture extends longitudinally through the extension portion of the base member, and the preliminary product form comprises the securement sleeve extending through the aperture of the axle, and preferably through the extension portion of the base member, and wherein as engaged with the axle the rotating member is rotatable about the securement sleeve.

122. The method of any one of paragraphs 114-121, comprising retaining a distal end portion of the securement sleeve in a distal collar assembly, optionally the distal collar assembly according to any one of paragraphs 45-47, and optionally the retaining a distal end portion of the securement sleeve occurs after the connecting a rotating member with the preliminary product form according to any one of paragraphs 118-121.

123. The method of paragraph 122, wherein the retaining a distal end portion of the securement sleeve in the distal collar assembly comprises:

inserting a collar nipple into the distal end portion of the securement sleeve and disposing a retaining member over the distal end portion of the securement sleeve biasing a sleeve wall of the distal end portion toward the collar nipple.

124. The method of any one of paragraphs 114-123, comprising attaching an absorbent pad to the proximal side of the structural sheet, and optionally the absorbent pad provides the absorbent portion according to any one of paragraphs 48-61.1.

125. The method of paragraph 124, wherein the attaching the absorbent pad to the proximal side of the structural sheet comprises:

applying adhesive over the proximal side of the structural sheet, preferably a pressure sensitive adhesive;

and after applying the adhesive, locating the absorbent pad to cover at least a portion of the adhesive over the proximal side of the structural sheet; and attaching the absorbent pad to the proximal side of the structural sheet with the adhesive.

126. The method of paragraph 125, comprising:

after the locating the absorbent pad to cover at least a portion of the adhesive, covering the absorbent pad, and optionally also covering an exposed portion of the adhesive on the proximal side of the structural sheet not covered by the absorbent pad, with a peelable backing; and adhering the peelable backing to the attachment pad with the absorbent pad disposed between the peelable backing and the structural sheet.

127. The method of paragraph 126, wherein the adhesive comprises pressure sensitive adhesive and the attaching the absorbent pad to the proximal side of the attachment pad comprises applying pressure to the absorbent pad disposed between the proximal side of the attachment pad and the peelable backing.

128. The method of any one of paragraphs 114-127, comprising applying longitudinally-applied compression to at least a portion of the securement sleeve to shorten the securement sleeve into a compressed configuration and retaining the securement sleeve in the compressed configuration with a compression retainer.

129. The method of paragraph 128, wherein the retaining the securement sleeve in the compressed configuration comprises engaging the compression retainer with the base member of any one of paragraphs 114-121 and with the distal collar assembly of either one of paragraph 122 or paragraph 123.

130. The method of any one of paragraphs 114-129, comprising:

completing the securement device; and sealing the securement device inside a hermetically-sealed enclosure, and optionally the securement device as sealed in the hermetically-sealed enclosure is in a product according to any one paragraphs 70-74; and sterilizing the securement device, optionally the sterilizing is performed prior to the sealing and alternatively optionally the sterilizing is performed after the sealing (e.g., by irradiation of the securement device within the hermetically-sealed enclosure).

131. The method of paragraph 130, comprising packaging within a common packaging enclosure the securement device together with at least one additional component for a kit according to any one of paragraphs 75-84, optionally the common packaging enclosure is the hermetically-sealed enclosure and alternatively optionally the common packaging enclosure encloses the hermetically-sealed enclosure containing the securement device or product including the securement device.

Other Medical Tube Features

132. The securement device, product, kit or method of any one of paragraphs 1-131, wherein a portion of the medical tube configured to be received through the securement portion has a maximum outer cross-dimension (e.g., outer diameter of a circular tube cross-section) that is larger than a maximum cross-dimension of the tube passage in the securement portion (e.g., inner diameter of circular tube cross-section) when the securement sleeve is in a relaxed state.

133. The securement device, product, kit or method of any one of paragraphs 1-132, wherein a portion of the medical tube configured to be received through the securement portion has a maximum outer cross-dimension (e.g., diameter of a circular tube cross-section), transverse to a longitudinal direction of the medical tube, in a range of from 2 to 14 millimeters (6 to 42 French gauge), and optionally the maximum outer cross-dimension is selected from the group consisting of about 2 millimeters (e.g., 6 French gauge), about 3.3 millimeters (e.g., 10 French gauge), about 5 millimeters (e.g., 15 French gauge), about 6.3 millimeters (e.g., 19 French gauge), about 8 millimeters (e.g., 24 French gauge), about 9.3 millimeters (e.g., 28 French gauge), about 10.7 millimeters (e.g., 32 French gauge) and about 14 millimeters (e.g., 42 French gauge).

134. The securement device, product, kit or method of any one of paragraphs 1-133, wherein a portion of the medical tube configured to be received through the securement sleeve has a circular outer perimeter in a cross-section transverse to a longitudinal direction of the medical tube, and preferably a fluid flow path through the medical tube has a circular cross-section.

135. The securement device, product, kit or method of any one of paragraphs 1-134, wherein the medical tube is made of a material of construction selected from the group consisting of silicone (polysiloxane), polyethylene and polyvinyl chloride.

The foregoing description of the present invention and various aspects thereof has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

Unless expressly stated otherwise or necessarily required by the context, for example based on feature incompatibility: description or illustration of a feature or features in a particular combination do not exclude inclusion in the combination of an additional feature or features; disclosed apparatus, kits, systems, and products may include additional features not disclosed, including intermediate structures between disclosed structures; references to coupling, attachment and the like of features or structures include direct coupling, attachment or the like of the features or structures and also include indirect coupling, attachment and the like including one or more additional intermediate structures or features; disclosure of elements or structure as being between other elements or structures does not preclude the inclusion of additional elements or structures also being between the other elements or structures; disclosures of processing steps and sequencing do not exclude inclusion of other steps or other sequencing of steps.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all. The term "at least a majority" means all or a majority part that is less than all.

What is claimed is:

1. A securement device to secure to a patient a medical tube when inserted into the patient, the securement device comprising:
    an attachment pad configured to interface with skin of the patient for attachment of the securement device to the skin;
    a variable-length securement sleeve having a proximal end and a distal end at a longitudinal end opposite the proximal end, the securement sleeve being coupled to the attachment pad through a coupling structure adjacent the proximal end of the securement sleeve;
    a tube passage configured to receive therethrough a medical tube for securement to the patient, the tube passage extending longitudinally through the securement sleeve;
    the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device;
    a bent sleeve holder selectively engageable and disengageable with the securement sleeve to selectively retain and not retain the securement sleeve in a bent configuration in which the securement sleeve has a bend in which the tube passage is correspondingly bent; and
    the bent sleeve holder configured to permit lengthening of the securement sleeve when the securement sleeve is retained in the bent configuration by the bent sleeve holder.

2. The securement device of claim 1, wherein the bent sleeve holder engages at least a longitudinal portion of the securement portion of the securement sleeve when the securement sleeve is engaged with the bent sleeve holder to retain the securement sleeve in the bent configuration.

3. The securement device of claim 2, wherein the bent sleeve holder comprises a retaining channel configured to receive a corresponding longitudinal portion of the securement sleeve in a received position to retain the securement sleeve in the bent configuration.

4. The securement device of claim 3, wherein the retaining channel extends longitudinally for a fixed radial distance relative to a longitudinal axis of the tube passage through the attachment pad when the securement sleeve is retained in the bent configuration by the bent sleeve holder and when the securement sleeve is not retained in the bent configuration by the bent sleeve holder.

5. The securement device of claim 3, wherein:
the retaining channel has an opening though which the corresponding longitudinal portion of the securement sleeve is inserted into the retaining channel to retain the securement sleeve in the bent configuration; and
the opening extends longitudinally for a fixed radial distance relative to a longitudinal axis of the tube passage through the attachment pad when the securement sleeve is retained in the bent configuration by the bent sleeve holder and when the securement sleeve is not retained in the bent configuration by the bent sleeve holder.

6. The securement device of claim 3, wherein the retaining channel has a longitudinally extending opening though which the corresponding longitudinal portion of the securement sleeve is inserted into the retaining channel to retain the securement sleeve in the bent configuration; and
the retaining channel is configured with the opening facing toward the attachment pad when the securement sleeve is retained in the bent configuration by the bent sleeve holder and when the securement sleeve is not retained in the bent configuration by the bent sleeve holder.

7. The securement device of claim 3, wherein the retaining channel has a longitudinally extending opening though which the corresponding longitudinal portion of the securement sleeve is inserted into the retaining channel to retain the securement sleeve in the bent configuration; and
the retaining channel is configured with the opening facing away from the attachment pad when the securement sleeve is retained in the bent configuration by the bent sleeve holder and when the securement sleeve is not retained in the bent configuration by the bent sleeve holder.

8. The securement device of claim 1, wherein the bent sleeve holder is rotationally mounted and rotatable to different radial positions relative to the attachment pad.

9. The securement device of claim 1, wherein:
the coupling structure comprises flared proximal end material of the securement sleeve sandwiched between a first securement member and a second securement member.

10. The securement device of claim 1, wherein the attachment pad comprises an absorbent portion configured to absorb exudate during use of the securement device.

11. The securement device of claim 10, wherein the tube passage extends through an aperture in the absorbent portion.

12. The securement device of claim 11, wherein the absorbent portion has a proximal face to be disposed toward the patient when the securement device is attached to the patient.

13. The securement device of claim 10, wherein;
the absorbent portion has an absorbent capacity of at least 500% by weight of 0.9% wt./vol. saline (isotonic saline) relative to the weight of the absorbent portion;
the absorbent capacity is at least 1 milliliter of the 0.9% wt./vol. saline (isotonic saline);
the absorbent portion comprises a proximal face configured to be disposed toward the skin of the patient;
the proximal face of the absorbent portion has a surface area of at least 4 square centimeters; and
the securement device comprises an opening in the proximal face of the absorbent portion for the tube passage.

14. The securement device of claim 1, wherein:
the securement sleeve is configured to retain in the securement portion a portion of the medical tube having a maximum outer cross-dimension, transverse to a longitudinal direction of the medical tube; and
the securement sleeve is configured to vary a maximum cross-dimension of the cross-sectional area at least over a range of from a lower limit of at least 1 millimeter smaller than the maximum outer cross-dimension and an upper limit of at least 1 millimeter larger than the maximum outer cross-dimension.

15. The securement device of claim 1, wherein the attachment pad comprises an antimicrobial agent.

16. A medical tube securement product, comprising:
the securement device of claim 1, wherein the attachment pad comprises an adhesive surface configured to adhere the attachment pad to the skin of the patient; and
a peelable backing adhered to and covering the adhesive surface and configured to be peeled from the adhesive surface to expose the adhesive surface for adherence of the attachment pad to the skin of the patient.

17. The product of claim 16, wherein;
the attachment pad of the securement device comprises an absorbent portion configured to absorb exudate during use of the securement device;
the absorbent portion comprises a proximal face configured to be disposed toward the skin of the patient; and
the peelable backing covers the proximal face of the absorbent portion and is configured to expose at least a portion of the proximal face of the absorbent portion when the peelable backing is peeled from the adhesive surface.

18. The product of claim 17, wherein the peelable backing is not adhered to the proximal face of the absorbent portion.

19. The product of claim 16, comprising a hermetically-sealed enclosure in which is disposed the securement device with the peelable backing adhered to the adhesive surface of the attachment pad, and with the securement device in the enclosure and an interior environment in the enclosure being sterile.

20. The securement device of claim 1, wherein the bent sleeve holder comprises a movable member that is movable between a first configuration in which the securement sleeve is not retained in the bent configuration and a second configuration in which the movable member contacts and biases the securement sleeve in the bent configuration.

21. The securement device of claim 1, wherein the bent sleeve holder is configured to permit movement of the distal end of the securement sleeve distally in an axial direction of a longitudinal axis of the tube passage when the securement sleeve is retained in the bent configuration by the bent sleeve holder.

22. A securement device to secure to a patient a medical tube when inserted into the patient, the securement device comprising:
an attachment pad configured to interface with skin of the patient for attachment of the securement device to the skin;

a variable-length securement sleeve having a proximal end and a distal end at a longitudinal end opposite the proximal end, the securement sleeve being coupled to the attachment pad through a coupling structure adjacent the proximal end of the securement sleeve;

a tube passage configured to receive therethrough a medical tube for securement to the patient, the tube passage extending longitudinally through the securement sleeve;

the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device; and a bent sleeve holder selectively engageable and disengageable with the securement sleeve to selectively retain and not retain the securement sleeve in a bent configuration in which the securement sleeve has a bend in which the tube passage is correspondingly bent;

wherein the bent sleeve holder is rotationally mounted and rotatable to different radial positions relative to the attachment pad.

23. The securement device of claim 22, wherein the radial positions are radially spaced about a longitudinal axis of the tube passage through the attachment pad and at all of the radial positions the bent sleeve holder extends to a fixed maximum radial distance from the longitudinal axis through the attachment pad when the securement sleeve is retained in the bent configuration by the bent sleeve holder and when the securement sleeve is not retained in the bent configuration by the bent sleeve holder.

24. The securement device of claim 23, wherein the attachment pad has a proximal side to be disposed facing the skin of the patient during use and the radial positions are radially spaced about an axis perpendicular to a face of the proximal side of the attachment pad.

25. The securement device of claim 23, comprising a radial positioning lock to selectively lock the bent sleeve holder at different ones of the radial positions.

26. The securement device of claim 22, comprising a base member and a rotating member that is rotatable relative to the base member, and wherein the bent sleeve holder is supported on the rotating member with fixed position and fixed orientation of the bent sleeve holder relative to the rotating member when the securement sleeve is retained in the bent configuration by the bent sleeve holder and when the securement sleeve is not retained in the bent configuration by the bent sleeve holder.

27. The securement device of claim 26, wherein:
the base member and the rotating member comprise corresponding interlocking first and second lock structures that are selectively engageable to lock a radial position of the rotating member at different ones of radial positions, with the first lock structure and the second lock structure on different ones of the base member and the rotating member.

28. The securement device of claim 27, wherein the first lock structure comprises at least one protrusion and the second lock structure comprises at least one recess configured to receive the at least one protrusion.

29. The securement device of claim 22, comprising a compression retainer disposed to retain the securement sleeve in a compressed configuration with the securement portion of the securement sleeve under longitudinally-applied compression with the cross-sectional area in an expanded configuration to receive therethrough the medical tube;

wherein the compression retainer is manipulable to release the securement portion from the longitudinally-applied compression to lengthen the securement sleeve and to contract the cross-sectional area relative to the expanded configuration, to permit the securement portion to grip the medical tube when disposed through the tube passage through the securement portion; and wherein when the securement portion is released from the longitudinally-applied compression the securement sleeve is bendable into the bent configuration in engagement with the bent sleeve holder.

30. The securement device of claim 29, comprising a distal collar adjacent the distal end of the securement sleeve, and wherein:
the compression retainer engages the distal collar with the securement sleeve retained in the compressed configuration; and
the compression retainer is configured for complete disengagement of the compression retainer from the distal collar to release the securement portion from the longitudinally-applied compression.

31. The securement sleeve of claim 30, comprising a base member and a rotating member that is rotatable relative to the base member and the bent sleeve holder is supported on the rotating member, and wherein:
the base member comprises an extension portion extending through an aperture in the rotating member, and the rotating member is rotatable about the extension portion;
the compression retainer engages the extension portion with the securement sleeve retained in the compressed configuration; and
the compression retainer is configured for complete disengagement of the compression retainer from the extension portion to release the securement portion from the longitudinally-applied compression.

32. The securement device of claim 22, wherein the attachment pad comprises an absorbent portion configured to absorb exudate during use of the securement device and the tube passage extends through an aperture in the absorbent portion.

33. The securement device of claim 22, wherein:
the bent sleeve holder comprises a retaining channel configured to receive a corresponding longitudinal portion of the securement sleeve in a received position to retain the securement sleeve in the bent configuration; and
the retaining channel extends longitudinally for a fixed radial distance relative to a longitudinal axis of the tube passage through the attachment pad when the securement sleeve is retained in the bent configuration by the bent sleeve holder and when the securement sleeve is not retained in the bent configuration by the bent sleeve holder.

34. A securement device to secure to a patient a medical tube when inserted into the patient, the securement device comprising:

an attachment pad configured to interface with skin of the patient for attachment of the securement device to the skin;
a variable-length securement sleeve having a proximal end and a distal end at a longitudinal end opposite the proximal end, the securement sleeve being coupled to the attachment pad through a coupling structure adjacent the proximal end of the securement sleeve;
a tube passage configured to receive therethrough a medical tube for securement to the patient, the tube passage extending longitudinally through the securement sleeve;
the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device;
a bent sleeve holder selectively engageable and disengageable with the securement sleeve to selectively retain and not retain the securement sleeve in a bent configuration in which the securement sleeve has a bend in which the tube passage is correspondingly bent; and
a compression retainer disposed to retain the securement sleeve in a compressed configuration with the securement portion of the securement sleeve under longitudinally-applied compression with the cross-sectional area in an expanded configuration to receive therethrough the medical tube;
wherein the compression retainer is manipulable to release the securement portion from the longitudinally-applied compression to lengthen the securement sleeve and to contract the cross-sectional area relative to the expanded configuration, to permit the securement portion to grip the medical tube when disposed through the tube passage through the securement portion; and
wherein when the securement portion is released from the longitudinally-applied compression the securement sleeve is bendable into the bent configuration in engagement with the bent sleeve holder.

35. The securement device of claim 34, wherein:
the securement sleve has a released configuration when the securement sleve is released from the compressed configuration with nothing disposed in the tube passage through the securement sleve, the length of the securement sleve being larger in the released configuration than in the compressed configuration;
a minimum insertion cross-section of the tube passage in the securement portion, transverse to the longitudinal path of the tube passage through the securement portion, varies as the length of the securement sleeve is varied, wherein the minimum insertion cross-section is larger in the compressed configuration than in the released configuration;
the minimum insertion cross-section has a maximum cross-dimension;
the minimum insertion cross-section is configured to receive in the compressed configuration and retain in the released configuration a corresponding outer cross-section of the medical tube, the outer cross-section having a maximum outer cross-dimension; and
in the released configuration, the maximum cross-dimension of the minimum insertion cross-section is at least 0.5 millimeter smaller than the maximum outer cross-dimension of the outer cross-section of the medical tube.

36. The securement device of claim 34, comprising a distal collar adjacent the distal end of the securement sleeve; and
wherein the compression retainer engages the distal collar with the securement sleeve retained in the compressed configuration.

37. The securement device of claim 36, wherein the compression retainer is configured for complete disengagement from the distal collar to release the securement portion from the longitudinally-applied compression.

38. The securement device of claim 34, wherein the compression retainer is configured for complete disengagement from all other portions of the securement device to release the securement portion from the longitudinally-applied compression.

39. A method of securing a medical tube to a patient with a securement device, wherein the securement device comprises:
an attachment pad configured to interface with skin of the patient for attachment of the securement device to the skin of the patient;
a variable-length securement sleeve having a proximal end and a distal end at a longitudinal end opposite the proximal end, the securement sleeve being coupled to the attachment pad through a coupling structure adjacent the proximal end of the securement sleeve;
a tube passage configured to receive therethrough the medical tube for securement to the patient, the tube passage extending longitudinally through the securement sleeve;
the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device;
a bent sleeve holder selectively engageable and disengageable with the securement sleeve to selectively retain and not retain the securement sleeve in a bent configuration in which the securement sleeve has a bend in which the tube passage is correspondingly bent; and
the bent sleeve holder configured to permit lengthening of the securement sleeve when the securement sleeve is retained in the bent configuration by the bent sleeve holder;
the method comprising:
with the medical tube extending through the tube passage and into a body of the patient, gripping the medical tube in the tube passage with the securement portion of the securement sleeve.

40. The method of claim 39, comprising, with the medical tube gripped by the securement portion in the tube passage,:

bending the securement sleeve to a bent configuration to impart a corresponding bend in the medical tube in the tube passage in the securement sleeve; and engaging the securement sleeve with the bent sleeve holder to retain the securement sleeve in the bent configuration.

41. The method of claim 40, wherein;
the bent sleeve holder is rotationally mounted and rotatable to different radial positions relative to the attachment pad;
the radial positions are radially spaced about a longitudinal axis of the tube passage through the attachment pad;
at all of the radial positions the bent sleeve holder extends to a fixed maximum radial distance from the longitudinal axis through the attachment pad when the securement sleeve is retained in the bent configuration by the bent sleeve holder and when the securement sleeve is not retained in the bent configuration by the bent sleeve holder; and
the method comprises adjusting a radial position of the bent sleeve holder relative to the securement sleeve.

42. The method of claim 41, wherein;
the securement device comprises a base member and a rotating member that is rotatable relative to the base member and the bent sleeve holder is supported on the rotating member; and
the adjusting the radial position comprises rotating the rotating member relative to the base member.

43. The method of claim 42, comprising after the adjusting the radial position, locking the bent sleeve holder in place in a selected one of the radial positions with a radial positioning lock of the securement device;
wherein the radial positioning lock comprises interlocking first and second lock structures that are selectively engageable to lock the rotating member at different ones of the radial positions, with the first lock structure and the second lock structure on different ones of the base member and the rotating member;
wherein the first lock structure comprises at least one protrusion and the second lock structure comprises at least one recess configured to receive the at least one protrusion; and
wherein the locking comprises after the adjusting the radial position, engaging the at least one protrusion and the at least one recess with the at least one protrusion received in the at least one recess.

44. The method of claim 42, wherein the bent sleeve holder is supported on the rotating member with fixed position and fixed orientation of the bent sleeve holder relative to the rotating member when the securement sleeve is retained in the bent configuration by the bent sleeve holder and when the securement sleeve is not retained in the bent configuration by the bent sleeve holder.

45. The method of claim 40, wherein:
prior to the gripping, the securement sleeve with the medical tube disposed therethrough is retained in a compressed configuration by a compression retainer, and in the compressed configuration the securement portion of the securement sleeve is under longitudinally-applied compression as a consequence of the compression retainer; and
the gripping comprises manipulating the compression retainer to release the securement sleeve from the compressed configuration to lengthen the securement sleeve and to contract the cross-sectional area of the tube passage in the securement portion to grip the medical tube with the securement portion.

46. The method of claim 40, wherein:
the bent sleeve holder comprises a retaining channel configured to receive a corresponding longitudinal portion of the securement sleeve in a received position to retain the securement sleeve in the bent configuration;
the retaining channel extends longitudinally for a fixed radial distance relative to a longitudinal axis of the tube passage through the attachment pad when the securement sleeve is retained in the bent configuration by the bent sleeve holder and when the securement sleeve is not retained in the bent configuration by the bent sleeve holder; and
the engaging comprises disposing the corresponding longitudinal portion of the securement sleeve in the retaining channel in the received position.

47. The method of claim 46, wherein:
the retaining channel has a longitudinally extending opening though which the corresponding longitudinal portion of the securement sleeve is inserted into the retaining channel to dispose the corresponding longitudinal portion of the securement sleeve in the received position;
the disposing comprises inserting the corresponding longitudinal portion of the securement sleeve through the opening into the retaining channel.

48. The method of claim 47, wherein the retaining channel is configured with the opening facing toward the attachment pad when the securement sleeve is retained in the bent configuration by the bent sleeve holder and when the securement sleeve is not retained in the bent configuration by the bent sleeve holder.

49. The method of claim 47, wherein the retaining channel is configured with the opening facing away from the attachment pad when the securement sleeve is retained in the bent configuration by the bent sleeve holder and when the securement sleeve is not retained in the bent configuration by the bent sleeve holder.

50. The method of claim 39, wherein in the bent configuration the securement sleeve, and the medical tube in the tube passage in the securement sleeve, is bent by an angle of at least 60° between longitudinal ends of the securement sleeve.

51. The method of claim 39, comprising attaching the securement device to the skin of the patient through the attachment pad.

52. The method of claim 51, wherein:
prior to the attaching, an adhesive surface of the attachment pad is covered by a peelable backing; and
the attaching comprises removing the peelable backing to expose the adhesive surface and adhering the attachment pad to the skin with adhesive of the adhesive surface.

53. The method of claim 51, wherein:
the attachment pad comprises an absorbent portion and the attaching comprises retaining the absorbent portion adjacent the skin to absorb exudate from the patient; and
the absorbent portion has an aperture to receive therethrough the medical tube when inserted through the securement sleeve and into the patient, wherein the absorbent portion surrounds a periphery of the medical tube passing through the aperture.

54. The method of claim 53, wherein:
the attaching comprises adhering the attachment pad to the skin of the patient with an adhesive of an adhesive surface of the attachment pad;

prior to the attaching, the adhesive surface of the attachment pad is covered by a peelable backing; and
the attaching comprises removing the peelable backing to expose the adhesive surface;
the absorbent portion comprises a fluid communication surface to be disposed toward the patient and in fluid communication with the patient to absorb the exudate from the patient when the attachment pad is attached to the skin of the patient;
the fluid communication surface of the absorbent portion is covered by the peelable backing prior to the removing the peelable backing;
the removing the peelable backing exposes the fluid communication surface of the absorbent portion;
the attachment pad comprises a structural sheet; and
prior to the removing the peelable backing, the absorbent portion is disposed between the structural sheet and the peelable backing.

55. The method of claim 53, wherein
the attaching comprises adhering the attachment pad to the skin of the patient with an adhesive of an adhesive surface of the attachment pad;
prior to the attaching, the adhesive surface of the attachment pad is covered by a peelable backing and the attaching comprises removing the peelable backing to expose the adhesive surface;
the absorbent portion comprises a fluid communication surface disposed toward the patient and in fluid communication with the patient to absorb the exudate from the patient when the attachment pad is attached to the skin of the patient, and wherein the aperture extends through the fluid communication surface;
the fluid communication surface and the aperture are covered by the peelable backing prior to the removing the peelable backing; and
the removing the peelable backing exposes the fluid communication surface and the aperture.

56. A method of securing a medical tube to a patient with a securement device, wherein the securement device comprises:
an attachment pad configured to interface with skin of the patient for attachment of the securement device to the skin of the patient;
a variable-length securement sleeve having a proximal end and a distal end at a longitudinal end opposite the proximal end, the securement sleeve being coupled to the attachment pad through a coupling structure adjacent the proximal end of the securement sleeve;
a tube passage configured to receive therethrough the medical tube for securement to the patient, the tube passage extending longitudinally through the securement sleeve;
the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device; and
a bent sleeve holder selectively engageable and disengageable with the securement sleeve to selectively retain and not retain the securement sleeve in a bent configuration in which the securement sleeve has a bend in which the tube passage is correspondingly bent;
wherein the bent sleeve holder is rotationally mounted and rotatable to different radial positions relative to the attachment pad;
the method comprising:
with the medical tube extending through the tube passage and into a body of the patient, gripping the medical tube in the tube passage with the securement portion of the securement sleeve.

57. The method of claim 56, comprising adjusting a radial position of the bent sleeve holder, comprising:
unlocking the bent sleeve holder from a first one of the radial positions;
rotating the bent sleeve holder relative to the attachment pad to adjust a radial position of the bent sleeve holder; and
after the rotating, locking the bent sleeve holder in place in a selected one of the radial positions that is different than the first one of the radial positions.

58. The method of claim 57, comprising during the gripping, bending the securement sleeve and the medical tube in the tube passage and engaging the securement sleeve with the bent sleeve holder to retain the securement sleeve in the bent configuration with the medical tube extending through the tube passage and into the body of the patient.

59. The method of claim 58, comprising, prior to the gripping, attaching the securement device to the skin of the patient through the attachment pad; and
during the gripping the securement device is attached to the skin of the patient through the attachment pad.

60. The method of claim 59 wherein:
the attachment pad comprises an absorbent portion and the attaching comprises retaining the absorbent portion adjacent the skin to absorb exudate from the patient; and
the absorbent portion has an aperture to receive therethrough the medical tube when inserted through the securement sleeve and into the patient, and during the gripping the absorbent portion surrounds a periphery of the medical tube passing through the aperture.

61. The method of clam 60, wherein:
the absorbent portion has a proximal face facing the skin of the patient when the securement device is attached to the patient after the attaching;
prior to the attaching, the proximal face of the attachment pad is covered by a peelable backing: and
the attaching comprises removing the peelable backing to expose an adhesive surface of the attachment pad and adhering the attachment pad to the skin with adhesive of the adhesive surface.

62. The method of claim 57, wherein:
the securement device comprises a base member and a rotating member that is rotatable relative to the base member and the bent sleeve holder is supported on the rotating member; and
the rotating comprises rotating the rotating member relative to the base member.

63. The method of claim 62, wherein:
the securement device comprises a radial positioning lock comprising interlocking first and second lock structures that are selectively engageable to lock the rotating member at different ones of the radial positions, with the first lock structure and the second lock structure on different ones of the base member and the rotating member; and the adjusting the radial position of the bent sleeve holder comprises, before the rotating, disengaging the first lock structure and the second lock structure to unlock the bent sleeve holder from the first radial position and, after the rotating, engaging the first lock structure and the second lock structure to lock the bent sleeve holder at the selected one of the radial positions.

64. The method of claim 63, wherein:
the first lock structure comprises at least one protrusion and the second lock structure comprises at least one recess configured to receive the at least one protrusion; and
the disengaging comprises disengaging the at least one protrusion from the at least one recess with the bent sleeve holder at the first one of the radial positions and the engaging comprises engaging the at least one protrusion with the at least one recess with the bent sleeve holder at the selected one of the radial positions.

65. The method of clam 73, wherein:
the radial positions are radially spaced about a longitudinal axis of the tube passage through the attachment pad; and
at all of the radial positions the bent sleeve holder extends to a fixed maximum radial distance from the longitudinal axis through the attachment pad when the securement sleeve is retained in the bent configuration by the bent sleeve holder and when the securement sleeve is not retained in the bent configuration by the bent sleeve holder.

66. The method of claim 57, wherein during the adjusting, the medical tube is extending through the tube passage and into the body of the patient.

67. The method of claim 66, wherein the adjusting occurs prior to the gripping the medical tube in the tube passage with the securement portion of the securement sleeve.

68. The method of claim 67, comprising during the gripping, bending the securement sleeve and the medical tube in the tube passage and engaging the securement sleeve with the bent sleeve holder to retain the securement sleeve in the bent configuration with the medical tube extending through the tube passage and into the body of the patient.

69. A method of securing a medical tube to a patient with a securement device, wherein the securement device comprises:
an attachment pad configured to interface with skin of the patient for attachment of the securement device to the skin of the patient;
a variable-length securement sleeve having a proximal end and a distal end at a longitudinal end opposite the proximal end, the securement sleeve being coupled to the attachment pad through a coupling structure adjacent the proximal end of the securement sleeve;
a tube passage configured to receive therethrough the medical tube for securement to the patient, the tube passage extending longitudinally through the securement sleeve;
the securement sleeve including a securement portion through which the tube passage extends, wherein a cross-sectional area of the tube passage in the securement portion transverse to a longitudinal path of the tube passage expands as the securement sleeve is shortened and contracts as the securement sleeve is lengthened and a length of the securement sleeve is adjustable to expand the cross-sectional area to receive the medical tube for translation through the tube passage in the securement portion and to contract the cross-sectional area to grip the medical tube in the tube passage by the securement portion to secure the medical tube to the securement device;
a bent sleeve holder selectively engageable and disengageable with the securement sleeve to selectively retain and not retain the securement sleeve in a bent configuration in which the securement sleeve has a bend in which the tube passage is correspondingly bent; and
a compression retainer disposed to retain the securement sleeve in a compressed configuration with the securement portion of the securement sleeve under longitudinally-applied compression with the cross-sectional area in an expanded configuration to receive therethrough the medical tube;
wherein the compression retainer is manipulable to release the securement portion from the longitudinally-applied compression to lengthen the securement sleeve and to contract the cross-sectional area relative to the expanded configuration, to permit the securement portion to grip the medical tube when disposed through the tube passage through the securement portion; and
wherein when the securement portion is released from the longitudinally-applied compression the securement sleeve is bendable into the bent configuration in engagement with the bent sleeve holder;
the method comprising:
with the medical tube extending through the tube passage and into a body of the patient, manipulating the compression retainer to release the securement sleeve from the compressed configuration to lengthen the securement sleeve and to contract the cross-sectional area of the tube passage in the securement portion to grip the medical tube with the securement portion.

70. The method of claim 69, comprising, after the manipulating and with the medical tube gripped by the securement portion in the tube passage:
bending the securement sleeve to a bent configuration to impart a corresponding bend in the medical tube in the tube passage in the securement sleeve; and
engaging the securement sleeve with the bent sleeve holder to retain the securement sleeve in the bent configuration.

* * * * *